(12) United States Patent
Bittner et al.

(10) Patent No.: US 8,455,638 B2
(45) Date of Patent: Jun. 4, 2013

(54) SOLUBLE GUANYLATE CYCLASE ACTIVATORS

(75) Inventors: Amy R. Bittner, Westfield, NJ (US); Ronald M. Kim, Summit, NJ (US); John W. Mirc, Tokyo (JP); Emma R. Parmee, Doylestown, PA (US); Christopher Joseph Sinz, Middletown, NJ (US); Qiang Tan, Westfield, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 165 days.

(21) Appl. No.: 12/674,795

(22) PCT Filed: Sep. 2, 2008

(86) PCT No.: PCT/US2008/010321
§ 371 (c)(1),
(2), (4) Date: Feb. 23, 2010

(87) PCT Pub. No.: WO2009/032249
PCT Pub. Date: Mar. 12, 2009

(65) Prior Publication Data
US 2011/0118282 A1    May 19, 2011

Related U.S. Application Data

(60) Provisional application No. 60/967,827, filed on Sep. 6, 2007.

(51) Int. Cl.
C07D 345/00 (2006.01)
C07D 517/00 (2006.01)
C07D 413/00 (2006.01)
C07D 401/00 (2006.01)

(52) U.S. Cl.
USPC ............... 540/1; 546/269.1; 546/275.4

(58) Field of Classification Search
USPC ..................... 540/1; 546/269.1, 275.4
See application file for complete search history.

(56) References Cited

U.S. PATENT DOCUMENTS

| 6,162,819 A | 12/2000 | Schindler et al. |
| 2001/0044445 A1 | 11/2001 | Bamaung et al. |
| 2010/0075964 A1 | 3/2010 | Busch et al. |
| 2010/0216764 A1 | 8/2010 | Kim et al. |
| 2010/0331295 A1 | 12/2010 | Busch et al. |
| 2011/0028493 A1 | 2/2011 | Matsunaga et al. |

FOREIGN PATENT DOCUMENTS

| CA | 2039770 | 10/1991 |
| DE | 19744026 | 4/1999 |
| DE | 19744027 | 4/1999 |
| EP | 0908456 | 4/1999 |
| WO | 00/27394 | 5/2000 |
| WO | 02/074753 | 9/2002 |
| WO | 03/031435 | 4/2003 |
| WO | 2004/047730 | 6/2004 |
| WO | 2004/092140 | 10/2004 |
| WO | 2006/134459 | 12/2006 |
| WO | 2006/134468 | 12/2006 |
| WO | 2008/045484 | 4/2008 |
| WO | 2009/068652 | 6/2009 |
| WO | 2009/071504 | 6/2009 |
| WO | 2009/123316 | 10/2009 |
| WO | 2010/015652 | 2/2010 |
| WO | 2010/015653 | 2/2010 |
| WO | 2012/058132 | 5/2012 |

OTHER PUBLICATIONS

Int'l Search Report re PCT/US2008/010321, dated Dec. 18, 2008.
Int'l Preliminary Report on Patentability re PCT/US2008/010321, dated Mar. 9, 2010.

*Primary Examiner* — Marcos Sznaidman
(74) *Attorney, Agent, or Firm* — Carol S. Quagliato; Catherine D. Fitch

(57) ABSTRACT

A compound having the structure

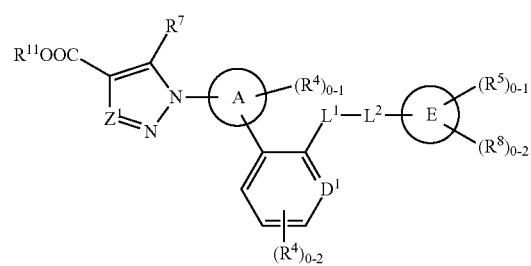

useful for treatment or prevention of cardiovascular diseases, endothelial dysfunction, diastolic dysfunction, atherosclerosis, hypertension, angina pectoris, thromboses, restenoses, myocardial infarction, strokes, cardiac insufficiency, pulmonary hypertonia, erectile dysfunction, asthma bronchiale, chronic kidney insufficiency, diabetes, or cirrhosis of the liver in a human or animal patient.

23 Claims, No Drawings

SOLUBLE GUANYLATE CYCLASE ACTIVATORS

CROSS REFERENCE TO RELATED APPLICATIONS

This application is a U.S. National Phase application under 35 U.S.C. §.371 of PCT Application No. PCT/US2008/010321, filed Sep. 2, 2008, which claims priority under 35 U.S.C. §119 from U.S. Application No. 60/967,827, filed Sep. 6, 2007.

BACKGROUND OF THE INVENTION

Cyclic GMP is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are composed of an α and β subunit each. Several subunit subtypes have been described which differ from one another with respect to sequence, tissue-specific distribution and expression in different development stages. The subtypes $\alpha_1$ and $\beta_1$ are mainly expressed in brain and lung, while $\beta_2$ is found in particular in liver and kidney. The subtype $\alpha_2$ was shown to be present in human fetal brain. The subunits referred to as $\alpha_3$ and $\beta_3$ were isolated from human brain and are homologous to $\alpha_1$ and $\beta_1$. More recent works indicate an $\alpha_{2i}$ subunit which contains an insert in the catalytic domain. All subunits show great homologies in the region of the catalytic domain. The enzymes presumably contain one heme per heterodimer, which is bound via $\beta_1$-Cys-78 and/or $\beta_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thromboses, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of guanylate cyclase and are therefore suitable for the therapy and prophylaxis of disorders which are associated with a low cGMP level.

SUMMARY OF THE INVENTION

The present invention relates to compounds which activate soluble guanylate cyclase which are valuable pharmaceutically active compounds for the therapy and prophylaxis of diseases, for example for cardiovascular diseases such as hypertension, angina pectoris, diabetes, cardiac insufficiency, thromboses or atherosclerosis. The compounds of the formula I are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of the formula I, to their use for the therapy and prophylaxis of the above-mentioned diseases and for preparing pharmaceuticals for this purpose, and to pharmaceutical preparations which comprise compounds of the formula I.

DETAILED DESCRIPTION OF THE INVENTION AND PREFERRED EMBODIMENTS

The invention concerns compounds of formula I which activate soluble guanylate cyclase:

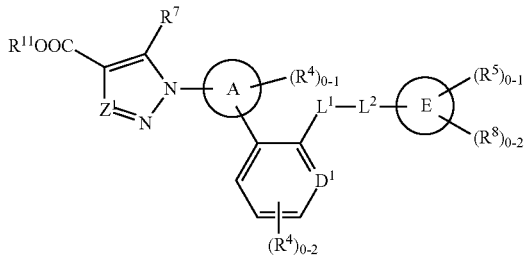

and pharmaceutically acceptable salts thereof, wherein
$Z^1$ is selected from the group consisting of CH and N;
A is a ring selected from the group consisting of

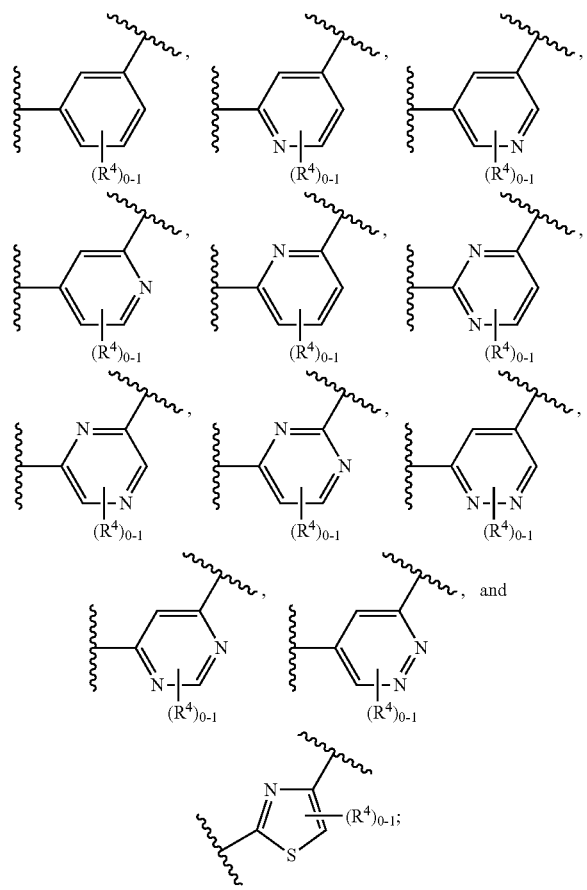

$D^1$ is CH, $CR^4$ or N;
$R^7$ is selected from the group consisting of
1) hydrogen,
2) $C_{1-6}$ alkyl wherein the alkyl group may be unsubstituted or substituted with 1-3 fluorine atoms and unsubstituted or monosubstituted with $OC_{1-3}$ alkyl,
3) $C_{3-6}$ cycloalkyl wherein the cycloalkyl group may be unsubstituted or substituted with 1-3 fluorine atoms and unsubstituted or monosubstituted with $OC_{1-3}$ alkyl, and
4) phenyl, wherein the phenyl group is unsubstituted or substituted with $C_{1-4}$ alkyl, —$OC_{1-4}$ alkyl, halogen, CN, $NO_2$, and $S(O)_{0-2}C_{1-4}$ alkyl, wherein $C_{1-4}$ alkyl and —$OC_{1-4}$ alkyl are unsubstituted or substituted with 1-3 flourine atoms;
$L^1$ is selected from the group consisting of O, S, $C(R^{12})_2$; and $CF_2$;
$L^2$ is selected from the group consisting of $(CH_2)_{2-4}$, —$C(R^{12})_2$, —$CF_2$—O, and S, provided that when $L^1$ is O or S, $L^2$ is not O or S;
$R^{12}$ is independently selected from the group consisting of hydrogen and $C_{1-3}$ alkyl, wherein $C_{1-3}$ alkyl is unsubstituted or substituted with 1-3 flourine atoms;
E is a ring selected from the group consisting of
1) a 6-10 membered aryl ring,
2) a 5-10 membered heteroaryl ring having 1, 2 or 3 heteroatoms independently selected from the group consisting of 0, 1, 2, and 3N atoms, 0 or 1 O atoms, and 0 or 1 S atoms,
3) a $C_{3-8}$ cycloalkyl ring;
wherein aryl, heteroaryl, and $C_{3-8}$ cycloalkyl are unsubstituted or monosubstituted with $R^5$, and unsubstituted, monosubstituted or independently disubstituted with $R^8$;
$R^4$, in each instance in which it occurs, is independently selected from the group consisting of halogen,
$C_{1-6}$ alkyl, wherein the alkyl group may be unsubstituted or substituted with 1-3 fluorine atoms,
—O—$C_{1-6}$ alkyl, wherein the alkyl group may be unsubstituted or substituted with 1-3 fluorine atoms,
$C_{3-8}$ cycloalkyl, unsubstituted or substituted with 1-3 fluorine atoms,
—O—$C_{3-8}$ cycloalkyl, unsubstituted or substituted with 1-3 fluorine atoms,
CN, and
$NO_2$;
$R^5$, in each instance in which it occurs, is independently selected from the group consisting of
1) $R^6$,
2) —$OR^6$,
3) $C_{1-6}$ alkyl which may be unsubstituted or substituted with 1-3 fluorine atoms, and unsubstituted or monosubstituted with a group independently selected from $C_{3-6}$ cycloalkyl, —O—$C_{1-4}$ alkyl, OH, =O, $S(O)_{0-2}C_{1-4}$ alkyl, —$OR^6$ and $R^6$,
4) $C_{1-6}$ alkenyl which may be unsubstituted or substituted with 1-3 fluorine atoms and unsubstituted or monosubstituted with a group independently selected from —O—$C_{1-4}$ alkyl, OH, =O, $S(O)_{0-2}C_{1-4}$ alkyl, —$OR^6$ and $R^6$,
5) O—$C_{1-6}$ alkyl wherein the alkyl group may be unsubstituted or substituted with 1-3 fluorine atoms, and unsubstituted or monosubstituted with a group independently selected from $C_{3-6}$ cycloalkyl and $R^6$,
6) —S—$C_{1-6}$ alkyl,
7) a $C_{3-8}$ cycloalkyl ring which is unsubstituted or mono, di- or tri-substituted with groups independently selected from fluoro and $C_{1-4}$ alkyl, and unsubstituted or monosubstituted with a group independently selected from $C_{1-4}$ alkyl wherein the alkyl group may be unsubstituted or substituted with 1-3 fluorine atoms, —O—$C_{1-4}$ alkyl, OH, =O, $S(O)_{0-2}C_{1-4}$ alkyl, —$OR^6$, $R^6$, and $NR^9R^{10}$,
8) a $C_{5-8}$ cycloalkenyl ring which is unsubstituted or mono, di- or tri-substituted with a group independently selected from fluoro and $C_{1-4}$ alkyl, and unsubstituted or monosubstituted with a group independently selected from $C_{1-4}$ alkyl, wherein the allyl group may be unsubstituted or substituted with 1-3 fluorine atoms, —O—$C_{1-4}$ alkyl, OH, =O, $S(O)_{0-2}C_{1-4}$ alkyl, and $R^6$, 9) a 5- to 6 membered heterocyclyl ring having 1 or 2 heteroatoms selected from the group consisting of N, O and S, and which is unsubstituted or monosubstituted with a group independently selected from $C_{1-4}$ alkyl wherein the alkyl group may be unsubstituted or substituted with 1-3 fluorine atoms, —$OC_{1-4}$ alkyl, and =O, and 10) halogen;

$R^6$ is selected from the group consisting of 1) a phenyl ring which is unsubstituted, monosubstituted or disubstituted with a group independently selected from the group consisting of halogen, OH, CN, $C_{1-4}$ alkyl wherein the alkyl group may be unsubstituted or substituted with 1-3 fluorine atoms, $OC_{1-4}$ alkyl wherein the alkyl group may be unsubstituted or substituted with 1-3 fluorine atoms, $NO_2$, $S(O)_{0-2}C_{1-4}$ alkyl, $C_{2-4}$ alkenyl, O—$C_{2-4}$ alkenyl, $NR^9R^{10}$, and COOH, and 2) a 5-6 membered heteroaryl ring containing 1-2 heteroatoms which are independently selected from N, O and S, wherein the heteroaryl ring is unsubstituted, monosubstituted or disubstituted with a group independently selected from: halogen, OH, CN, $C_{1-4}$ alkyl wherein the alkyl group may be unsubstituted or substituted with 1-3 fluorine atoms, $OC_{1-4}$ alkyl wherein the alkyl group may be unsubstituted or substituted with 1-3 fluorine atoms, $NO_2$, $S(O)_{0-2}C_{1-6}$ alkyl, $S(O)_{0-2}$ aryl, $C_{2-6}$ alkenyl, $OC_{2-6}$ alkenyl, $NR^9R^{10}$, and COOH;

$R^8$ is selected from the group consisting of $C_{1-4}$ alkyl wherein the alkyl group may be unsubstituted or substituted with 1-3 fluorine atoms, $C_{2-4}$ alkenyl, halogen, $C_{3-6}$ cycloalkyl, wherein the cycloalkyl group may be unsubstituted or substituted with 1-3 fluorine atoms $OC_{1-4}$ alkyl wherein the alkyl group may be unsubstituted or substituted with 1-3 fluorine atoms, O—$C_{2-4}$ alkenyl, $NO_2$, $S(O)_{0-2}C_{1-4}$ alkyl, and

CN;

$R^9$ and $R^{10}$ are independently selected from the group consisting of hydrogen and $C_{1-6}$ alkyl; and $R^{11}$ is selected from the group consisting of hydrogen and $C_{1-6}$ alkyl.

In another embodiment, A is a ring selected from the group consisting of

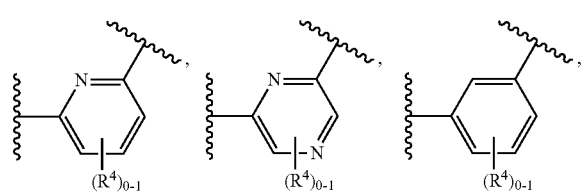

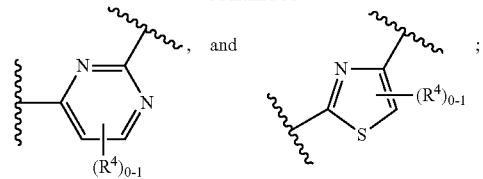

and all other variables are as previously defined.

In another embodiment, $R^{11}$ is hydrogen, and all other variables are as previously defined.

In another embodiment,

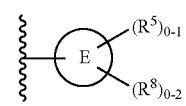

is selected from the group consisting of

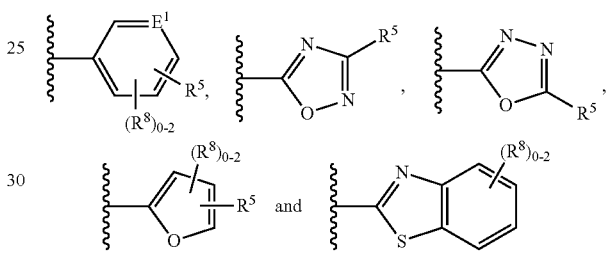

wherein $E^1$ is CH or N, and all other variables are previously defined.

In another embodiment,

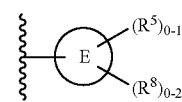

is selected from the group consisting of

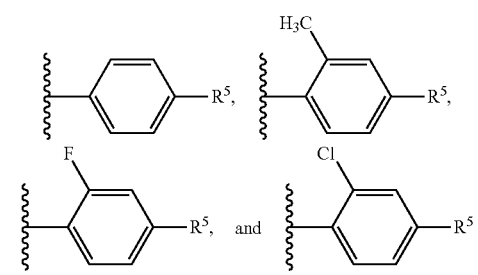

and all other variables are as previously defined.

In another embodiment, $Z^1$ is CH, and all other variables are as previously defined.

In another embodiment, $R^7$ is selected from the group consisting of $CH_3$, $CF_3$ and $CF_2H$, and all other variables are as previously defined.

In another embodiment, $L^1$ is selected from a group consisting of O and S, and all other variables are as previously defined.

In another embodiment, $L^2$ is selected from the group consisting of $CH_2$, $CH(CH_3)$, O, $CH_2CH_2$, $CF_2$ and $CH_2CH_2CH_2$, provided that when $L^2$ is O $L^1$ is not O, and all other variables are as previously defined In another embodiment, $L^2$ is selected from the group consisting of $CH_2$ and $CF_2$, and all other variables are as previously defined.

In another embodiment, $R^4$ is selected from the group consisting of Cl, F, Br, $CH_3$, cyclopropyl, $NO_2$, and $CF_3$, and all other variables are as previously defined.

In another embodiment, $R^4$ is selected from the group consisting of $C_1$ and $CH_3$, and all other variables are as previously defined In another embodiment, $R^6$ is a phenyl ring which is unsubstituted or mono, di- or tri-substituted with a group independently selected from the group consisting of Cl, F, —$CH_3$, —$C(CH_3)_3$, $CF_3$, —$OCF_3$, —$OCH_3$, —$OCH(CH_3)_2$ and COOH, and all other variables are as previously defined.

In another embodiment, $R^5$ is selected from the group consisting of
1) $R^6$,
2) a $C_{3-6}$ cycloalkyl ring which is unsubstituted or mono, di- or tri-substituted with a group independently selected from phenyl, F, $CF_3$, $CH_3$, OH, and =O,
3) a pyridinyl ring, wherein the point of attachment to the pyridinyl ring is a carbon atom, and wherein the pyridinyl ring is unsubstituted or mono-substituted with $CF_3$,
4) —$CH_2$-$L^3$-$R^6$, wherein $L^3$ is —$CH_2$— or —O—,
5) —$OR^6$,
6) —$OCH_2R^6$,
7)

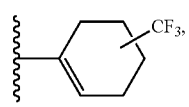

8) —$CF_3$,
9) Cl, F, or Br,
10) —$CH_3$,
11) $OCH_3$,
12) $OCF_3$,
13) —CH=$CHR^6$, and
14) —$SCH_2CH_3$,
and all other variables are as previously defined.

In another embodiment, $R^5$ is selected from the group consisting of Cl, F, Br, —$CH_3$, —$C(CH_3)_3$, $OCH_3$, $OCF_3$, —$SCH_2CH_3$,

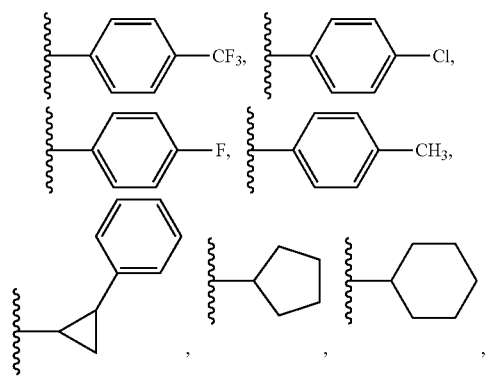

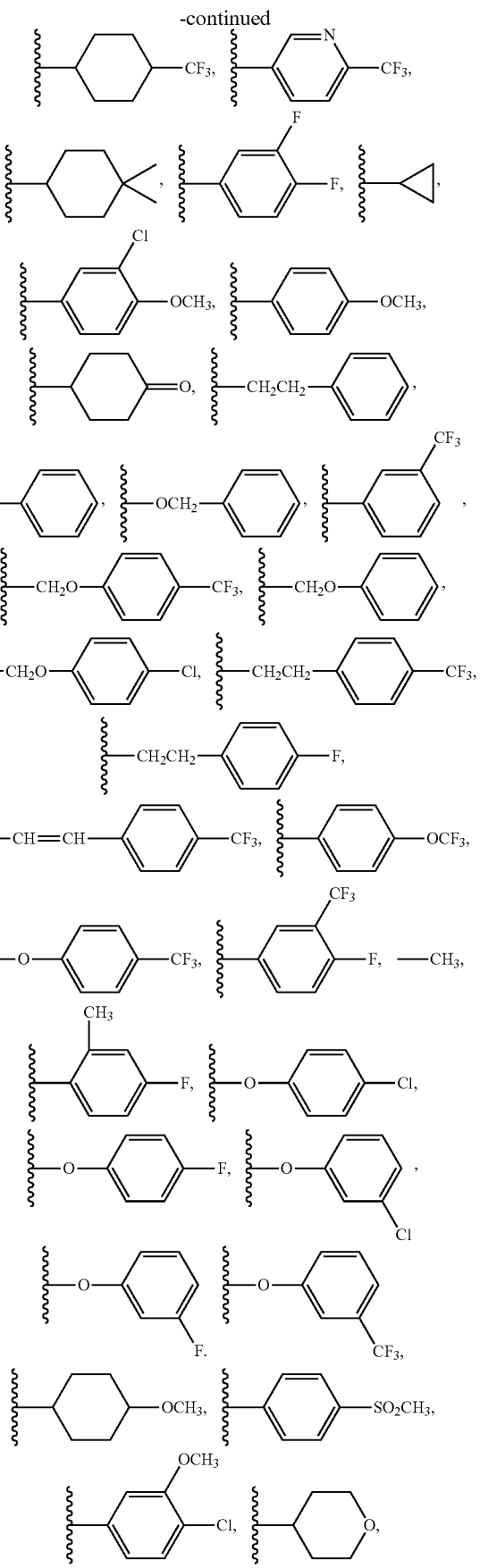

-continued

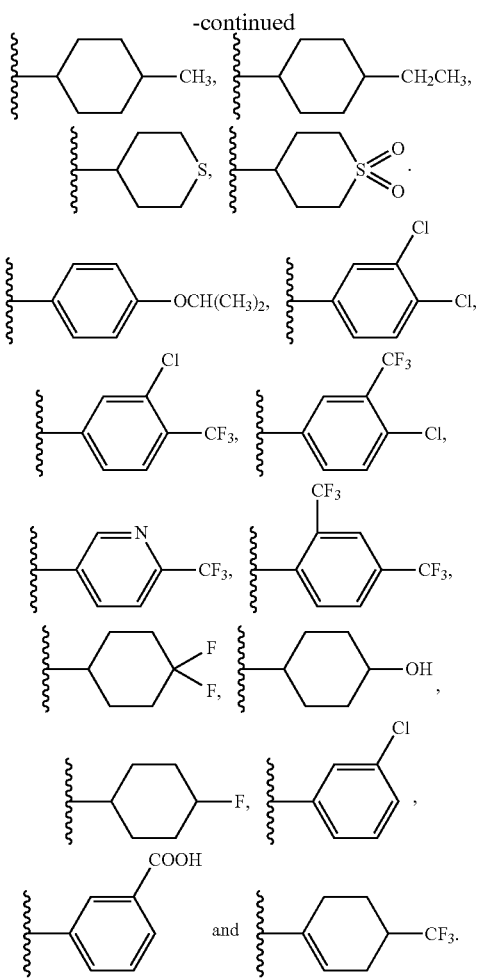

and all other variables are as previously defined.

In another embodiment, $R^5$ is selected from the group consisting of —CH$_3$, —

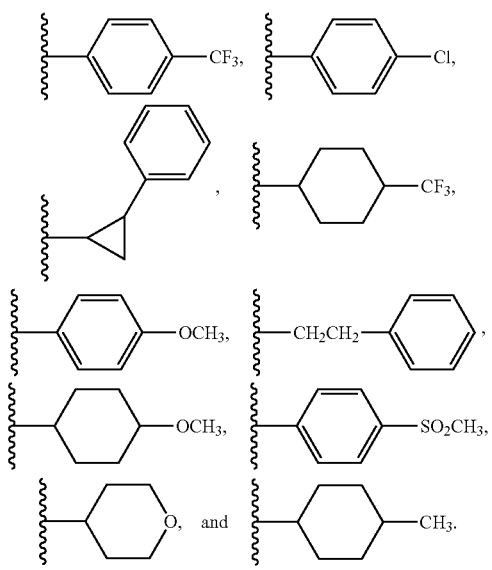

and all other variables are as previously defined.

In another embodiment, $R^8$ is selected from the group consisting of CH$_3$, Cl, F, cyclopropyl, and CF$_3$.

In another embodiment, compounds of the invention are selected from the group consisting of 1-[6-(2-{[4-(2-Phenylethyl)benzyl]oxy}phenyl)pyridin-2-yl]-5-(trifluoromethyl)-1H-pyrazole-4-carboxylic acid, 5-(Trifluoromethyl)-1-[6-(2-{[4'-(trifluoromethyl)biphenyl-4-yl]methoxy}phenyl)pyridin-2-yl]-1H-pyrazole-4-carboxylic acid, 5-(Trifluoromethyl)-1-(6-{2-[(4-{2-[4-(trifluoromethyl)phenyl]ethyl}benzyl)-oxy]phenyl}pyridin-2-yl)-1H-pyrazole-4-carboxylic acid, 1-{6-[2-({4-[(1S,2S)-2-Phenylcyclopropyl]benzyl}oxy)phenyl]pyridin-2-yl}-5-(trifluoromethyl)-1H-pyrazole-4-carboxylic acid, 1-{6-[2-({4-[(1R,2R)-2-Phenylcyclopropyl]benzyl}oxy)phenyl]pyridin-2-yl}-5-(trifluoromethyl)-1H-pyrazole-4-carboxylic acid, 1-[6-(2-{[4-(4-Chlorophenoxy)benzyl]oxy}phenyl)pyridin-2-yl]-5-(trifluoromethyl)-1H-pyrazole-4-carboxylic acid, 5-(Trifluoromethyl)-1-{6-[2-({4-[4-(trifluoromethyl)phenoxy]benzyl}oxy)phenyl]pyridin-2-yl}-1H-pyrazole-4-carboxylic acid, 5-(Trifluoromethyl)-1-(6-{2-[(4-{[4-(trifluoromethyl)phenoxy]methyl}benzyl)-oxy]phenyl}pyridin-2-yl)-1H-pyrazole-4-carboxylic acid, 1-{6-[5-Methyl-2-({4-[trans-4-(trifluoromethyl)cyclohexyl]benzyl}oxy)phenyl]pyridin-2-yl}-5-(trifluoromethyl)-1H-pyrazole-4-carboxylic acid, 1-{6-[5-Methyl-2-({4-[cis-4-(trifluoromethyl)cyclohexyl]benzyl}oxy)phenyl]pyridin-2-yl}-5-(trifluoromethyl)-1H-pyrazole-4-carboxylic acid, 1-{6-[5-Chloro-2-({4-[trans-4-(trifluoromethyl)cyclohexyl]benzyl}oxy)phenyl]pyridin-2-yl}-5-(trifluoromethyl)-1H-pyrazole-4-carboxylic acid, 1-{6-[5-Chloro-2-({4-[cis-4-(trifluoromethyl)cyclohexyl]benzyl}oxy)phenyl]pyridin-2-yl}-5-(trifluoromethyl)-1H-pyrazole-4-carboxylic acid, 1-[6-(2-{[4-(4-Oxocyclohexyl)benzyl]oxy}phenyl)pyridin-2-yl]-5-(trifluoromethyl)-1H-pyrazole-4-carboxylic acid, 1-[6-(2-{[4-(4,4-Difluorocyclohexyl)benzyl]oxy}phenyl)pyridin-2-yl]-5-(trifluoromethyl)-1H-pyrazole-4-carboxylic acid, 1-[6-(2-{[4-(trans-4-Methoxycyclohexyl)benzyl]oxy}phenyl)pyridin-2-yl]-5-(trifluoromethyl)-1H-pyrazole-4-carboxylic acid, 1-[6-(2-{[4-(cis-4-Methoxycyclohexyl)benzyl]oxy}phenyl)pyridin-2-yl]-5-(trifluoromethyl)-1H-pyrazole-4-carboxylic acid, 1-[6-(2-{[4-(trans)-4-Methoxycyclohexyl)-2-methylbenzyl]oxy}phenyl)pyridin-2-yl]-5-(trifluoromethyl)-1H-pyrazole-4-carboxylic acid, 5-(Trifluoromethyl)-1-{6-[2-({4-[6-(trifluoromethyl)pyridin-3-yl]benzyl}-oxy)phenyl]pyridin-2-yl}-1H-pyrazole-4-carboxylic acid, 1-(6-{2-[(2,4-Dimethylbenzyl)oxy]-3-methylphenyl}pyridin-2-yl)-5-(trifluoromethyl)-1H-pyrazole-4-carboxylic acid, Ethyl 1-{6-[5-chloro-2-({4-[trans-4-(trifluoromethyl)cyclohexyl]benzyl}-oxy)phenyl]pyrazin-2-yl}-5-(trifluoromethyl)-1H-pyrazole-4-carboxylate, Ethyl 1-{6-[5-chloro-2-({4-[cis-4-(trifluoromethyl)cyclohexyl]benzyl}-oxy)phenyl]pyrazin-2-yl}-5-(trifluoromethyl)-1H-pyrazole-4-carboxylate, 5-(Trifluoromethyl)-1-[4-(2-{[4'-(trifluoromethyl)biphenyl-4-yl]methoxy}phenyl)-1,3-thiazol-2-yl]-1H-pyrazole-4-carboxylic acid, 1-[2-(2-{[4-(2-Phenylethyl)benzyl]oxy}phenyl)pyrimidin-4-yl]-5-(trifluoromethyl)-1H-pyrazole-4-carboxylic acid,
1-{4-Methyl-6-[5-methyl-2-({4-[trans-4-(trifluoromethyl)cyclohexyl]benzyl}-oxy)phenyl]pyridin-2-yl}-5-(trifluoromethyl)-1H-pyrazole-4-carboxylic acid,
5-(Trifluoromethyl)-1-[6-(2-{2-[4'-(trifluoromethyl)biphenyl-4-yl]ethyl}phenyl)pyridin-2-yl]-1H-pyrazole-4-carboxylic acid,
5-(Trifluoromethyl)-1-(2'-{[4'-(trifluoromethyl)biphenyl-4-yl]methoxy}-2,3'-bipyridin-6-yl)-1H-pyrazole-4-carboxylic acid,
1-(5'-Methyl-2'-{[3-methyl-4'-(trifluoromethyl)biphenyl-4-yl]methoxy}-2,3'-bipyridin-6-yl)-5-(trifluoromethyl)-1H-pyrazole-4-carboxylic acid,
1-(5'-Chloro-2'-{[3-methyl-4'-(trifluoromethyl)biphenyl-4-yl]methoxy}-2,3'-bipyridin-6-yl)-5-(trifluoromethyl)-1H-pyrazole-4-carboxylic acid,
1-[2'-{[3-Methyl-4'-(trifluoromethyl)biphenyl-4-yl]methoxy}-5'-(trifluoromethyl)-2,3'-bipyridin-6-yl]-5-(trifluoromethyl)-1H-pyrazole-4-carboxylic acid,
5-(Trifluoromethyl)-1-{6-[2-({[4'-(trifluoromethyl)biphenyl-4-yl]oxy}methyl)phenyl]pyridin-2-yl}-1H-pyrazole-4-carboxylic acid,
5-(Trifluoromethyl)-1-(6-{2-[({5-[4-(trifluoromethyl)phenyl]pyridin-2-yl}oxy)methyl]phenyl}pyridin-2-yl)-1H-pyrazole-4-carboxylic acid,
1-{6-[5-Methyl-2-({[4'-(trifluoromethyl)biphenyl-4-yl]methyl}thio)phenyl]pyridin-2-yl}-5-(trifluoromethyl)-1H-pyrazole-4-carboxylic acid,
1-[6-(2-{Difluoro[4'-(trifluoromethyl)biphenyl-4-yl]methoxy}phenyl)pyridin-2-yl]-5-(trifluoromethyl)-1H-pyrazole-4-carboxylic acid,
1-{6-[2-(Difluoro{4-[trans-4-(trifluoromethyl)cyclohexyl]phenyl}methoxy)phenyl]pyridin-2-yl}-5-(trifluoromethyl)-1H-pyrazole-4-carboxylic acid,
1-{6-[2-(difluoro{4-[cis-4-(trifluoromethyl)cyclohexyl]phenyl}methoxy)phenyl]pyridin-2-yl}-5-(trifluoromethyl)-1H-pyrazole-4-carboxylic acid,
1-(6-{2-[{2-Ethyl-4-[4-(trifluoromethyl)cyclohexyl]phenyl}(difluoro)methoxy]phenyl}pyridin-2-yl)-5-(trifluoromethyl)-1H-pyrazole-4-carboxylic acid,
1-{6-[2-(Difluoro{[4'-(trifluoromethyl)biphenyl-4-yl]oxy}methyl)phenyl]pyridin-2-yl}-5-(trifluoromethyl)-1H-pyrazole-4-carboxylic acid, and
5-(Trifluoromethyl)-1-[6-(2-{[4'-(trifluoromethyl)biphenyl-4-yl]methoxy}phenyl)pyridin-2-yl]-1H-1,2,3-triazole-4-carboxylic acid
and pharmaceutically acceptable salts thereof.

In another embodiment, wherein $R^1$ is H, $Z^1$ is CH, $R^7$ is $CF_3$ or $CF_2H$, $D^1$ is CH, $L^1$ is O, $L^2$ is $CH_2$ or $CF_2$, ring A is

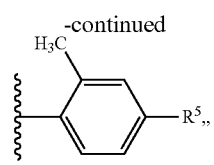,

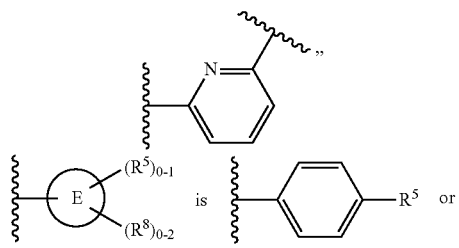 is 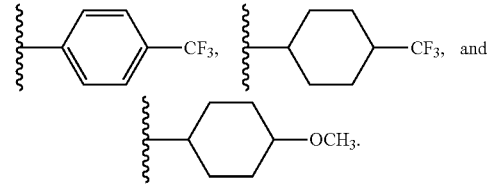 or

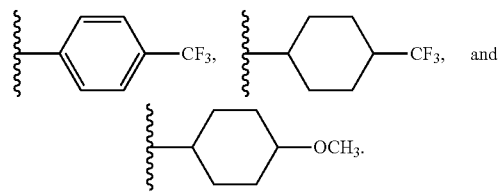

and $R^5$ is

In another embodiment, compounds of the invention are selected from the group consisting of
1-{6-[5-Methyl-2-({4-[trans-4-(trifluoromethyl)cyclohexyl]benzyl}oxy)phenyl]pyridin-2-yl}-5-(trifluoromethyl)-1H-pyrazole-4-carboxylic acid,
1-{6-[5-Methyl-2-({4-[cis-4-(trifluoromethyl)cyclohexyl]benzyl}oxy)phenyl]pyridin-2-yl}-5-(trifluoromethyl)-1H-pyrazole-4-carboxylic acid,
1-{6-[5-Chloro-2-({4-[trans-4-(trifluoromethyl)cyclohexyl]benzyl}oxy)phenyl]pyridin-2-yl}-5-(trifluoromethyl)-1H-pyrazole-4-carboxylic acid, and
1-{6-[5-Chloro-2-({4-[cis-4-(trifluoromethyl)cyclohexyl]benzyl}oxy)phenyl]pyridin-2-yl}-5-(trifluoromethyl)-1H-pyrazole-4-carboxylic acid,
and pharmaceutically acceptable salts thereof.

As used herein except where noted, "alkyl" is intended to include both branched- and straight-chain saturated aliphatic hydrocarbon groups having the specified number of carbon atoms. The term "cycloalkyl" means carbocycles containing no heteroatoms. Examples of cycloalkyl include cyclopropyl, cyclobutyl, cyclopentyl, cyclohexyl, cycloheptyl, decahydronaphthyl and the like. Commonly used abbreviations for alkyl groups are used throughout the specification, e.g. methyl may be represented by conventional abbreviations including "Me" or $CH_3$ or a symbol that is an extended bond without defined terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. The phrase "$C_{1-6}$ alkyl, wherein the alkyl group may be unsubstituted or substituted with 1-3 fluorine atoms" refers to alkyl groups having 0, 1, 2 or 3 fluorine atoms attached to one or more carbon atoms. The group "$CF_3$", for example, is a methyl group having three fluorine atoms attached the same carbon atom.

"Alkenyl" unless otherwise indicated, means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. The term "cycloalkenyl" means carbocycles containing no heteroatoms having at least one carbon-carbon double bond.

"Aryl" unless otherwise indicated, means mono- and bicyclic aromatic rings containing 6-12 carbon atoms. Examples of aryl include phenyl, naphthyl, indenyl and the like. "Aryl" also includes monocyclic rings fused to an aryl group. Examples include tetrahydronaphthyl, indanyl and the like.

"Heteroaryl" unless otherwise indicated, means a mono- or bicyclic aromatic ring or ring system containing at least one heteroatom selected from O, S and N, with each ring containing 5 to 10 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl", unless otherwise indicated, means a 5- or 6-membered monocyclic saturated ring containing at least one heteroatom selected from N, S and O, in which the point of attachment may be carbon or nitrogen. Examples of "heterocyclyl" include pyrrolidinyl, piperidinyl, piperazinyl, morpholinyl, imiciazolidinyl, 2,3-dihydrofuro(2,3-b)pyridyl, benzoxazinyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium.

"Halogen" unless otherwise indicated, includes fluorine, chlorine, bromine and iodine.

Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

In the representation of rings that define variable A.

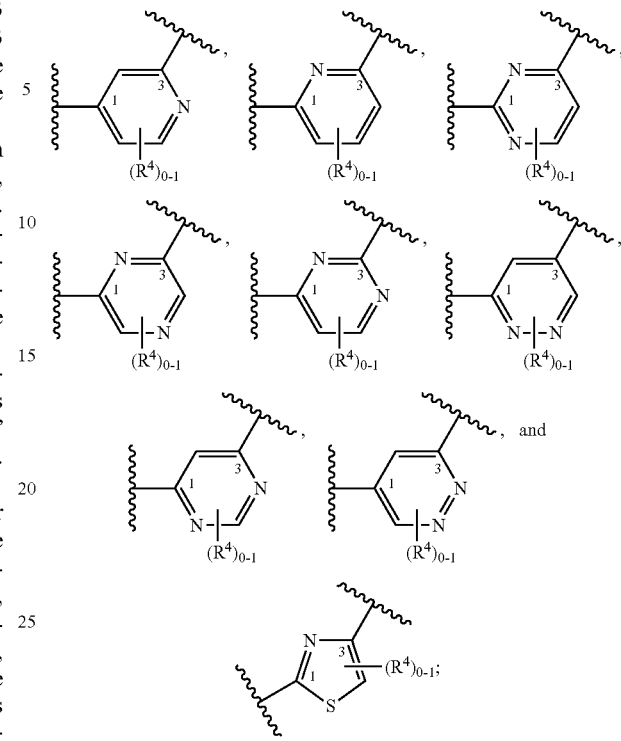

the 1,3 substitution of each ring is oriented such that the carbon atom of ring A numbered "1" is attached to the group

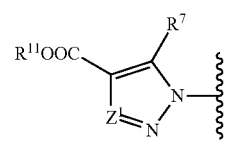

and the carbon atom of ring A numbered "3" is attached to the group

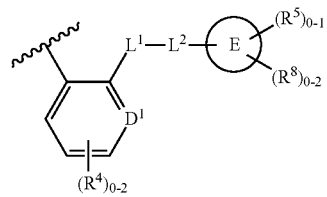

In one embodiment of A, the same 1,3 substitution pattern is followed:

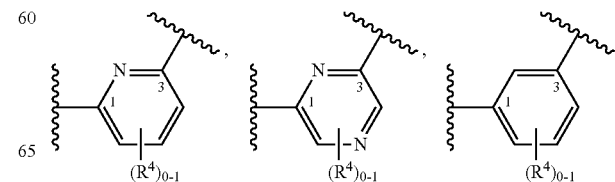
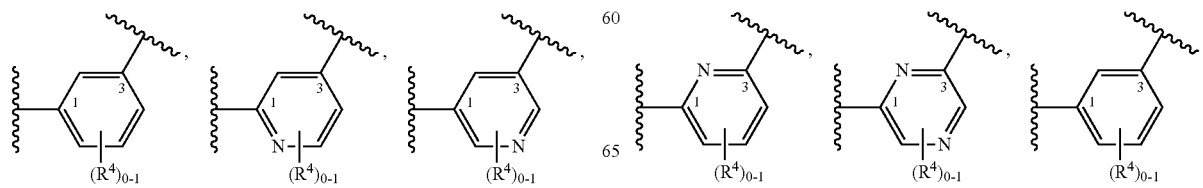

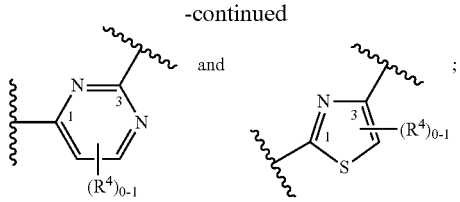

The present invention includes all stereoisomeric forms of the compounds of the formula I. Centers of asymmetry that are present in the compounds of formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula I or at the stage of an intermediate during the synthesis. The present invention also includes all tautomeric forms of the compounds of formula I.

If the compounds of the formula I contain one or more acidic or basic groups the invention also includes the corresponding physiologically or toxicologically acceptable salts, in particular the pharmaceutically utilizable salts. Thus, the compounds of the formula I which contain acidic groups can be present on these groups and can be used according to the invention, for example, as alkali metal salts, alkaline earth metal salts or as ammonium salts. Examples of such salts are sodium salts, potassium salts, calcium salts, magnesium salts or salts with ammonia or organic amines such as, for example, ethylamine, ethanolamine, triethanolamine or amino acids. Compounds of the formula I which contain one or more basic groups, i.e. groups which can be protonated, can be present and can be used according to the invention in the form of their acid addition salts with inorganic or organic acids, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of the formula I simultaneously contain acidic and basic groups in the molecule the invention also includes, in addition to the salt forms mentioned, inner salts or betaines (zwitterions). Salts can be obtained from the compounds of the formula I by customary methods which are known to the person skilled in the art, for example by combination with an organic or inorganic acid or base in a solvent or dispersant, or by anion exchange or cation exchange from other salts. The present invention also includes all salts of the compounds of the formula I which, owing to low physiological compatibility, are not directly suitable for use in pharmaceuticals but which can be used, for example, as intermediates for chemical reactions or for the preparation of physiologically acceptable salts.

The present invention also relates to processes for the preparation of the compounds of the formula I which are described in the following and by which the compounds of the invention are obtainable.

The compounds of the formula I according to the invention effect an increase of the cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of the formula I can be examined, for example, in the activity assay described below.

Disorders and pathological conditions which are associated with a low cGMP level or in which an increase of the cGMP level is desired and for whose therapy and prophylaxis it is possible to use compounds of the formula I are, for example, cardiovascular diseases, such as endothelial dysfunction, diastolic dysfunction, atherosclerosis, hypertension, stable and unstable angina pectoris, thromboses, restenoses, myocardial infarction, strokes, cardiac insufficiency or pulmonary hypertonia, or, for example, erectile dysfunction, asthma bronchiale, chronic kidney insufficiency and diabetes. Compounds of the formula I can additionally be used in the therapy of cirrhosis of the liver and also for improving a restricted memory performance or ability to learn.

The compounds of the formula I and their physiologically acceptable salts can be administered to animals, preferably to mammals, and in particular to humans, as pharmaceuticals by themselves, in mixtures with one another or in the form of pharmaceutical preparations. A subject of the present invention therefore also are the compounds of the formula I and their physiologically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

Furthermore, a subject of the present invention are pharmaceutical preparations (or pharmaceutical compositions) which comprise as active component an effective dose of at least one compound of the formula I and/or a physiologically acceptable salt thereof and a customary pharmaceutically acceptable carrier, i.e., one or more pharmaceutically acceptable carrier substances and/or additives. A subject of the present invention is also those compounds of the formula I which were already known per se and which are excluded by disclaimer from the above-defined compounds of the formula I which are per se a subject of the present invention, and their physiologically acceptable salt as activators of soluble guanylate cyclase.

Thus, a subject of the invention are, for example, said compound and its physiologically acceptable salts for use as a pharmaceutical, pharmaceutical preparations which comprise as active component an effective dose of said compound and/or a physiologically acceptable salt thereof and a customary pharmaceutically acceptable carrier, and the uses of said compound and/or a physiologically acceptable salt thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of the formula I and/or its physiologically acceptable salts in the pharmaceutical preparations normally is from 0.2 to 200 mg, preferably from 1 to 200 mg, per dose, but depending on the type of the pharmaceutical preparation it can also be higher. The pharmaceutical preparations usually comprise 0.5 to 90 percent by weight of the compounds of the formula I and/or their physiologically acceptable salts. The preparation of the pharmaceutical preparations can be carried out in a manner known per se. For this purpose, one or more compounds of the formula I and/or their physiologically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula I and their physiologically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of the formula I to be administered and/or of a physiologically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the formula I activate the soluble guanylate cyclase. On account of this property, apart from use as pharmaceutically active compounds in human medicine and veterinary medicine, they can also be employed as a scientific tool or as aid for biochemical investigations in which such an effect on guanylate cyclase is intended, and also for diagnostic purposes, for example in the in vitro diagnosis of cell samples or tissue samples. The compounds of the formula I and salts thereof can furthermore be employed, as already mentioned above, as intermediates for the preparation of other pharmaceutically active compounds.

The above-mentioned compounds are also of use in combination with other pharmacologically active compounds comprising angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losratan, valsartan, candesartan, olmesartan, telmesartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4 (S),5(S),7(S)-N-(2-carbamoyl-2-methylpropyl)-5-amino-4- hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

The compounds of formula I can be synthesized in accordance with the general schemes provided below where $Z^1$, A, $D^1$, $L^1$, $L^2$, E, $R^4$, $R^5$, $R^6$, $R^7$, $R^8$ and $R^{11}$ are defined as above, taking into account the specific examples that are provided. Throughout the synthetic schemes, abbreviations are used with the following meanings unless otherwise indicated:

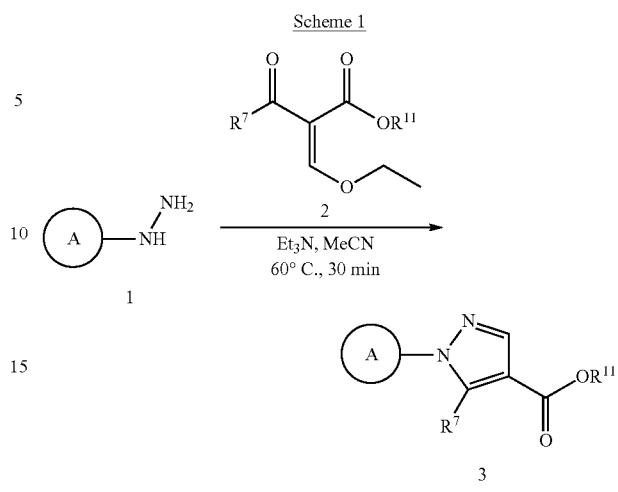

Such aryl and heteroaryl hydrazines 1 may be obtained commercially, are known in the literature and may be prepared by a variety of methods by those skilled in the art. One such synthetic method for forming 2-hydrazinopyridines 1b is shown in Scheme 2, involving reaction of a 2-chloropyri-

| | |
|---|---|
| aq, aq. = aqueous | BuLi, n-BuLi = n-butyllithium |
| Ar = aryl | DME = 1,2-dimethoxyethane |
| Ac = acetate | Bn = benzyl |
| Bu = butyl, t-Bu = tert-butyl | CBZ, Cbz = Benzyloxycarbonyl |
| cPr = cyclopropyl | conc, conc. = concentrated |
| BOC, Boc = t-butyloxycarbonyl | DAST = (diethylamino)sulfur trifluoride |
| DCM = dichloromethane | dba = dibenzylideneacetone; $Pd_2dba_3$ = tris(dibenzylidineacetone)dipalladium |
| DIEA = diisopropylethylamine | DIAD = diisopropylazodicarboxylate |
| DMAC, DMA = dimethylacetamide | DMAP = 4-dimethylaminopyridine |
| DMSO = dimethylsulfoxide | DMF = N,N-dimethylformamide |
| Et = ethyl | dppf, DPPF = 1,1'-bis(diphenylphosphino)ferrocene |
| EtOAc = ethyl acetate | DIBAL, DIBAL-H = diisobutylaluminum hydride |
| eq. = equivalent(s) | ESI = electrospray ionization |
| HOAc = acetic acid | EtOH = ethanol |
| iPr = isopropyl | HPLC = High pressure liquid chromatography |
| h, hr = hour | LAH = Lithium aluminum hydride |
| IPA, i-PrOH = isopropanol | LCMS = liquid chromatography-mass spectroscopy |
| MeOH = methanol | LHMDS = lithium bis(trimethylsilyl)amide |
| Me = methyl | min, min. = minute |
| OMs, mesyl = methanesulfonyl | Py = pyridyl |
| NMP = N-methylpyrrolidinone | Pd/C = palladium on activated carbon |
| NMR = nuclear magnetic resonance | RT, rt = room temperature |
| Ph = phenyl | sat. = saturated |
| Pr = propyl | Tosyl = toluenesulfonyl |
| THF = tetrahydrofuran | OTf, triflate = trifluoromethanesulfonate; triflic = trifluoromethanesulfonic |
| TBAI = tetrabutylammonium iodide | TLC = thin layer chromatography; prep TLC = preparative thin layer chromatography |
| TFA = Trifluoroacetic acid | Xantphos = 4,5-bis(diphenylphosphino)-9,9-dimethylxanthene |

Where $Z^1$=CH, such pyrazole acids and corresponding esters may be obtained commercially, are known in the literature, or may readily prepared by those skilled in the art. One such procedure is shown in Scheme 1, involving reaction of an aryl or heteroaryl hydrazine 1 with a β-ketoester derivative 2 in presence of a base such as $Et_3N$ and a solvent such as acetonitrile at ambient or elevated temperatures to provide pyrazole 3 (*J. Comb. Chem.* 2003, 5, 465; *Heterocycles* 1992, 34, 791).

dine derivative 4 with hydrazine hydrate in refluxing ethanol. Another method also shown in Scheme 2 involves reaction of 4 with di-tert-butylhydrazine-1,2-dicarboxylate in presence of metal catalyst such as $Pd_2dba_3$, a ligand such as dppf and a base such as $Cs_2CO_3$ in a solvent such as toluene at elevated temperatures to provide the bis-Boc-hydrazinopyridine 5, followed by deprotection in an acidic solution such as dioxane/conc. HCl to provide 2-hydrazinopyridine 1b (*Org. Lett.* 2001, 3 (9), 1351-1354).

Scheme 2

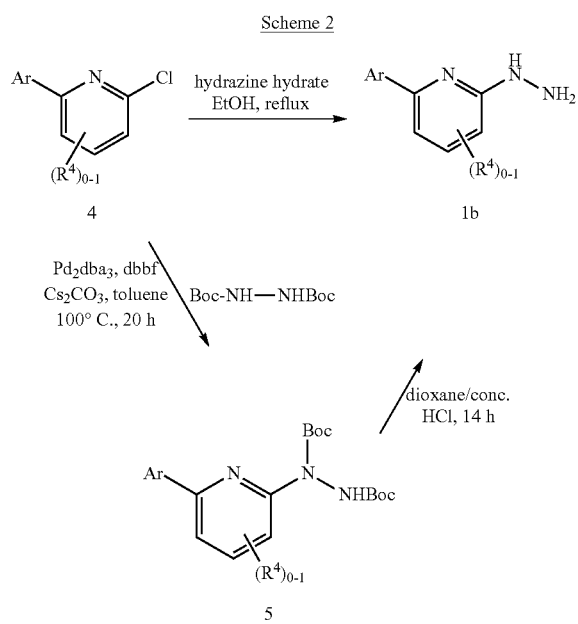

Outlined in Scheme 3, thiazolylpyrazoles 8 may readily be prepared by reaction of thiosemicarbazide with a β-ketoester 2 in a solvent such as EtOH to form the intermediate thioamidopyrazoline 6, followed by reaction with an α-bromoketone such as 7 in a solvent such as EtOH at elevated temperatures to provide the thiazolylpyrazole 8 (*J. Comb. Chem.* 2002, 4, 23).

Scheme 3

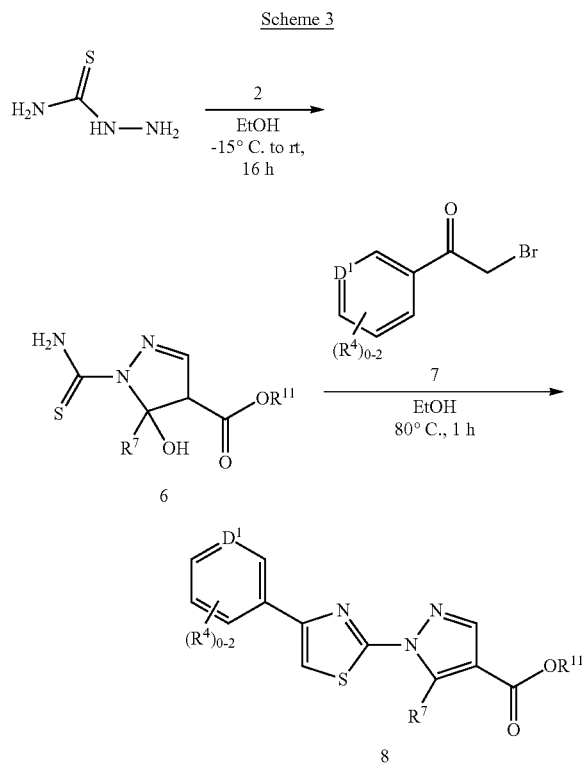

Where $Z^1$=N, such triazoles 11 may be prepared as outlined in Scheme 4, involving reaction of an aryl or heteroaryl azide 9 with a β-keto ester 10 in an appropriate solvent such as MeCN in the presence of a base such as sodium ethoxide or $Et_3N$ at elevated temperatures (*J. Med. Chem.* 1990, 33 (9), 2646; U.S. Pat. No. 4,474,599). Such azides 9 may be obtained commercially, are known in the literature and may be obtained by various methods by those skilled in the art. One such method is also shown in Scheme 4, involving reaction of hydrazine 1 with $NaNO_2$ in an appropriate acidic solvent such as a mixed solvent of diethyl ether and conc. HCl (U.S. Pat. No. 4,474,599).

Scheme 4

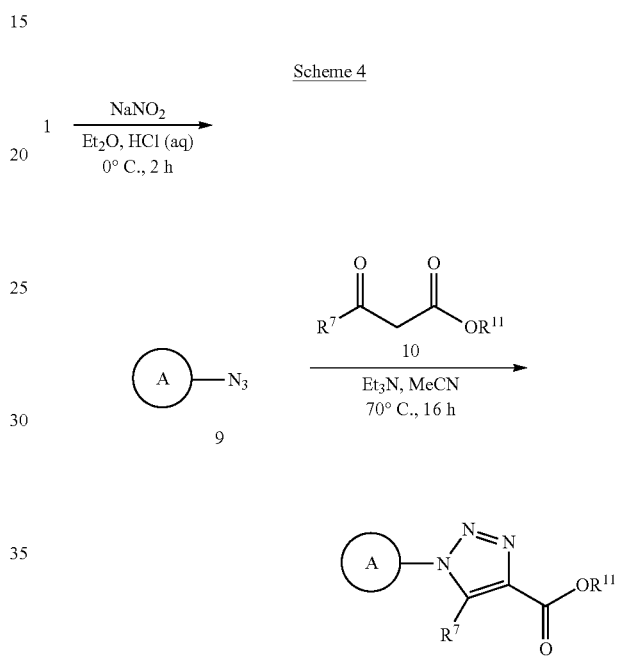

When desired, an appropriate phenyl or pyridyl ring may be attached to ring A to provide compounds 14 using various approaches by those skilled in the art. One such method is shown in Scheme 5, involving a Suzuki cross coupling reaction between an appropriately substituted intermediate 12 (Y=Cl, Br, I, OTf) and an aryl- or pyridylboronic acid 13, utilizing a catalyst such as dichloro bis(triphenylphosphine) palladium(II) and a base such as aqueous sodium carbonate in an appropriate solvent such as acetonitrile, often at elevated temperatures (*Heterocycles,* 2003, 60, 1891). Conversely, 12 (Y=Cl, Br, I) can be converted to the boronate ester 15 by reaction with bis(pinacolato)diboron using a catalyst such as $Pd(dppf)Cl_2$ in presence of a base such as potassium acetate and an appropriate solvent such as DMSO at elevated temperatures (*J. Org. Chem.* 1995, 60, 7508), or employing a catalyst such as bis(tricyclohexylphosphine)palladium(0), and a base such as sodium carbonate in a solvent such as acetonitrile (*Tetrahedron,* 2001, 57, 9813). The resultant boronate ester can then be cross-coupled to an appropriately substituted aryl or heteroaryl ring 16 (Y=Cl, Br, I, OTf) using Suzuki coupling conditions, as described above, to provide compound 14.

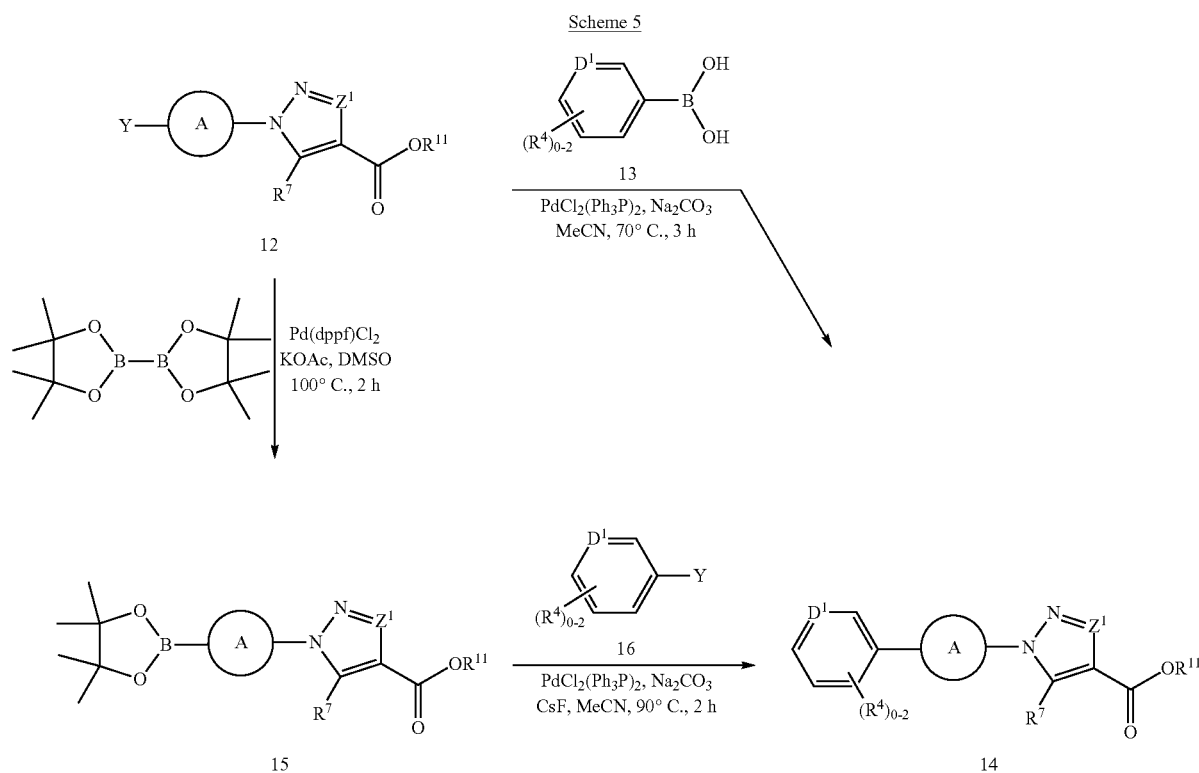

The compounds may further be elaborated by methods known to those skilled in the art. These manipulations may include, but are not limited to, substitution, reduction, oxidation, alkylation, acylation, and hydrolysis reactions. One such example for compounds wherein $L^1$=O is shown in Scheme 6, and involves alkylation of a phenol or hydroxypyridine 17 (as will be known to those skilled in the art, the hydroxypyridine can also exist in the tautomeric pyridone form, but is shown as the hydroxypyridine throughout for simplicity) with an alkyl or benzyl halide Y-$L^2$-E (Y=Cl, Br) in presence of a base such as $K_2CO_3$ or $Cs_2CO_3$, typically in a polar solvent such as DMF at ambient or slightly elevated temperatures to afford ether 18. Such ethers 18 may also be formed using Mitsunobu conditions, involving reaction of 17 with an alkyl or benzyl alcohol E-$L^2$-OH, typically in an aprotic solvent such as DCM or THF, in presence of a phosphine such as triphenylphosphine and an azodicarbonyl reagent such as diisopropyl azodicarboxylate (*Synthesis* 1981, p. 1).

-continued

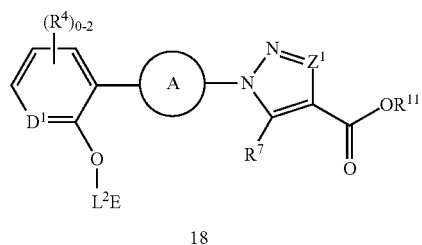

Shown in Scheme 7, when $D^1$=N, compounds 18b can also be formed by reaction of an appropriately reactive intermediate, such as, for example, fluoropyridine 19 with an alkyl or benzyl alcohol HO-$L^2$-E in the presence of a strong base such as NaOtBu in a polar solvent such as DMF.

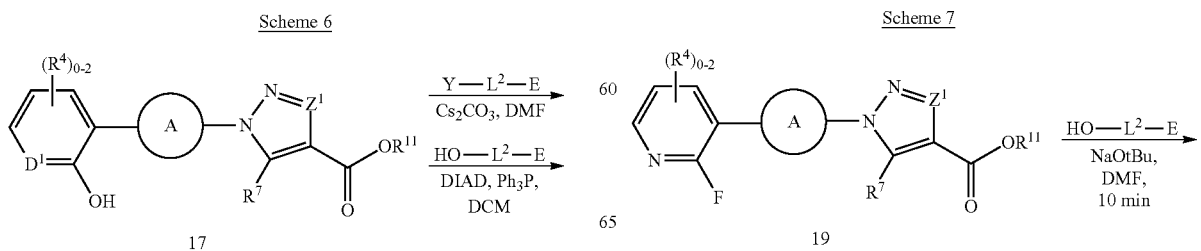

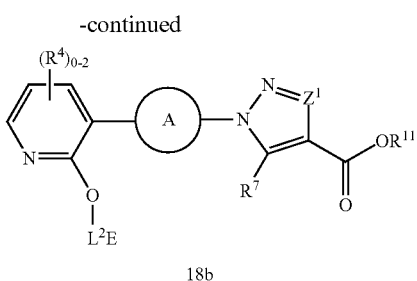

In cases where the phenyl or pyridyl ring is appropriately substituted, the compounds may be modified using cross coupling conditions. One such example shown in Scheme 8, in which an aryl triflate 20 is reacted with the corresponding alkyne ECCH in the presence of copper (I) iodide, dichorobis(triphenylphosphine)palladium(II), tetrabutylammonium iodide and $Et_3N$ in acetonitrile at ambient temperature to afford the alkyne 21 (*Tetrahedron Lett.* 2001, p. 5275). Reduction of the triple bond by hydrogenation using a metal catalyst such as $PtO_2$ in a solvent such as EtOAc under a hydrogen atmosphere provides ethylene derivative 22.

Compounds wherein $L^1=S$ can also be obtained from triflate 20 as shown in Scheme 9. Reaction with 4-methoxy α-toluenethiol in presence of a metal catalyst such as $Pd_2dba_3$, a ligand such as Xantphos and a base such as DIEA in an appropriate solvent such as dioxane at elevated temperatures for 15 h provides the methoxybenzyl thioether 23 (*Organic Letters* 2004, 6 (24), 4587). Removal of the benzyl group in an acidic solvent such as TFA in presence of a trapping agent such as anisole provides the thiol 24, which is sometimes accompanied by the corresponding disulfide dimer. Alkylation with the desired alkyl or benzyl halide $Y-L^2-E$ (Y=Cl, Br) in presence of a base such as or $Cs_2CO_3$, typically in a polar solvent such as DMF, provides the thioether 25. In instances where disulfide is present, addition of a reductant such as $NaBH_4$ to the reaction can aid in improving the product yield by converting the disulfide to the thiol in situ.

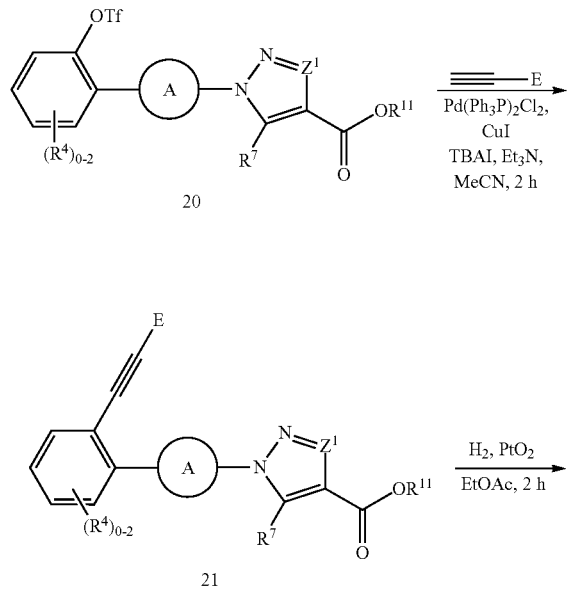

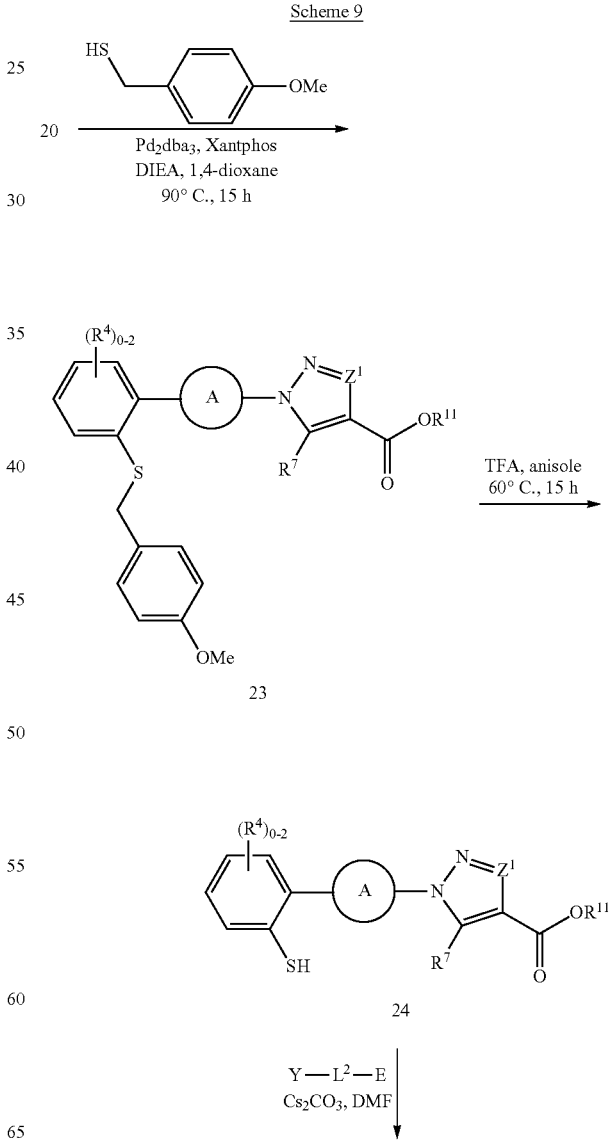

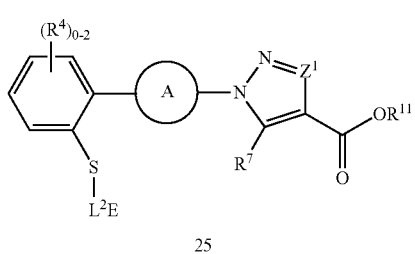

25

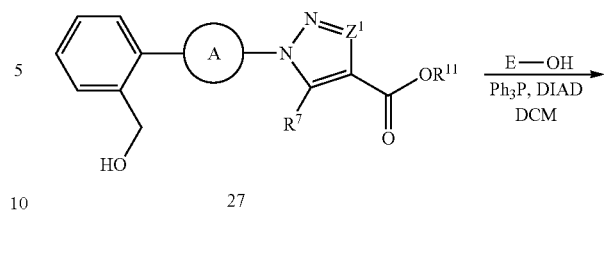

27

One method for obtaining compounds wherein $L^1$=CH$_2$ and $L^2$=O is shown in Scheme 10, involving the Suzuki cross-coupling of an appropriately substituted compound 12 (Y=I, Br, Cl, OTf) with an appropriate boronate such as 26 to provide the hydroxymethyl analog 27. Such compounds can be further modified if desired, for example, by reaction with aromatic and heteroaromatic species E-OH using Mitsunobu coupling conditions as described above (vide supra) to provide compounds 28.

28

In some instances, further modification of the compounds thus described may be desired. One such example is shown in Scheme 11, whereby treatment with of compound 17 with a chlorinating agent such as benzyltrimethylammonium tetrachloroiodate in DCM at ambient temperature for 24 h provides predominantly the para-chloro derivative 29. Conversely, also shown in Scheme 11, treatment of 17 with iodine and silver sulfate in a solvent such as EtOH affords a mixture of the para-iodo compound 30 and the ortho-iodo isomer 31. If desired, the iodine may be further modified by a variety of methods by those skilled in the art. These transformations include, but are not limited to, cross-coupling reactions, cyanation reactions, halogen exchange reactions and carbonylation reactions. The phenol group may then be further modified as described above (vide supra).

Scheme 10

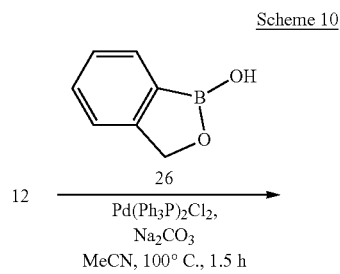

Scheme 11

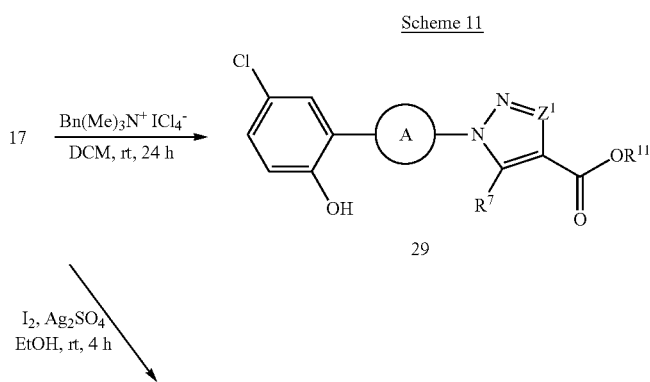

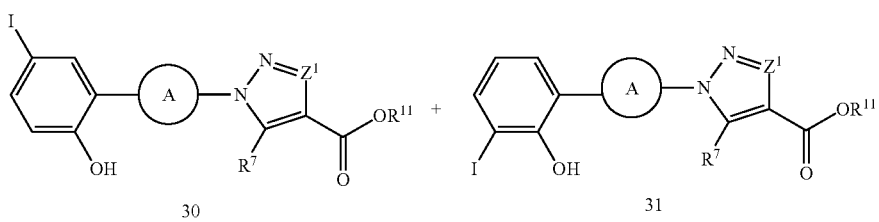

In some instances further modification of ring E may be desired. An example of such a transformation is depicted in Scheme 12, wherein ring E of compound 32 is an aryl or heteroaryl ring. Such compounds may be alkylated with RY (R=alkyl, benzyl; Y=Br, Cl, I, OMs, OTosyl) under basic conditions, or with ROH (R=alkyl, benzyl) using Mitsunobu coupling conditions to provide ether 33, as described previously (vide supra).

Scheme 12

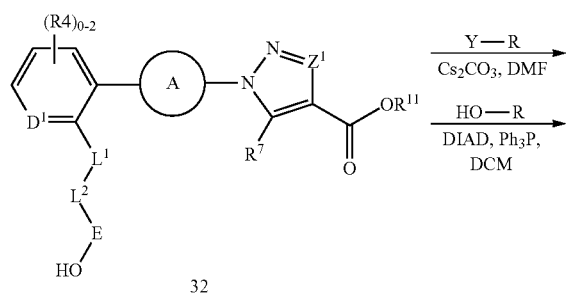

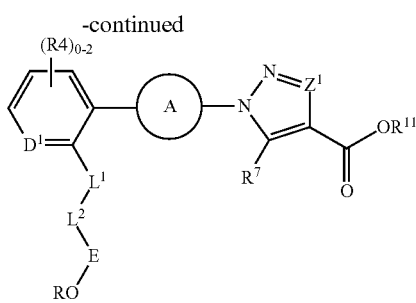

The E ring may also be modified via cross coupling reactions. For example, as shown in Scheme 13, when E is an aromatic or heteroaromatic ring, compounds 34 (Y=Br, Cl, I, OTf) may be coupled to alkyl, alkenyl, heteroaryl and aryl boronic acids $R^5$—$B(OH)_2$ utilizing Suzuki cross-coupling conditions to provide products 35, as described above (vide supra). Aryl halides may also be coupled with heteroatomic species such as phenols using the procedures of Ullman (*Org. Lett.* 2002, p. 1623), involving reaction in presence of a catalyst such as CuCl, a ligand such as 2,2,6,6-tetramethyl-3,5-heptane dione, and a base such as $Cs_2CO_3$ in an appropriate solvent such as N-methylpyrrolidinone at elevated temperatures to provide the aryl ethers 36. Alternatively, compounds 34 (Y=Br, I) may be converted to the corresponding boronate esters 37, then cross coupled to an appropriate $R^5$—Y (Y=Cl, Br, I, OTf) under Suzuki coupling conditions, as described previously, to provide compounds 35 (vide supra).

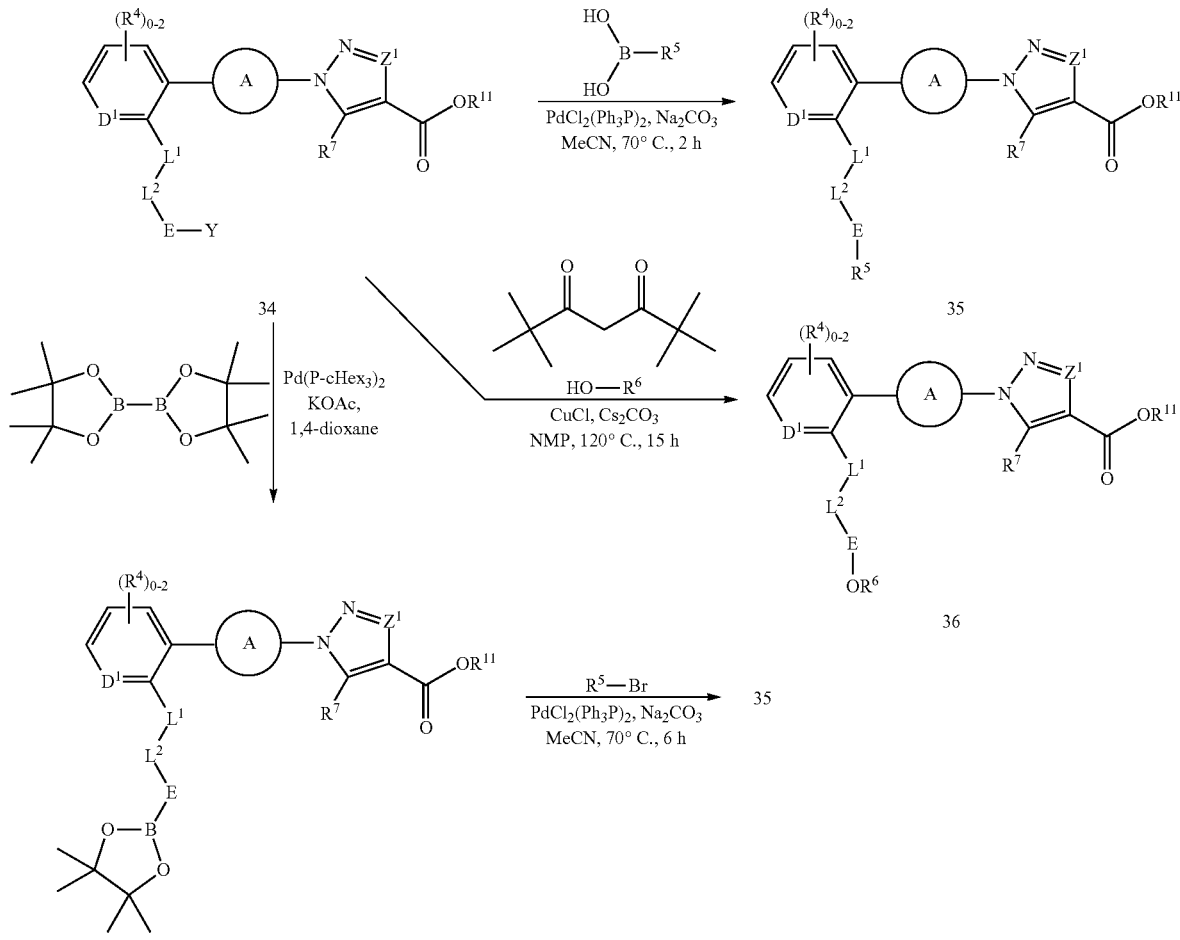

As will be understood by those skilled in the art, the compounds thus described may be further modified by a variety of chemical reactions including, but not limited to, substitution, reduction, oxidation, alkylation, acylation, cross-coupling and hydrolysis reactions.

Shown in Scheme 14, when $R^{11}$ is an alkyl group, such pyrazole and triazole esters 38a, as well as synthetic intermediates, may readily be converted to the corresponding carboxylic acids using methods known to those skilled in the art. For example, saponification of esters 38a may be achieved using a base such as aqueous lithium- or sodium hydroxide in a polar solvent such as tetrahydrofuran, dioxane, methanol, ethanol or a mixture of similar solvents to provide the corresponding carboxylic acids 38b. In addition, when $R^{11}$ is a tert-butyl group, such esters may be conveniently converted to the carboxylic acids 38b by treatment with an acid such as trifluoroacetic acid, commonly as a 1:1 mixture with methylene chloride, for 0.5 to 8 h at ambient temperature.

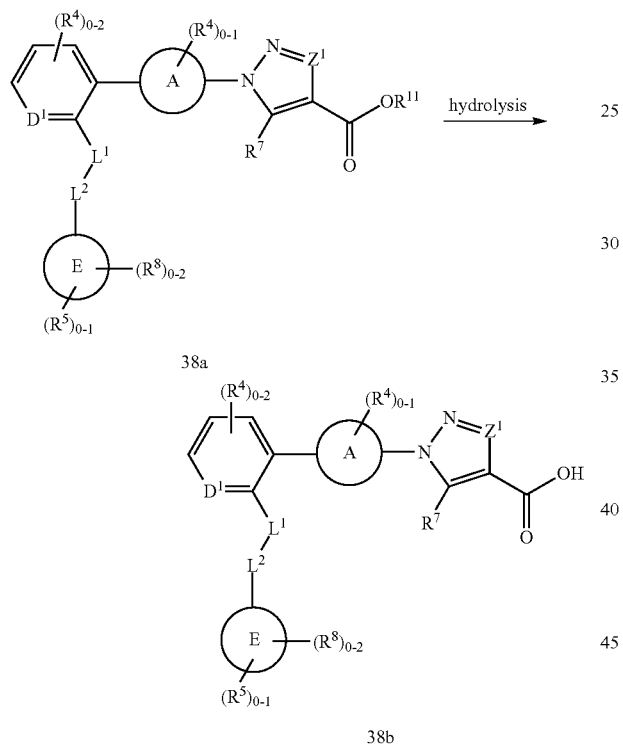

As will be known to those skilled in the art, in all schemes, the product I and all synthetic intermediates may be purified from unwanted side products, reagents and solvents by recrystallization, trituration, preparative thin layer chromatography, flash chromatography on silica gel as described by W. C. Still et al, *J. Org. Chem.* 1978, 43, 2923, or reverse-phase HPLC. Compounds purified by HPLC may be isolated as the corresponding salt.

Additionally, in some instances final compound I and synthetic intermediates may be comprised of a mixture of cis and trans isomers, enantiomers or diastereomers. As will be known to those skilled in the art, such cis and trans isomers, enantiomers and diastereomers may be separated by various methods including crystallization, chromatography using a homochiral stationary phase and, in the case of cis/trans isomers and diastereomers, normal-phase and reverse-phase chromatography.

The following examples of compounds of the formula I and of intermediates for their preparation illustrate the invention without limiting it.

Chemical reactions were monitored by LCMS, and the purity and identity of the reaction products were assayed by LCMS (electrospray ionization) and NMR. $^1$H NMR spectra are internally referenced to residual protio solvent signals. Data for $^1$H NMR are reported with chemical shift (δ ppm), multiplicity (s=singlet, d=doublet, t=triplet, q=quartet, m=multiplet), coupling constant (Hz), and integration.

Preparative HPLC was performed on either a YMC-Pack Pro C18 column (150×20 mm i.d.) or a Kromasil 100-10C8 column (100×30 mm i.d.) at an initial flow rate of 4 mL/min for 1.35 min, followed by 20 mL/min for 13.6 min. The gradients employed during the faster part of the run are described, and all runs were followed with 100% organic at 20 mL/min for 0.5 min.

Reactions with a sunlamp used a Fisher 120V, 3 A lamp with a 250 W bulb.

Flash chromatography on silica gel was performed using pre-packed silica gel columns on Biotage Horizon or Biotage SP-1 instruments equipped with UV detectors.

The following examples are provided so that the invention might be more fully understood. They should not be construed as limiting the invention in any way.

Example 1

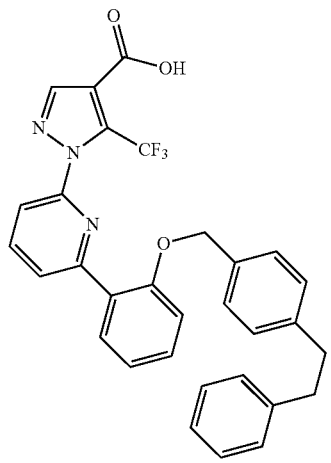 [SMILES: O=C(O)c1cnn(-c2cccc(-c3ccccc3OCc3ccc(CCc4ccccc4)cc3)n2)c1C(F)(F)F]

Step A. Ethyl-1-(6-chloropyridin-2-yl)-5-trifluoromethyl-1H-pyrazole-4-carboxylate To a solution 2-chloro-6-hydrazinopyridine (1.00 g, 6.97 mmol) and triethylamine (0.971 mL, 6.97 mmol) in acetonitrile (35 mL) was added ethyl 2-(ethoxymethylene)-4,4,4-trifluoro-3-oxobutyrate (1.36 mL, 6.97 mmol). After 20 min, the reaction mixture was placed in a 60° C. oil bath. After 30 min, the reaction mixture was allowed to cool to ambient temperature, then was concentrated in vacuo. Purification by flash chromatography on silica gel (0 to 30% EtOAc in hexanes, then 30 to 100% EtOAc in hexanes) gave the title compound: LCMS m/z 319.9 [M+H]$^+$; $^1$H NMR (500 MHz, CDCl$_3$) δ 8.10 (s, 1H), 7.88 (t, J=7.5 Hz, 1H), 7.58 (d, J=8.0 Hz, 1H), 7.47 (d, J=8.0 Hz, 1H), 4.38 (q, J=7.0 Hz, 2H), 1.38 (t, J=7.0 Hz, 3H).

Step B. Ethyl 1-[6-(2-hydroxylphenyl)pyridine-2-yl]-5-trifluoromethyl-1H-pyrazole-4-carboxylate To a flask containing the title compound from the Example 1 Step A (500 mg, 1.56 mmol) were added 2-hydroxyphenylboronic acid (237 mg, 1.72 mmol) and trans-dichlorobis(triphenylphosphine)palladium (II) (112 mg, 0.16 mmol). Acetonitrile (4 mL) and sodium carbonate (3.9 mL, 1.0 M aqueous, 3.9 mmol) were added, and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 30% EtOAc in hexanes, then 30 to 100% EtOAc in hexanes) provided the title compound: LCMS m/z 378.5 [M+H]+; 1H NMR (500 MHz, CDCl3) δ 12.02 (s, 1H), 8.18 (s, 1H), 8.09-8.04 (m, 2H), 7.82 (dd, J=8.0, 1.5 Hz, 1H), 7.50 (dd, J=7.5, 1.5 Hz, 1H), 7.38-7.34 (m, 1H), 7.06-7.03 (m, 1H), 6.99-6.95 (m, 1H), 4.40 (q, J=7.0 Hz, 2H), 1.40 (t, J=7.0 Hz, 3 H).

Step C. Ethyl 1-[6-(2-{[4-(2-phenylethyl)benzyl]oxy}phenyl)pyridin-2-yl]-5-(trifluoromethyl)-1H-pyrazole-4-carboxylate A vial was charged with the title compound from Example 1 Step B (36.0 mg, 0.095 mmol), cesium carbonate (62.2 mg, 0.191 mmol), and 4-chloromethyl dibenzyl (33.0 mg, 0.143 mmol). DMF (0.5 mL) was added, and the resulting suspension was stirred vigorously. After 2 h, the reaction mixture was diluted with EtOAc and washed with brine. The organic phase was separated and concentrated in vacuo. Purification by flash chromatography on silica gel (0 to 25% EtOAc in hexanes, then 25 to 100% EtOAc in hexanes) provided the title compound: LCMS m/z 572.5 [M+H]+; 1H NMR (500 MHz, CDCl3) δ 8.16 (d, J=8.0 Hz, 1H), 8.12 (s, 1H), 7.98 (dd, J=7.5, 1.5 Hz, 1H), 7.86 (t, J=7.5 Hz, 1H), 7.53 (d, J=7.0 Hz, 1H), 7.39-7.36 (m, 1H), 7.29-7.26 (m, 4H), 7.22-7.17 (m, 5H), 7.11 (t, J=7.5 Hz, 1H), 7.07 (d, J=8.5 Hz, 1H), 5.13 (s, 2H), 4.39 (q, J=7.0 Hz, 2H), 2.93 (app s, 4H), 1.39 (t, J=7.0 Hz, 3H).

Step D. 1-[6-(2-{[4-(2-Phenylethyl)benzyl]oxy}phenyl)pyridin-2-yl]-5-(trifluoromethyl)-1H-pyrazole-4-carboxylic acid To a solution of the title compound from Example 1 Step C (27.0 mg, 0.048 mmol) in 1,4-dioxane (2 mL) was added lithium hydroxide (1.0 mL, 2.0 M aqueous, 2.0 mmol), and the resulting mixture was stirred at 60° C. After 15 min, the reaction mixture was rendered acidic by addition of aqueous hydrochloric acid, then was diluted with 1,4-dioxane and passed through a 0.45 micron syringe filter. Purification by reverse phase HPLC (30 to 100% acetonitrile in water, each with 0.1% v/v TFA) provided the title compound: LCMS m/z 544.4 [M+H]+; 1H NMR (500 MHz, d6-DMSO) δ 8.25 (s, 1H), 8.14-8.07 (m, 2H), 7.74 (d, J=7.5 Hz, 1H), 7.69 (d, J=7.5 Hz, 1H), 7.42 (t, J=7.5 Hz, 1H), 7.32 (d, J=8.0 Hz, 1H), 7.27-7.14 (m, 8H), 7.09 (t, J=8.0 Hz, 1H), 5.19 (s, 2H), 2.86 (app s, 4H).

Example 2

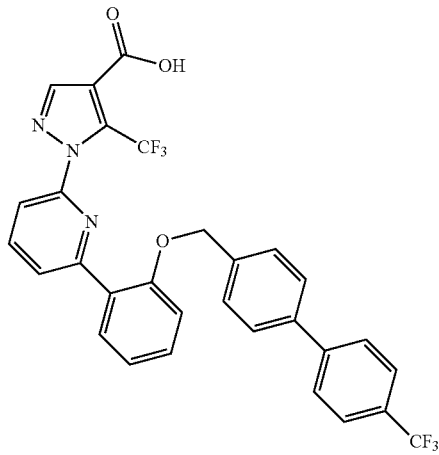

Step A. Ethyl 1-(6-{2-[(4-bromobenzyl)oxy]phenyl}pyridin-2-yl)-5-(trifluoromethyl)-1H-pyrazole-4-carboxylate To a solution of the title compound from Example 1 Step B (682 mg, 1.81 mmol) in DMF (10 mL) were added 4-bromobenzyl bromide (678 mg, 2.71 mmol) and cesium carbonate (1.77 g, 5.42 mmol). After 1.5 h, the reaction mixture was poured into sat. aq. NH4Cl and extracted with EtOAc. The organic phase was separated, dried over sodium sulfate, filtered, and concentrated in vacuo. Purification by flash chromatography on silica gel (0 to 25% EtOAc in hexanes, then 25 to 100% EtOAc in hexanes) provided the title compound: LCMS m/z 548.0 [M+H]+; 1H NMR (500 MHz, CDCl3) δ 8.13 (s, 1H), 8.08 (d, J=8.0 Hz, 1H), 7.95 (dd, J=7.5, 1.5 Hz, 1H), 7.88 (t, J=8.0 Hz, 1H), 7.54 (d, J=8.0 Hz, 1H), 7.48 (d, J=8.0 Hz, 2H), 7.39-7.36 (m, 1H), 7.23 (d, J=8.0 Hz, 2H), 7.12 (t, J=7.5 Hz, 1H), 7.03 (d, J=7.5 Hz, 1H), 5.10 (s, 2H), 4.39 (q, J=7.0 Hz, 2H), 1.39 (t, J=7.0 Hz, 3H).

Step B. Ethyl 5-(trifluoromethyl)-1-[6-(2-{[4'-(trifluoromethyl)biphenyl-4-yl]methoxy}phenyl)pyridin-2-yl]-1H-pyrazole-4-carboxylate To a flask containing the title compound from Example 2 Step A (40.0 mg, 0.073 mmol) were added 4-trifluoromethylphenyl boronic acid (21.0 mg, 0.110 mmol) and dichlorobis(triphenylphosphine)palladium(II) (2.6 mg, 0.004 mmol). Degassed acetonitrile (0.5 mL) and sodium carbonate (0.183 mL, 1.0 M aqueous, 0.183 mmol) were added, and the reaction mixture was stirred at 70° C. After 1.5 h, the reaction mixture was allowed to cool to ambient temperature, then was filtered through a short plug of silica gel, eluting with DCM. The Suzuki product was used in the subsequent step without further purification: LCMS m/z 612.2 [M+H]+.

Step C. 5-(Trifluoromethyl)-1-[6-(2-{[4'-(trifluoromethyl)biphenyl-4-yl]methoxy}phenyl)pyridin-2-yl]-1H-pyrazole-4-carboxylic acid To a solution of the title compound from Example 2 Step B (ca. 0.073 mmol) in 1,4-dioxane (0.5 mL) was added lithium hydroxide (0.50 mL, 2.0 M in water, 1.00 mmol), and the resulting mixture was stirred at 50° C. After 2 h, the reaction mixture was rendered acidic by addition of aqueous hydrochloric acid, then was diluted with 1,4-dioxane and passed through a 0.45 micron syringe filter. Purification by reverse phase HPLC (50 to 100% acetonitrile in water, each with 0.1% v/v TFA) provided the title compound: LCMS m/z 584.1 [M+H]$^+$; $^1$H NMR (500 MHz, d$_6$-DMSO) δ 8.30 (s, 1H), 8.18 (d, J=8.0 Hz, 1H), 8.14 (t, J=8.0 Hz, 1H), 7.88 (d, J=8.0 Hz, 2H), 7.80 (d, J=8.0 Hz, 2H), 7.75-7.71 (m, 4H), 7.56 (d, J=8.0 Hz, 2H), 7.46-7.43 (m, 1H), 7.30 (d, J=7.5 Hz, 1H), 7.11 (t, J=7.5 Hz, 1H), 5.32 (s, 2H).

Example 3

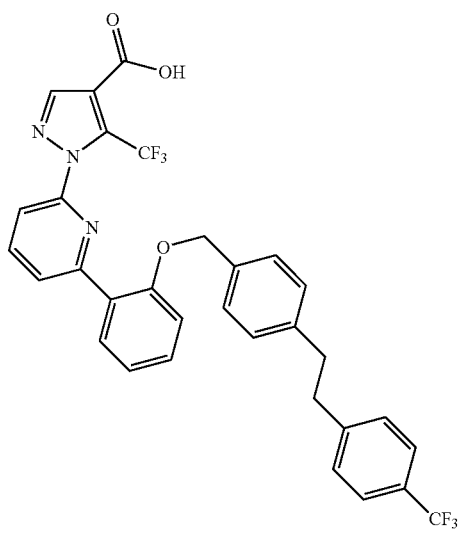 [SMILES: O=C(O)c1cnn(-c2cccc(-c3ccccc3OCc3ccc(CCc4ccc(C(F)(F)F)cc4)cc3)n2)c1C(F)(F)F]

Step A. Ethyl 5-(trifluoromethyl)-1-(6-{2-[(4-{(E)-2-[4-(trifluoromethyl)phenyl]vinyl}benzyl)oxy]phenyl}pyridin-2-yl)-1H-pyrazole-4-carboxylate To a vial containing the title compound from Example 2 Step A (50.0 mg, 0.092 mmol) were added 2-(4-trifluoromethylphenyl)vinyl boronic acid (29.6 mg, 0.137 mmol) and trans-dichlorobis(triphenylphosphine) palladium (II) (6.4 mg, 0.009 mmol). Acetonitrile (0.400 mL) and sodium carbonate (0.229 mL, 1.0 M aqueous, 0.229 mmol) were added, and the resulting mixture was degassed via nitrogen sparge. The reaction vial was capped and placed in a pre-heated oil bath (70° C.). After 18 h, the reaction mixture was allowed to cool to ambient temperature and was poured into water. The mixture was extracted with DCM, and the organic phase was concentrated in vacuo. Purification by chromatography on silica gel (0 to 30% EtOAc in hexanes, then 30 to 100% EtOAc in hexanes) provided the title compound: LCMS m/z 638.4 [M+H]$^+$; $^1$H NMR (500 MHz, CDCl$_3$) δ 8.16 (d, J=8.0 Hz, 1H), 8.13 (s, 1H), 7.97 (d, J=7.5 Hz, 1H), 7.88 (t, J=7.5 Hz, 1H), 7.61 (br s, 4H), 7.54 (d, J=8.0 Hz, 1H), 7.52 (d, J=8.5 Hz, 2H), 7.41-7.39 (m, 1H), 7.37 (d, J=7.5 Hz, 1H), 7.21-7.06 (m, 4H), 5.18 (s, 2H), 4.38 (q, J=7.0 Hz, 2H), 1.39 (t, J=7.0 Hz, 3H).

Step B. 5-(Trifluoromethyl)-1-(6-{2-[(4-{2-[4-(trifluoromethyl)phenyl]ethyl}benzyl)oxy]phenyl}pyridin-2-yl)-1H-pyrazole-4-carboxylic acid To a degassed solution of the title compound from Example 3 Step A (24.0 mg, 0.038 mmol) in EtOAc (2 mL) was added platinum(IV) oxide (8.0 mg). The reaction mixture was fitted with a hydrogen balloon attached to a 3-way adapter. The reaction flask was then evacuated and back-filled with hydrogen. After this process was repeated three times, the reaction mixture was placed under a hydrogen atmosphere and was stirred vigorously. After 45 min, the reaction mixture was filtered through Celite, rinsing with EtOAc. The mixture was concentrated in vacuo and used without further purification: LCMS m/z 640.6 [M+H]$^+$. To a solution of the hydrogenation product in 1,4-dioxane (2 mL) was added lithium hydroxide (1.0 mL, 2.0 M in water, 2.00 mmol), and the resulting mixture was stirred at 50° C. After 30 min, the reaction mixture was rendered acidic by addition of aqueous hydrochloric acid, then was diluted with 1,4-dioxane and passed through a 0.45 micron syringe filter. Purification by reverse phase HPLC (50 to 100% acetonitrile in water, each with 0.1% v/v TFA) provided the title compound: LCMS m/z 612.5 [M+H]$^+$; $^1$H NMR (500 MHz, d$_6$-DMSO) δ 8.12 (d, J=8.0 Hz, 1H), 8.11 (s, 1H), 8.08 (t, J=8.0 Hz, 1H), 7.74 (dd, J=8.0, 1.5 Hz, 1H), 7.69 (d, J=7.5 Hz, 1H), 7.60 (d, J=8.5 Hz, 2H), 7.43 (d, J=8.5 Hz, 2H), 7.33 (d, J=8.0 Hz, 2H), 7.26 (d, J=8.5 Hz, 2H), 7.22 (d, J=8.0 Hz, 2H), 7.09 (t, J=8.5 Hz, 1H), 5.20 (s, 2H), 2.97-2.94 (m, 2H), 2.91-2.88 (m, 2H).

Example 4

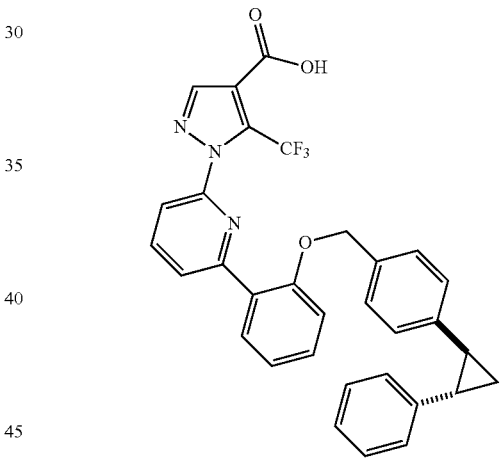

Step A. 1-{6-[2-({4-[(1S,2S)-2-Phenylcyclopropyl]benzyl}oxy)phenyl]pyridin-2-yl}-5-(trifluoromethyl)-1H-pyrazole-4-carboxylic acid and 1-{6-[2-({4-[(1R,2R)-2-phenylcyclopropyl]benzyl}oxy)phenyl]pyridin-2-yl}-5-(trifluoromethyl)-1H-pyrazole-4-carboxylic acid A vial was charged with the title compound from Example 2 Step A (600 mg, 1.10 mmol), racemic trans-2-phenylcyclopropylboronic acid (356 mg, 2.20 mmol), and tribasic potassium phosphate (769 mg, 3.62 mmol). The flask was flushed with nitrogen, then toluene (5.00 mL) and water (0.198 mL, 10.98 mmol) were added. Tetrakis(triphenylphosphine)palladium(0) (127 mg, 0.110 mmol) was added, and the reaction was capped, placed in a pre-heated oil bath (100° C.), and stirred vigorously. After 18 h, the reaction mixture was allowed to cool to ambient temperature, then was purified by flash chromatography on silica gel (0 to 20% EtOAc in hexanes, then 20 to 100% EtOAc in hexanes) to provide Suzuki product: LCMS m/z 556.2 [M+H]+. The enantiomers were separated via preparative chiral HPLC (IA column, 30% IPA in heptane, 9 mL/min flow rate: first eluting enantiomer $t_r$=15.03 min; second eluting enantiomer $t_r$=22.83 min. The enantiopure ethyl esters were saponified separately with LiOH (1.5 mL, 2.0 M aqueous, 3.0 mmol) in dioxane (4 mL) at 50° C. After 1 h, the reaction mixtures were rendered acidic by addition of 2 N HCl, then were diluted with 1,4-dioxane and DMF, and purified by reversed phase HPLC (50 to 100% acetonitrile in water, both 0.1% v/v with TFA) to provide the title compounds: LCMS m/z 544.4 [M+H]+; $^1$H NMR (500 MHz, $d_6$-DMSO) δ 8.29 (s, 1H), 8.15-8.09 (m, 2H), 7.73 (dd, J=7.5, 1.5 Hz, 1H), 7.70 (d, J=7.0 Hz, 1H), 7.44-7.40 (m, 1H), 7.33 (d, J=8.0 Hz, 2H), 7.28-7.24 (m, 3H), 7.16-7.15 (m, 5H), 5.20 (s, 2H), 2.17 (t, J=7.0 Hz, 2H), 1.46-1.43 (m, 2H).

Example 5

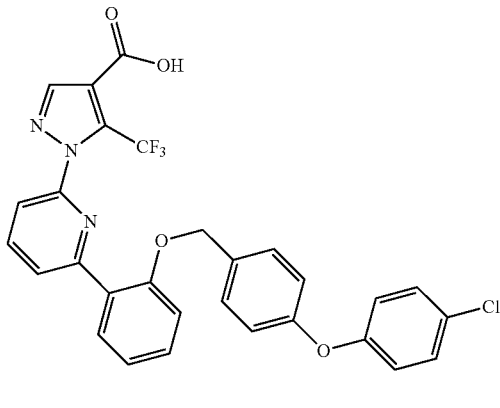 [SMILES: O=C(O)c1cnn(-c2cccc(-c3ccccc3OCc3ccc(Oc4ccc(Cl)cc4)cc3)n2)c1C(F)(F)F]

Step A. Ethyl 1-(6-{2-[(4-iodobenzyl)oxy]phenyl}pyridin-2-yl)-5-(trifluoromethyl)-1H-pyrazole-4-carboxylate To a solution of the title compound from Example 1 Step B (304 mg, 0.81 mmol) in DMF (2.7 mL) were added 4-iodobenzyl bromide (359 mg, 1.21 mmol) and cesium carbonate (788 mg, 2.42 mmol). After 12 h, the reaction mixture was poured into sat. aq. NH$_4$Cl and extracted with EtOAc. The organic phase was separated, dried over sodium sulfate, filtered, and concentrated in vacuo. Purification by flash chromatography on silica gel (0 to 25% EtOAc in hexanes, then 25 to 100% EtOAc in hexanes) provided the title compound: LCMS m/z 594.4 [M+H]+; $^1$H NMR (500 MHz, CDCl$_3$) δ 8.13 (s, 1H), 8.08 (d, J=8.0 Hz, 1H), 7.94 (dd, J=7.5, 1.5 Hz, 1H), 7.88 (t, J=8.0 Hz, 1H), 7.68 (d, J=8.0 Hz, 2H), 7.54 (d, J=8.0 Hz, 1H), 739-7.35 (m, 1H), 7.14-7.12 (m, 1H), 7.11 (d, J=8.0 Hz, 2H), 7.02 (d, J=8.0 Hz, 1H), 5.09 (s, 2H), 4.39 (q, J=7.0 Hz, 2H), 1.39 (t, J=7.0 Hz, 3H).

Step B. 1-[6-(2-{[4-(4-Chlorophenoxy)benzyl]oxy}phenyl)pyridin-2-yl]-5-(trifluoromethyl)-1H-pyrazole-4-carboxylic acid A vial was charged with copper (I) chloride (1.7 mg, 0.017 mmol), cesium carbonate (55.0 mg, 0.169 mmol), 4-chlorophenol (21.7 mg, 0.169 mmol), and the title compound from Example 5 Step A (50.0 mg, 0.084 mmol). 2,2,6,6-Tetramethyl-3,5-dione (0.007 mL, 0.034 mmol) was added and the mixture was flushed with nitrogen. Degassed N-methylpyrrolidinone (0.170 mL) was added, and the vial was capped and placed in a pre-heated oil bath (120° C.). After 15 h, the mixture was allowed to cool to ambient temperature, then was filtered through a short plug of silica gel with DCM and concentrated in vacuo: LCMS m/z 594.3 [M+H]+. To a solution of the unpurified coupling product in 1,4-dioxane (1 mL) was added lithium hydroxide (0.5 mL, 2.0 M in water, 1.00 mmol), and the resulting mixture was stirred at 50° C. After 30 min, the reaction mixture was rendered acidic by addition of aqueous hydrochloric acid, then was diluted with dioxane and passed through a 0.45 micron syringe filter. Purification by reverse phase HPLC (50 to 100% acetonitrile in water, each with 0.1% v/v TFA) provided the title compound: LCMS m/z 564.4 [M–H]−; $^1$H NMR (500 MHz, $d_6$-DMSO) δ 8.27 (s, 1H), 8.15-8.09 (m, 2H), 7.74 (dd, J=8.0, 2.0 Hz, 1H), 7.70 (dd, J=7.5, 1.0 Hz, 1H), 7.47-7.42 (m, 4H), 7.29 (d, J=8.0 Hz, 2H), 7.12-7.09 (m, 2H), 7.04-7.00 (m, 3H), 5.22 (s, 2H).

Example 6

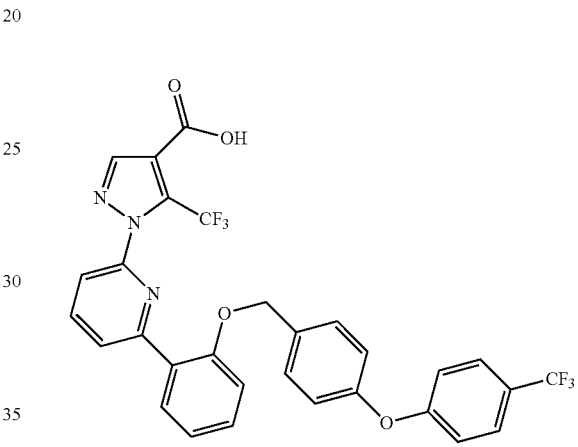

Step A. Methyl 4-[4-(trifluoromethyl)phenoxy]benzoate

A flask was charged with methyl 4-hydroxybenzoate (500 mg, 3.29 mmol), copper (II) acetate (895 mg, 4.93 mmol), 4-trifluoromethylphenylboronic acid (2.50 g, 13.15 mmol), and 4 angstrom molecular sieves (500 mg). Dichloromethane (33 mL) and triethylamine (1.83 mL, 13.15 mmol) were added, and the reaction mixture was stirred rapidly, open to air. After 48 h, the reaction mixture was filtered and concentrated in vacuo. Purification by flash chromatography on silica gel (0 to 10% EtOAc in hexanes, then 10 to 100% EtOAc in hexanes) provided the title compound: LCMS m/z 297.5 [M+H]+; $^1$H NMR (500 MHz, CDCl$_3$) δ 8.07-8.05 (m, 2H), 7.63 (d, J=8.5 Hz, 2H), 7.12 (d, J=8.5 Hz, 2H), 7.06-7.04 (m, 2H), 3.92 (s, 3H).

Step B. 4-[4-(Trifluoromethyl)phenoxy]phenyl}methanol

To a cooled (−78° C.) solution of the title compound from Example 6 Step A (325 mg, 1.10 mmol) in THF (6 mL) was added DIBAL-H (2.2 mL, 1.50 M in heptane, 3.29 mmol). After 30 min, the reaction mixture was transferred to a 0° C. bath and was held at this temperature for 45 min, whereupon it was quenched by addition of MeOH (0.5 mL). The resulting mixture was diluted with ether and saturated aqueous sodium/potassium tartrate, and the mixture was stirred vigorously until a clear phase separation was achieved. The organic phase was then separated, dried over anhydrous sodium sulfate, and concentrated in vacuo. Purification by flash chromatography on silica gel (0 to 60% EtOAc in hexanes, then 60 to 100% EtOAc in hexanes) provided the title compound: LCMS m/z 251.6 [M−OH]$^+$; $^1$H NMR (500 MHz, CDCl$_3$) δ 7.57 (d, J=9.0 Hz, 2H), 7.40 (d, J=8.0 Hz, 1H), 7.06-7.03 (m, 4H), 4.71 (s, 2H).

Step C. 5-(Trifluoromethyl)-1-{6-[2-({4-[4-(trifluoromethyl)phenoxy]benzyl}oxy)phenyl]pyridin-2-yl}-1H-pyrazole-4-carboxylic acid To a solution of the title compound from Example 1 Step B (107 mg, 0.40 mmol), the title compound from Example 6 Step B (75.0 mg, 0.20 mmol), and triphenylphosphine (104 mg, 0.40 mmol) in DCM (1 mL) was added diisopropyl azodicarboxylate (0.077 mL, 0.40 mmol) and the resulting mixture was stirred at ambient temperature. After 18 h, the reaction mixture was concentrated in vacuo. Filtration through a silica gel plug with DCM provided the title compound: LCMS m/z 628.1 [M+H]$^+$. To a solution of the Mitsunobu product in 1,4-dioxane (2 mL) was added lithium hydroxide (1.0 mL, 2.0 M aqueous, 2.00 mmol), and the resulting mixture was stirred at 50° C. After 30 min, the reaction mixture was rendered acidic by addition of aqueous hydrochloric acid, then was diluted with dioxane and passed through a 0.45 micron syringe filter. Purification by reverse phase HPLC (50 to 100% acetonitrile in water, each with 0.1% v/v TFA) provided the title compound: LCMS m/z 598.2 [M+H]$^+$; $^1$H NMR (500 MHz, d$_6$-DMSO) δ 8.28 (s, 1H), 8.16-8.10 (m, 3H), 7.75-7.70 (m, 4H), 7.51 (d, J=8.5 Hz, 2H), 7.47-7.44 (m, 1H), 7.30 (d, J=8.5 Hz, 1H), 7.15-7.10 (m, 5H), 5.25 (s, 2H).

Example 7

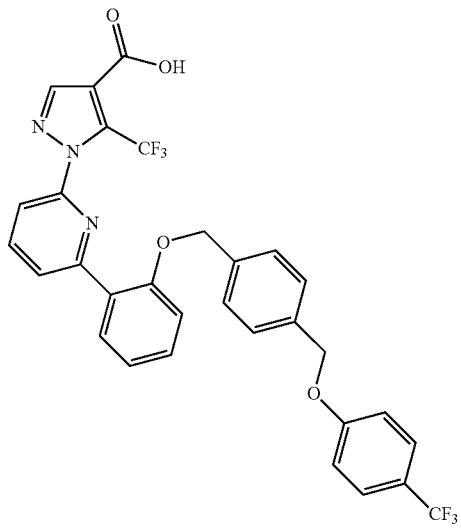 [SMILES: O=C(O)c1cnn(-c2cccc(-c3ccccc3OCc3ccc(COc4ccc(C(F)(F)F)cc4)cc3)n2)c1C(F)(F)F]

Step A. Ethyl 1-[6-(2-{[4-(hydroxymethyl)benzyl]oxy}phenyl)pyridin-2-yl]-5-(trifluoromethyl)-1H-pyrazole-4-carboxylate To a solution of the title compound of Example 1 Step B (150 mg, 0.40 mmol) and 1,4-benzenedimethanol (165 mg, 1.19 mmol) in THF (2 mL) were added triphenylphosphine (313 mg, 1.19 mmol), followed by diisopropyl azodicarboxylate (0.232 mL, 1.19 mmol). The reaction vial was capped and stirred at 60° C. After 1.5 h, the reaction mixture was allowed to cool to ambient temperature, then was concentrated in vacuo. Purification by flash chromatography on silica gel (0 to 40% EtOAc in hexanes, then 40 to 100% EtOAc in hexanes) provided the title compound: LCMS m/z 498.1 [M+H]$^+$; $^1$H NMR (500 MHz, CDCl$_3$) δ 8.13 (d, J=8.0 Hz, 1H), 8.12 (s, 1H), 7.95 (dd, J=8.0, 1.5 Hz, 1H), 7.85 (t, J=7.5 Hz, 1H), 7.51 (d, J=8.5 Hz, 1H), 7.39-7.28 (m, 5H), 7.11 (t, J=7.5 Hz, 1H), 7.06 (d, J=7.5 Hz, 1H), 5.15 (s, 2H), 4.98-4.94 (m, 2H), 4.38 (q, J=7.0 Hz, 2H), 1.39 (t, J=7.0 Hz, 3H).

Step B. Ethyl 5-(trifluoromethyl)-1-(6-{2-[(4-{[4-(trifluoromethyl)phenoxy]methyl}benzyl)oxy]phenyl}pyridin-2-yl)-1H-pyrazole-4-carboxylate To a solution of the title compound from Example 7 Step A (30.0 mg, 0.060 mmol) and 4-hydroxybenzotrifluoride (29.3 mg, 0.181 mmol) in THF (0.400 mL) were added triphenylphosphine (47.5 mg, 0.181 mmol) and diisopropyl azodicarboxylate (0.035 mL, 0.181 mmol). The resulting mixture was stirred at 60° C. After 3.5 h, the mixture was allowed to cool to ambient temperature, then was concentrated in vacuo. Purification by flash chromatography on silica gel (0 to 50% EtOAc in hexanes, then 50 to 100% EtOAc in hexanes) provided the title compound: LCMS m/z 642.3 [M+H]$^+$.

Step C. 5-(Trifluoromethyl)-1-(6-{2-[(4-{[4-(trifluoromethyl)phenoxy]methyl}benzyl)oxy]phenyl}pyridin-2-yl)-1H-pyrazole-4-carboxylic acid To a solution of the title compound from Example 7 Step B (15.0 mg, 0.023 mmol) 1,4-dioxane (0.500 mL) was added lithium hydroxide (0.5 mL, 2.0 M in water, 1.00 mmol), and the resulting mixture was stirred at 50° C. After 30 min, the reaction mixture was rendered acidic by addition of aqueous hydrochloric acid, then was diluted with 1,4-dioxane and passed through a 0.45 micron syringe filter. Purification by reverse phase HPLC (30 to 100% acetonitrile in water, each with 0.1% v/v TFA) provided the title compound: LCMS m/z 614.2 [M+H]$^+$; $^1$H NMR (500 MHz, d$_6$-DMSO) δ 8.29 (s, 1H), 8.14 (d, J=8.0 Hz, 1H), 8.10 (t, J=8.0 Hz, 1H), 7.73 (dd, J=7.5, 1.5 Hz, 1H), 7.70 (d, J=8.0 Hz, 1H), 7.65 (d, J=8.5 Hz, 2H), 7.46-7.41 (m, 5H), 7.27 (d, J=8.5 Hz, 1H), 7.18 (d, J=8.5 Hz, 2H), 7.09 (t, J=7.5 Hz, 1H), 5.25 (s, 2H), 5.18 (s, 2H).

Example 8

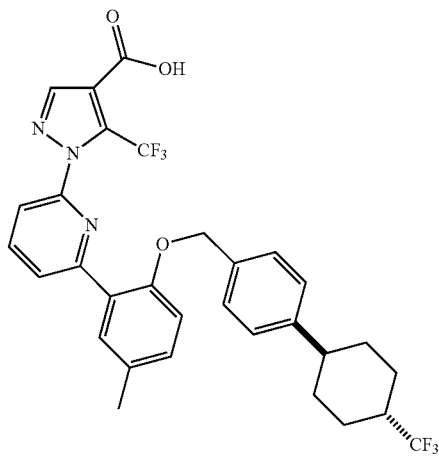

-continued

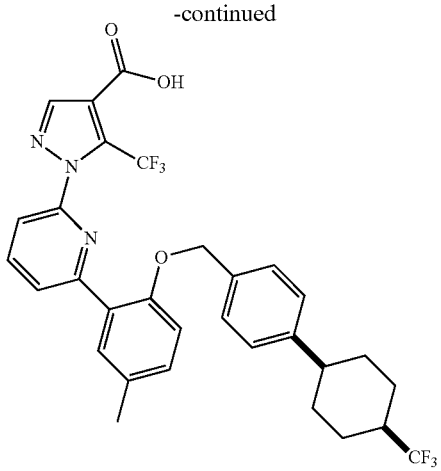

Step A. Ethyl 1-[6-(2-methoxy-5-methylphenyl)pyridin-2-yl]-5-(trifluoromethyl)-1H-pyrazole-4-carboxylate To a flask containing the title compound from Example 1 Step A (1.50 g, 4.69 mmol) were added 2-methoxy-5-methylphenyl boronic acid (0.779 g, 4.69 mmol) and trans-dichlorobis(triphenylphosphine) palladium (II) (329 mg, 0.469 mmol). Acetonitrile (12 mL) and sodium carbonate (11.7 mL, 1.0 M aqueous, 11.7 mmol) were added, and the resulting mixture was degassed via nitrogen sparge. The reaction mixture was stirred at 70° C. for 18 h, then was allowed to cool to room temperature and was poured into water. The mixture was extracted with EtOAc, and the organic phase was concentrated in vacuo. Purification by chromatography on silica gel (0 to 20% EtOAc in hexanes, then 20 to 100% EtOAc in hexanes) provided compound the title compound: LCMS m/z 406.4 [M+H]$^+$; $^1$H NMR (500 MHz, CDCl$_3$) δ 8.12 (s, 1H), 8.11 (d, J=8.0 Hz, 1H), 7.91 (t, J=8.0 Hz, 1H), 7.77 (d, J=2.0 Hz, 1H), 7.52 (d, J=8.0 Hz, 1H), 7.19 (dd, J=8.0, 2.0 Hz, 1H), 6.91 (d, J=8.0 Hz, 1H), 4.39 (q, J=7.0 Hz, 2H), 3.87 (s, 3H), 2.35 (s, 3H), 1.40 (t, J=7.0 Hz, 3H).

Step B. Ethyl 1-[6-(2-hydroxy-5-methylphenyl)pyridin-2-yl]-5-(trifluoromethyl)-1H-pyrazole-4-carboxylate To a cooled (0° C.) solution of the title compound from Example 8 Step A in DCM (20 mL) was added boron tribromide (11.7 mL, 1.0 M in DCM, 11.7 mmol). After 15 min, the reaction mixture was allowed to warm to ambient temperature. After an additional 2 h, the reaction mixture was cooled to 0° C., then was quenched by dropwise addition of sat. aq. NaHCO$_3$ (gas evolution) and was extracted with DCM. The organic phase was separated and concentrated in vacuo. Purification by flash chromatography on silica gel (0 to 30% EtOAc in hexanes, then 30 to 100% EtOAc in hexanes) provided the title compound: LCMS m/z 392.6 [M+H]$^+$; $^1$H NMR (500 MHz, CDCl$_3$) δ 11.78 (s, 1H), 8.17 (s, 1H), 8.07-8.03 (m, 2H), 7.60 (d, J=1.5 Hz, 1H), 7.48 (dd, J=7.0, 1.5 Hz, 1H), 7.17 (dd, J=8.0, 2.0 Hz, 1H), 6.94 (d, J=8.0 Hz, 1H), 4.39 (q, J=7.0 Hz, 2H), 2.36 (s, 3H), 1.40 (t, J=7.0 Hz, 3H).

Step C. Ethyl 4-[4-(trifluoromethyl)cyclohex-1-en-1-yl]benzoate

To a cooled (−78° C.) solution of 4-trifluoromethyl cyclohexanone (3.00 grams, 18.1 mmol) in anhydrous THF (100 mL) was added lithium bis(trimethylsilyl)amide (19.9 mL, 1.0 M in THF, 19.9 mmol) dropwise. After 10 min, a solution of 2-[N,N-bis(trifluoromethylsulfonyl)amino]5-chloropyridine (7.09 g, 18.1 mmol) in THF (20 mL) was added, and the resulting mixture was allowed to warm slowly to ambient temperature overnight, at which point it was quenched by pouring into sat. aq. NaHCO$_3$. The mixture was extracted with EtOAc. The organic phase was separated, dried over anhydrous sodium sulfate, and concentrated in vacuo. The resulting enol triflate was used without further purification. To a flask containing the unpurified enol triflate were added 4-ethoxycarbonylphenylboronic acid (3.68 g, 18.69 mmol) and trans-dichlorobis(triphenylphosphine) palladium (II) (633 mg, 0.903 mmol). Acetonitrile (90 mL) and sodium carbonate (45 mL, 1.0 M aqueous, 45.0 mmol) were added, and the resulting mixture was degassed via nitrogen sparge. The reaction mixture was stirred at 70° C. for 1.5 h, then was allowed to cool to room temperature and was poured into water. The mixture was extracted with EtOAc, and the organic phase was concentrated in vacuo. Purification by chromatography on silica gel (0 to 10% EtOAc in hexanes, then 10 to 100% EtOAc) provided the title compound: LCMS m/z 299.5 [M+H]$^+$; $^1$H NMR (500 MHz, CDCl$_3$) δ 7.99 (d, J=8.5 Hz, 2H), 7.42 (d, J=8.5 Hz, 2H), 6.20-6.18 (m, 1H), 4.37 (q, J=7.0 Hz, 2 H), 2.61-2.18 (m, 6H), 1.74-1.68 (m, 1H), 1.39 (t, J=7.0 Hz, 3H).

Step D. Ethyl 4-[cis-4-(trifluoromethyl)cyclohexyl]benzoate and ethyl 4-[trans-4-(trifluoromethyl)cyclohexyl]benzoate To a degassed solution of the title compound from Example 8 Step C (50.0 mg, 0.168 mmol) in i-PrOH (3 mL) was added 5% rhodium on alumina (25.0 mg). The reaction mixture was fitted with a hydrogen balloon attached to a 3-way adapter. The reaction flask was then evacuated and back-filled with hydrogen. After this process was repeated three times, the reaction mixture was placed under a hydrogen atmosphere, and was stirred vigorously. After 1 h, the reaction mixture was filtered through Celite, rinsing with EtOAc. The mixture was concentrated in vacuo, yielding a 2:1 (cis:trans) mixture of isomers. Purification by flash chromatography on silica gel (0 to 2% ether in hexanes) provided the product as mixture of isomers (1:1 cis:trans). A small portion was further purified for characterization. Analytical data for the first eluting isomer on silica gel (trans cyclohexyl): LCMS m/z 301.5 [M+H]$^+$; $^1$H NMR (500 MHz, d$_6$-DMSO) δ 7.89 (d, J=8.5 Hz, 2H), 7.38 (d, J=8.5 Hz, 2H), 4.29 (q, J=7.0 Hz, 2H), 2.67-2.61 (m, 1H), 2.39-2.33 (m, 1H), 1.97 (app d, J=13.0 Hz, 2H), 1.88 (app d, J=13.0 Hz, 2H), 1.59-1.51 (m, 2H), 1.46-1.39 (m, 2H), 1.31 (t, J=7.0 Hz, 3H). Analytical data for the second eluting isomer on silica gel (cis cyclohexyl): LCMS m/z 301.5 [M+H]$^+$; $^1$H NMR (500 MHz, d$_6$-DMSO) δ 7.90 (d, J=8.0 Hz, 2H), 7.41 (d, J=8.0 Hz, 2H), 4.30 (q, J=7.0 Hz, 2H), 2.87-2.82 (m, 1H), 2.54-2.49 (m, 1H), 1.87-1.82 (m, 2H), 1.77-1.73 (m, 6H), 1.31 (t, J=7.0 Hz, 3H).

Step E. 4-[cis-4-(Trifluoromethyl)cyclohexyl]phenyl methanol and 4-[trans-4-(trifluoromethyl)cyclohexyl]phenyl methanol To a cooled (0° C.) solution of the title compound from Example 8 Step D (2.49 g, 8.28 mmol) in THF (55 mL) was added DIBAL-H (33.1 mL, 1.0 M in toluene, 33.1 mmol). After 2 h, the reaction mixture was quenched by addition of MeOH (5.0 mL). The resulting mixture was diluted with ether and saturated aqueous sodium/potassium tartrate, and the mixture was stirred vigorously until a clear phase separation was achieved. The organic phase was then separated, dried over anhydrous sodium sulfate, and concentrated in vacuo to provide the title compound as a mixture of diastereomers (1:1 cis:trans), which was used without further purification: LCMS m/z 241.4 [M−OH]$^+$.

Step F. 1-{6-[5-Methyl-2-({4-[trans-4-(trifluoromethyl)cyclohexyl]benzyl}oxy)phenyl]pyridin-2-yl}-5-(trifluoromethyl)-1H-pyrazole-4-carboxylic acid and 1-{6-[5-methyl-2-({4-[cis-4-(trifluoromethyl)cyclohexyl]benzyl}oxy)phenyl]pyridin-2-yl}-5-(trifluoromethyl)-1H-pyrazole-4-carboxylic acid To a solution of the title compound from Example 8 Step B (150 mg, 0.383 mmol), the title compound from Example 8 Step E (148 mg, 0.575 mmol), and triphenylphosphine (151 mg, 0.575 mmol) in DCM (5 mL) was added diisopropyl azodicarboxylate (0.112 mL, 0.575 mmol), and the resulting mixture was stirred at ambient temperature. After 18 h, the reaction mixture was concentrated in vacuo. Purification by flash chromatography on silica gel (0 to 8% EtOAc in hexanes, then 8 to 100% EtOAc in hexanes) provided the title compounds. The first eluting diastereomer is the trans isomer: LCMS m/z 632.3 [M+H]$^+$. The second eluting diastereomer is the cis isomer: LCMS m/z 632.3 [M+H]$^+$. To separate solutions of the Mitsunobu products in 1,4-dioxane (2 mL) was added lithium hydroxide (1.0 mL, 2.0 M in water, 2.00 mmol), and the resulting mixtures were stirred at 50° C. After 30 min, the reaction mixtures were rendered acidic by addition of aqueous hydrochloric acid, then were diluted with 1,4-dioxane and passed through a 0.45 micron syringe filter. Purification by reverse phase HPLC (60 to 100% acetonitrile in water, each with 0.1% v/v TFA) provided the title compounds. Analytical data for the trans isomer: LCMS m/z 604.6 [M+H]$^+$; $^1$H NMR (500 MHz, d$_6$-DMSO) δ 8.29 (s, 1H), 8.15-8.08 (m, 2H), 7.69 (d, J=7.0 Hz, 1H), 7.56 (d, J=2.0 Hz, 1H), 7.32 (d, J=8.0 Hz, 2H), 7.24-7.19 (m, 2H), 7.15 (d, J=8.5 Hz, 2 H), 5.16 (s, 2H), 2.54-2.49 (m, 1H), 2.36-2.31 (m, 1H), 2.27 (s, 3H), 1.96-1.93 (m, 2H), 1.86-1.84 (m, 2H), 1.54-1.46 (m, 2H), 1.43-1.35 (m, 2H). Analytical data for the cis isomer: LCMS m/z 604.6 [M+H]$^+$; $^1$H NMR (500 MHz, d$_6$-DMSO) δ 8.27 (s, 1H), 8.14 (d, J=7.5 Hz, 1H), 8.10 (t, J=7.5 Hz, 1H), 7.69 (d, J=7.5 Hz, 1H), 7.57 (br s, 1H), 7.33 (d, J=8.0 Hz, 2H), 7.23 (d, J=8.0 Hz, 2H), 7.23-7.22 (m, 1H), 7.16 (d, J=8.5 Hz, 1H), 5.16 (s, 2H), 2.76-2.71 (m, 1H), 2.50-2.48 (m, 1H, obscured by DMSO signal), 1.82-1.78 (m, 2H), 1.74-1.71 (m, 6H).

Example 9

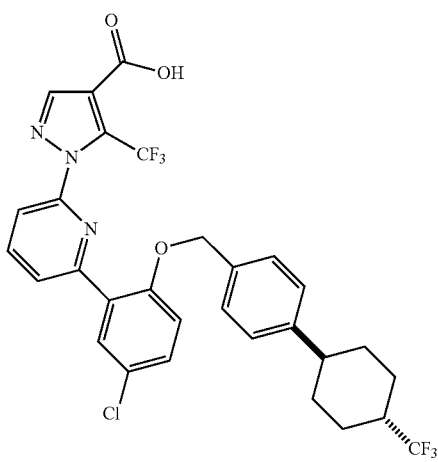

Step A. Ethyl 1-[6-(5-chloro-2-hydroxyphenyl)pyridin-2-yl]-5-(trifluoromethyl)-1H-pyrazole-4-carboxylate To a solution of the title compound from Example 1 Step B (1.00 g, 2.65 mmol) in DCM (13 mL) was added benzyltrimethylammonium tetrachloroiodate (1.13 g, 2.70 mmol) and the resulting mixture was allowed to stir at ambient temperature. After 24 h, the mixture was concentrated in vacuo. Purification by chromatography on silica gel (0 to 18% EtOAc in hexanes, then 18 to 100% EtOAc in hexanes) provided the title compound: LCMS m/z 412.0 [M+H]$^+$; $^1$H NMR (500 MHz, CDCl$_3$) δ 11.98 (s, 1H), 8.18 (s, 1H), 8.10 (t, J=8.0 Hz, 1H), 8.00 (d, J=8.0 Hz, 1H), 7.78 (br s, 1H), 7.55 (d, J=8.0 Hz, 1H), 7.30 (dd, J=9.0, 2.0 Hz, 1H), 6.98 (d, J=9.0 Hz, 1H), 4.39 (q, J=7.0 Hz, 2H), 1.40 (t, J=7.0 Hz, 3H).

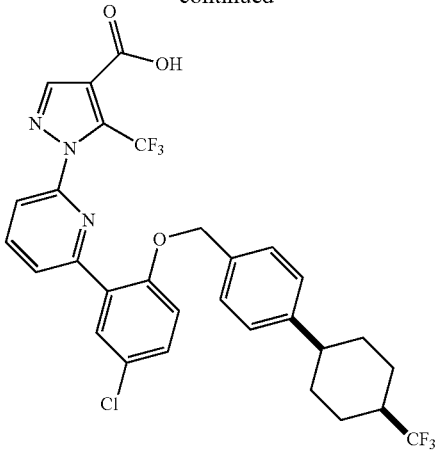

Step B. Ethyl 1-{6-[5-chloro-2-({4-[trans-4-(trifluoromethyl)cyclohexyl]benzyl}oxy)phenyl]pyridin-2-yl}-5-(trifluoromethyl)-1H-pyrazole-4-carboxylate and ethyl 1-{6-[5-chloro-2-({4-[cis-4-(trifluoromethyl)cyclohexyl]benzyl}oxy)phenyl]pyridin-2-yl}-5-(trifluoromethyl)-1H-pyrazole-4-carboxylate To a solution of the title compound from Example 9 Step A (90.0 mg, 0.219 mmol), the title compound from Example 8 Step E (85.0 mg, 0.328 mmol), and triphenylphosphine (86.0 mg, 0.328 mmol) in DCM (1 mL) was added diisopropyl azodicarboxylate (0.064 mL, 0.328 mmol), and the resulting mixture was stirred at ambient temperature. After 18 h, the reaction mixture was concentrated in vacuo. Purification by flash chromatography on silica gel (0 to 12% EtOAc in hexanes then 12 to 100% EtOAc in hexanes) provided the title compounds. The first eluting compound is the trans isomer: LCMS m/z 652.1 [M+H]$^+$; $^1$H NMR (500 MHz, CDCl$_3$) δ 8.15 (d, J=8.0 Hz, 1H), 8.13 (s, 1H), 7.97 (d, J=2.5 Hz, 1H), 7.88 (t, J=8.0 Hz, 1H), 7.57 (d, J=8.0 Hz, 1H), 7.31 (dd, J=9.0, 2.5 Hz, 1H), 7.28 (d, J=8.0 Hz, 2H), 7.19 (d, J=8.0 Hz, 2H), 6.99 (d, J=8.5 Hz, 1H), 5.12 (s, 2H), 4.39 (q, J=7.0 Hz, 2H), 2.55-2.50 (m, 1H), 2.10-2.01 (m, 5H), 1.50-1.46 (m, 4H), 1.40 (t, J=7.0 Hz, 3H). The second eluting compound is the cis isomer: LCMS m/z 652.1 [M+H]$^+$; $^1$H NMR (500 MHz, CDCl$_3$) δ 8.16 (d, J=8.0 Hz, 1H), 8.13 (s, 1H), 7.88 (t, J=8.0 Hz, 1H), 7.56 (d, J=8.0 Hz, 1H), 7.31 (dd, J=8.5, 2.5 Hz, 1H), 7.29 (d, J=8.5 Hz, 2H), 7.24 (d, J=8.5 Hz, 2 H), 7.00 (d, J=8.5 Hz, 1H), 5.12 (s, 2H), 4.39 (q, J=7.0 Hz, 2H), 2.73-2.70 (m, 1H), 2.34-2.28 (m, 1H), 1.98-1.89 (m, 4H), 1.80-1.71 (m, 4H), 1.40 (t, J=7.0 Hz, 3H).

Step C. 1-{6-[5-Chloro-2-({4-[trans-4-(trifluoromethyl)cyclohexyl]benzyl}oxy)phenyl]pyridin-2-yl}-5-(trifluoromethyl)-1H-pyrazole-4-carboxylic acid and 1-{6-[5-chloro-2-({4-[cis-4-(trifluoromethyl)cyclohexyl]benzyl}oxy)phenyl]pyridin-2-yl}-5-(trifluoromethyl)-1H-pyrazole-4-carboxylic acid To separate solutions of the title compounds from Example 9 Step B in 1,4-dioxane (1 mL) was added lithium hydroxide (0.5 mL, 2.0 M aqueous, 1.00 mmol), and the resulting mixtures were stirred at 50° C. After 30 min, the reaction mixtures were rendered acidic by addition of aqueous hydrochloric acid, then were diluted with 1,4-dioxane and passed through a 0.45 micron syringe filter. Purification by reverse phase HPLC (65 to 100% acetonitrile in water, each with 0.1% v/v TFA) provided the title compounds. Analytical data for the trans isomer: LCMS m/z 624.4 [M+H]$^+$; $^1$H NMR (500 MHz, d$_6$-DMSO) δ 8.29 (s, 1H), 8.19 (d, J=7.5 Hz, 1H), 8.14 (t, J=8.0 Hz, 1H), 7.77-7.75 (m, 2H), 7.49 (dd, J=9.0, 2.0 Hz, 1H), 7.34 (d, J=8.0 Hz, 2H), 7.31 (d, J=9.0 Hz, 1H), 7.21 (d, J=8.0 Hz, 2H), 5.22 (s, 2H), 2.52-2.48 (m, 1H, obscured by residual DMSO peak), 2.35-2.32 (m, 1H), 1.96-1.94 (m, 2H), 1.87-1.84 (m, 2H), 1.54-1.46 (m, 2H), 1.44-1.35 (m, 2H). Analytical data for the cis isomer: LCMS m/z 624.2 [M+H]$^+$; $^1$H NMR (500 MHz, d$_6$-DMSO) δ 8.29 (s, 1H), 8.20 (d, J=8.0 Hz, 1H), 8.14 (t, J=8.0 Hz, 1H), 7.78-7.75 (m, 2H), 7.48 (dd, J=9.0, 3.0 Hz, 1H), 7.35 (d, J=8.0 Hz, 2H), 7.31 (d, J=9.0 Hz, 1H), 7.25 (d, J=8.0 Hz, 2H), 5.23 (s, 2H), 2.77-2.73 (m, 1H), 2.52-2.48 (m, 1H, obscured by residual DMSO peak), 1.82-1.78 (m, 2H), 1.74-1.71 (m, 6H).

Example 10

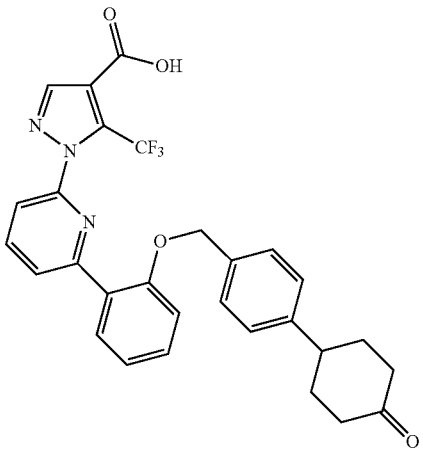 [SMILES: O=C1CCC(c2ccc(COc3ccccc3-c3cccc(-n4ncc(C(=O)O)c4C(F)(F)F)n3)cc2)CC1]

Step A. Ethyl 4-(1,4-dioxaspiro[4.5]dec-7-en-8-yl)benzoate

To a cooled (−78° C.) solution of 1,4-cyclohexanedione mono-ethylene ketal (1.00 g, 6.40 mmol) in anhydrous THF (30 mL) was added lithium bis(trimethylsilyl)amide (7.7 mL, 1.0 M in THF, 7.70 mmol) dropwise. After 10 min, a solution of 2-[N,N-bis(trifluoromethylsulfonyl)amino]5-chloropyridine (2.51 g, 6.40 mmol) in THF (10 mL) was added, and the resulting mixture was allowed to warm slowly to ambient temperature overnight, at which point it was quenched by pouring into sat. aq. NaHCO$_3$. The mixture was extracted with EtOAc. The organic phase was separated, dried over anhydrous sodium sulfate, and concentrated in vacuo. To a flask containing the unpurified enol triflate (1.36 g, 4.72 mmol) were added 4-ethoxycarbonylphenylboronic acid (1.10 g, 5.66 mmol) and trans-dichlorobis(triphenylphosphine) palladium (II) (331 mg, 0.472 mmol). Acetonitrile (24 mL) and sodium carbonate (11.8 mL, 1.0 M aqueous, 11.8 mmol) were added and the resulting mixture was degassed via nitrogen sparge. The reaction mixture was stirred at 70° C. for 3 h, then was allowed to cool to ambient temperature and was poured into water. The mixture was extracted with EtOAc, and the organic phase was concentrated in vacuo. Purification by chromatography on silica gel (0 to 30% EtOAc in hexanes, then 30 to 100% EtOAc in hexanes) provided the title compound: LCMS m/z 289.1 [M+H]$^+$; $^1$H NMR (500 MHz, CDCl$_3$) δ 7.97 (d, J=8.5 Hz, 2H), 7.44 (d, J=8.5 Hz, 2H), 6.12-6.10 (m, 1H), 4.36 (q, J=7.0 Hz, 2H), 4.03 (s, 4H), 2.70-2.67 (m, 2H), 2.50-2.48 (m, 2H), 1.93 (t, J=6.5 Hz, 2H), 1.39 (t, J=7.0 Hz, 3H).

Step B. Ethyl 4-(1,4-dioxaspiro[4.5]dec-8-yl)benzoate

A solution of the title compound from Example 10 Step A (907 mg, 3.15 mmol) in EtOAc was degassed via nitrogen sparge. Platinum(IV) oxide (225 mgs, 0.991 mmol) was then added. The reaction flask was fitted with a 3-way adapter equipped with a hydrogen balloon. After 3 vacuum/hydrogen cycles, the reaction mixture was placed under a hydrogen atmosphere. After 1 h, the reaction mixture was filtered through a pad of Celite, rinsing with EtOAc, and concentrated in vacuo. The unpurified product was used in the subsequent step: LCMS m/z 291.0 [M+H]$^+$.

Step C. [4-(1,4-Dioxaspiro[4.5]dec-8-yl)phenyl]methanol

To a cooled (−78° C.) solution of the title compound from Example 10 Step B (450 mg, 1.55 mmol) in THF (8 mL) was added DIBAL-H (3.10 mL, 1.50 M in heptane, 4.65 mmol). After 30 min, the reaction mixture was transferred to a 0° C. bath and was held at this temperature for 45 min, whereupon it was quenched by addition of MeOH (0.63 mL, 15.5 mmol). The resulting mixture was diluted with ether and saturated aqueous sodium/potassium tartrate, and the mixture was stirred rapidly until a clear phase separation was achieved. The organic phase was separated, dried over anhydrous sodium sulfate, and concentrated in vacuo. Purification by flash chromatography on silica gel (0 to 30% EtOAc in hexanes, then 30 to 100% EtOAc in hexanes) provided the title compound: LCMS m/z 231.1 [M−OH]$^+$; $^1$H NMR (500 MHz, CDCl$_3$) δ 7.29 (d, J=7.5 Hz, 2H), 7.24 (d, J=7.5 Hz, 2H), 4.65 (s, 2H), 3.98 (s, 4H), 2.59-2.54 (m, 1H), 1.87-1.66 (m, 8H).

Step D. Ethyl 1-[6-(2-{[4-(1,4-dioxaspiro[4.5]dec-8-yl)benzyl]oxy}phenyl)pyridin-2-yl]-5-(trifluoromethyl)-1H-pyrazole-4-carboxylate To a solution of the title compound from Example 1 Step B (251 mg, 0.67 mmol), the title compound from Example 10 Step C (248 mg, 1.00 mmol), and triphenylphosphine (349 mg, 1.33 mmol) in DCM (3 mL) was added diisopropyl azodicarboxylate (0.259 mL, 1.33 mmol). The resulting mixture was stirred at ambient temperature. After 5 h, the reaction mixture was concentrated in vacuo. Purification by flash chromatography on silica gel (0 to 25% EtOAc in hexanes then 25 to 100% EtOAc in hexanes) provided the title compound: LCMS m/z 608.06 [M+H]$^+$; $^1$H NMR (500 MHz, CDCl$_3$) δ 8.15 (d, J=8.0 Hz, 1H), 8.12 (s, 1H), 7.97 (d, J=8.0 Hz, 1H), 7.85 (t, J=8.0 Hz, 1H), 7.52 (d, J=7.5 Hz, 1H), 7.38-7.35 (m, 1H), 7.29 (d, J=7.5 Hz, 2H), 7.23 (d, J=7.5 Hz, 2H), 7.12-7.06 (m, 2H), 5.12 (s, 2H), 4.38 (q, J=7.0 Hz, 2H), 3.98 (s, 4H), 2.60-2.54 (m, 1H), 1.87-1.65 (m, 8H), 1.39 (t, J=7.0 Hz, 3H).

Step E. Ethyl 1-[6-(2-{[4-(4-oxocyclohexyl)benzyl]oxy}phenyl)pyridin-2-yl]-5-(trifluoromethyl)-1H-pyrazole-4-carboxylate A solution of the title compound from Example 10 Step D (300 mg, 0.49 mmol) in acetic acid (1.8 mL) and water (0.6 mL) was stirred at 80° C. After 2 h, the mixture was allowed to cool to ambient temperature, then was concentrated in vacuo. The resulting oil was diluted with ether, then was washed successively with water, saturated aqueous sodium bicarbonate, water, and brine. The organic phase was dried over anhydrous sodium sulfate, filtered, and concentrated in vacuo. Purification by flash chromatography on silica gel (0 to 20% EtOAc in hexanes, then 20 to 100% EtOAc in hexanes) provided the title compound: LCMS m/z 564.2 [M+H]$^+$; $^1$H NMR (500 MHz, CDCl$_3$) δ 8.14 (d, J=8.0 Hz, 1H), 8.12 (s, 1H), 7.96 (dd, J=8.0, 1.5 Hz, 1H), 7.87 (t, J=8.0 Hz, 1H), 7.54 (d, J=7.5 Hz, 1H), 7.40-7.36 (m, 1H), 7.32 (d, J=8.0 Hz, 2H), 7.23 (d, J=8.0 Hz, 2H), 7.12 (t, J=7.5 Hz, 1H), 7.07 (d, J=7.5 Hz, 1H), 5.14 (s, 2H), 4.38 (q, J=7.0 Hz, 2H), 3.04 (dddd, J=12.0, 12.0, 3.5, 3.5 Hz, 1H), 2.54-2.50 (m, 4H), 2.25-2.21 (m, 2H), 1.99-1.91 (m, 2H), 1.39 (t, J=7.0 Hz, 3H).

Step F. 1-[6-(2-{[4-(4-Oxocyclohexyl)benzyl]oxy}phenyl)pyridin-2-yl]-5-(trifluoromethyl)-1H-pyrazole-4-carboxylic acid To a solution of the title compound from Example 10 Step E (20.0 mg, 0.035 mmol) in 1,4-dioxane (1.0 mL) was added lithium hydroxide (0.500 mL, 2.0 M in water, 1.00 mmol), and the resulting mixture was stirred at 50° C. After 30 min, the reaction mixture was rendered acidic by addition of aqueous hydrochloric acid, then was diluted with 1,4-dioxane and passed through a 0.45 micron syringe filter. Purification by reverse phase HPLC (40 to 95% acetonitrile in water, each with 0.1% v/v TFA) provided the title compound: LCMS m/z 536.0 [M+H]$^+$; $^1$H NMR (500 MHz, d$_6$-DMSO) δ 8.30 (s, 1H), 8.14 (d, J=7.5 Hz, 1H), 8.11 (t, J=7.5 Hz, 1H), 7.73-7.70 (m, 2H), 7.43 (t, J=8.0 Hz, 1H), 7.35 (d, J=8.0 Hz, 2H), 7.29-7.26 (m, 3H), 7.09 (t, J=7.5 Hz, 1H), 5.21 (s, 2H), 3.07-3.02 (m, 1H), 2.57 (td, J=14.0, 5.5 Hz, 2H), 2.26-2.24 (m, 2H), 2.05-2.03 (m, 2H), 1.90-1.82 (m, 2H).

Example 11

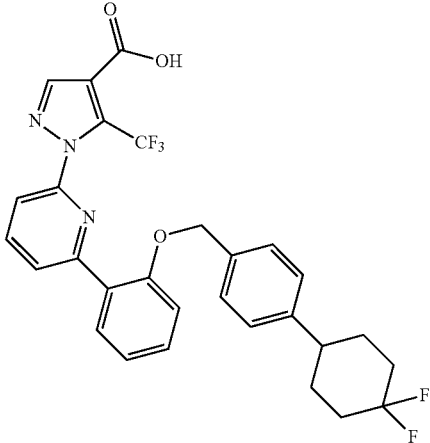 [SMILES: O=C(O)c1cnn(-c2cccc(-c3ccccc3OCc3ccc(C4CCC(F)(F)CC4)cc3)n2)c1C(F)(F)F]

Step A. Ethyl 1-[6-(2-{[4-(4,4-difluorocyclohexyl)benzyl]oxy}phenyl)pyridin-2-yl]-5-(trifluoromethyl)-1H-pyrazole-4-carboxylate A Teflon vial was charged with a solution of the title compound from Example 10 Step E (87 mg, 0.154 mmol) in DCM (0.75 mL). DAST (0.035 mL, 0.262 mmol) was added, followed by ethanol (0.002 mL, 0.03 mmol), and the resulting mixture was stirred at ambient temperature. After 4 h, the reaction mixture was quenched by addition of saturated aqueous sodium bicarbonate and was extracted with DCM. The organic phase was dried over anhydrous sodium sulfate, filtered, and concentrated in vacuo. Purification by chromatography on silica gel (0 to 25% EtOAc in hexanes, then 25 to 100% EtOAc in hexanes) provided the title compound: LCMS m/z 586.2 [M+H]$^+$.

Step B. 1-[6-(2-{[4-(4,4-Difluorocyclohexyl)benzyl]oxy}phenyl)pyridin-2-yl]-5-(trifluoromethyl)-1H-pyrazole-4-carboxylic acid To a solution of the title compound from Example 11 Step A (20.0 mg, 0.034 mmol) in 1,4-dioxane (1 mL) was added lithium hydroxide (0.500 mL, 2.0 M in water, 1.00 mmol), and the resulting mixture was stirred at 50° C. After 30 min, the reaction mixture was rendered acidic by addition of aqueous hydrochloric acid, then was diluted with 1,4-dioxane and passed through a 0.45 micron syringe filter. Purification by reverse phase HPLC (50 to 100% acetonitrile in water, each with 0.1% v/v TFA) provided the title compound: LCMS m/z 558.2 [M+H]$^+$; $^1$H NMR (500 MHz, d$_6$-DMSO) δ 8.29 (s, 1H), 8.15-8.09 (m, 2H), 7.73 (dd, J=8.0, 1.5 Hz, 1H), 7.70 (d, J=7.0 Hz, 1H), 7.42 (t, J=7.5 Hz, 1H), 7.35 (d, J=7.0 Hz, 2H), 7.27 (d, J=8.5 Hz, 1H), 7.23 (d, J=7.0 Hz, 2H), 7.09 (t, J=8.5 Hz, 1H), 5.20 (s, 2H), 2.71-2.66 (m, 1H), 2.11-2.07 (m, 2H), 2.00-1.83 (m, 4H), 1.67-1.60 (m, 2H).

Example 12

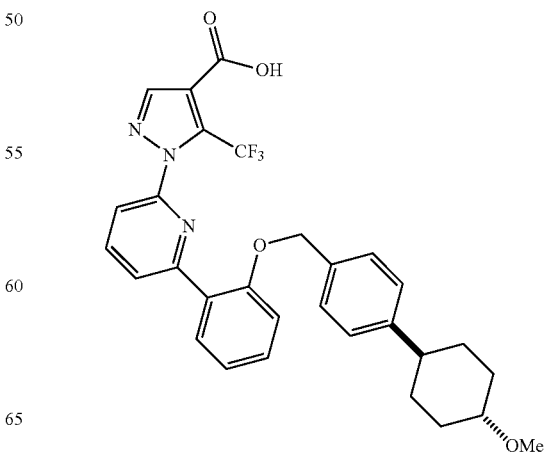

-continued

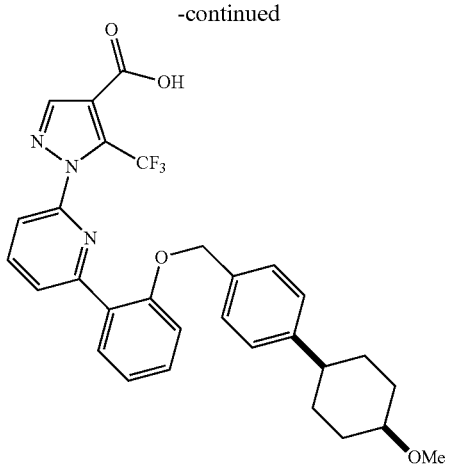

Step A. 1-[6-(2-{[4-(trans-4-Methoxycyclohexyl)benzyl]oxy}phenyl)pyridin-2-yl]-5-(trifluoromethyl)-1H-pyrazole-4-carboxylic acid and 1-[6-(2-{[4-(cis-4-methoxycyclohexyl)benzyl]oxy}phenyl)pyridin-2-yl]-5-(trifluoromethyl)-1H-pyrazole-4-carboxylic acid To a solution of the title compound from Example 10 Step E (220 mg, 0.390 mmol) in THF (2 mL) was added sodium borohydride (29.5 mg, 0.781 mmol), and the mixture was stirred at ambient temperature. After 30 min, the reaction mixture was quenched by addition of saturated aqueous ammonium chloride, then was extracted with EtOAc. The organic phase was dried over anhydrous sodium sulfate, filtered, and concentrated in vacuo. The resulting alcohol was carried forward without further purification: LCMS m/z 566.1 [M+H]$^+$. To a solution of the unpurified reduction product (64 mg, 0.113 mmol) in DCM (0.400 mL) were added 2,6-di-tert-butylpyridine (0.038 mL, 0.170 mmol) and silver trifluoromethanesulfonate (32.0 mg, 0.124 mmol). The resulting solution was cooled to 0° C., and iodomethane (0.009 mL, 0.136 mmol) was added. After 30 min, the reaction mixture was allowed to warm to ambient temperature and was held at this temperature for 1.5 h, whereupon it was filtered through Celite, rinsing with DCM. The reaction mixture was concentrated in vacuo and taken into the subsequent step without purification: LCMS m/z 580.3 [M+H]$^+$. To a solution of the crude methyl ether (ca. 66 mg, 0.113 mmol) in 1,4-dioxane (2 mL) was added lithium hydroxide (1.00 mL, 2.0 M in water, 2.00 mmol), and the resulting mixture was stirred at 50° C. After 30 min, the reaction mixture was rendered acidic by addition of aqueous hydrochloric acid, then was diluted with 1,4-dioxane and passed through a 0.45 micron syringe filter. The diastereomers (major isomer is the trans cyclohexyl) could be separated upon purification by reverse phase HPLC (40 to 90% acetonitrile in water, each with 0.1% v/v TFA) to provide the title compounds. Analytical data for the trans cyclohexyl isomer: LCMS m/z 552.2 [M+H]$^+$; $^1$H NMR (500 MHz, d$_6$-DMSO) δ 8.30 (s, 1H), 8.15-8.09 (m, 2H), 7.73-7.70 (m, 2H), 7.42 (t, J=7.5 Hz, 1H), 7.32 (d, J=8.0 Hz, 2H), 7.26 (d, J=8.0 Hz, 1H), 7.20 (d, J=8.0 Hz, 2H), 7.08 (t, J=7.5 Hz, 1H), 5.19 (s, 2H), 3.24 (s, 3H), 3.16-3.13 (m, 1H), 2.50-2.47 (m, 1H), 2.07 (d, J=10 Hz, 2H), 1.79 (d, J=12.5 Hz, 2H), 1.46-1.43 (m, 2H), 1.25-1.17 (m, 2H). Analytical data for the cis cyclohexyl isomer: LCMS m/z 552.2 [M+H]$^+$; $^1$H NMR (500 MHz, d$_6$-DMSO) δ 8.29 (s, 1H), 8.16-8.10 (m, 2H), 7.73 (dd, J=7.5, 1.5 Hz, 1H), 7.70 (d, J=7.5 Hz, 1H), 7.44-7.41 (m, 1H), 7.33 (d, J=8.0 Hz, 2H), 7.27 (d, J=8.0 Hz, 1H), 7.18 (d, J=8.0 Hz, 2H), 7.09 (t, J=7.5 Hz, 1H), 5.19 (s, 2H), 3.35 (m, 1H, obscured by residual water peak), 3.23 (s, 3H), 2.56-2.52 (m, 1H), 1.95-1.92 (m, 2H), 1.69-1.61 (m, 2H), 1.52-1.46 (m, 2H), 1.23-1.17 (m, 2H).

Example 13

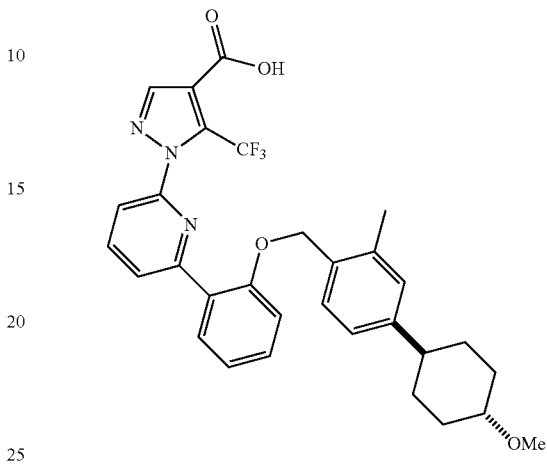

Step A. Methyl 2-methyl-4-(4,4,5,5-tetramethyl-1,3,2-dioxaborolan-2-yl)benzoate

A round bottomed flask was charged with methyl 4-bromo-2-methylbenzoate (3.98 g, 17.37 mmol), bis(pinacolato)diboron (4.85 g, 19.11 mmol), potassium acetate (5.12 g, 52.1 mmol), and dichloro[1,1'-bis(diphenylphosphino) ferrocene] palladium (II) dichloromethane adduct (0.426 g, 0.521 mmol). The flask was purged with nitrogen. Anhydrous DMSO (100 mL) was added, and the resulting suspension was degassed via nitrogen sparge. The mixture was then placed in a pre-heated oil bath (80° C.), and was held at this temperature for 2 h, whereupon it was allowed to cool to ambient temperature, then was poured into water. The aqueous phase was extracted with ether, and the organic phase was washed with brine. The organic phase was then separated, dried over anhydrous sodium sulfate, filtered, and concentrated in vacuo. Purification by flash chromatography on silica gel (0 to 10% EtOAc in hexanes, then 10 to 100% EtOAc in hexanes) provided the title compound: LCMS m/z 277.6 [M+H]$^+$; $^1$H NMR (500 MHz, CDCl$_3$) δ 7.87 (d, J=7.5 Hz, 1H), 7.68 (s, 1H), 7.66 (d, J=7.5 Hz, 1H), 3.89 (s, 3H), 2.59 (s, 3H), 1.35 (s, 12H).

Step B. Methyl 4-(1,4-dioxaspiro[4.5]dec-7-en-8-yl)-2-methylbenzoate

To a flask containing the enol triflate synthesized according to Example 10 Step A (1.10 g, 3.82 mmol) were added the title compound from Example 13 Step A (1.16 g, 4.20 mmol) and trans-dichlorobis(triphenylphosphine) palladium (II) (134 mg, 0.191 mmol). Acetonitrile (15 mL) and sodium carbonate (9.54 mL, 1.0 M aqueous, 9.54 mmol) were added, and the resulting mixture was degassed via nitrogen sparge. The reaction mixture was stirred at 70° C. for 15 h, then was allowed to cool to ambient temperature and was poured into water. The mixture was extracted with EtOAc, and the organic phase was concentrated in vacuo. Purification by chromatography on silica gel (0 to 30% EtOAc in hexanes, then 30 to 100% EtOAc in hexanes) provided the title compound: LCMS m/z 289.4 [M+H]$^+$; $^1$H NMR (500 MHz, CDCl$_3$) δ 7.87 (d, J=8.5

Hz, 1H), 7.27-7.25 (m, 2H), 6.09-6.07 (m, 1H), 4.03 (s, 4H), 3.88 (s, 3H), 2.68-2.65 (m, 2H), 2.60 (3, H), 2.49-2.47 (m, 2H), 1.94-1.91 (m, 2H).

Step C. Methyl 4-(1,4-dioxaspiro[4.5]dec-8-yl)-2-methylbenzoate

To a degassed solution of the title compound from Example 13 Step B (606 mg, 2.10 mmol) in EtOAc (15 mL) was added platinum(IV) oxide (150 mg). The reaction mixture was fitted with a 3-way adapter with a hydrogen balloon attached. The reaction flask was then evacuated and back-filled with hydrogen. After this process was repeated three times, the reaction mixture was placed under a hydrogen atmosphere, then was stirred vigorously. After 45 min, the reaction mixture was filtered through Celite, rinsing with EtOAc. The mixture was then concentrated in vacuo to provide the title compound, which was used without further purification: LCMS m/z 259.4 [M−CH$_3$O]$^+$.

Step D. Methyl 2-methyl-4-(4-oxocyclohexyl)benzoate

A solution of the title compound from Example 13 Step C (610 mg, 2.10 mmol) in acetic acid (7.8 mL) and water (2.6 mL) was stirred at 80° C. After 2 h, the mixture was allowed to cool to ambient temperature, then was concentrated in vacuo. The resulting oil was diluted with ether, then was washed successively with water, saturated aqueous sodium bicarbonate, water, and brine. The organic phase was dried over anhydrous sodium sulfate, filtered, and concentrated in vacuo. Purification by flash chromatography on silica gel (0 to 50% EtOAc in hexanes, then 50 to 100% EtOAc in hexanes) provided the title compound: LCMS m/z 215.4 [M−CH$_3$O]$^+$; $^1$H NMR (500 MHz, CDCl$_3$) δ 7.88 (d, J=8.5 Hz, 1H), 7.14-7.10°(m, 2H), 3.88 (s, 3H), 3.05-3.00 (m, 1H), 2.59 (s, 3H), 2.51 (app dd, J=8.5, 4.0 Hz, 4H), 2.24-2.20 (m, 2H), 1.97-1.92 (m, 2H).

Step E. Methyl 4-(trans-4-hydroxycyclohexyl)-2-methylbenzoate

To a solution of the title compound from Example 13 Step D (232 mg, 0.942 mmol) in THF (5.0 mL) was added sodium borohydride (71.3 mg, 1.88 mmol). After 45 min, the reaction mixture was quenched by addition of sat. aq. NH$_4$Cl. The mixture was extracted with EtOAc, and the organic phase was dried over sodium sulfate, filtered, and concentrated in vacuo to provide the title compound, which was used without further purification: LCMS m/z 249.4 [M+H]$^+$.

Step F. Methyl 4-(trans-4-methoxycyclohexyl)-2-methylbenzoate

To a solution of the title compound from Example 13 Step E (234 mg, 0.942 mmol) in DCM (4.7 mL) were added 2,6-di-tert-butylpyridine (0.318 mL, 1.41 mmol) and silver trifluoromethanesulfonate (266 mg, 1.04 mmol). The resulting solution was cooled to 0° C., and iodomethane (0.071 mL, 1.13 mmol) was added. After 30 min, the reaction mixture was allowed to warm to ambient temperature and was held at this temperature for 3 h, whereupon it was filtered through Celite, rinsing with DCM. The reaction mixture was concentrated in vacuo. Purification by flash chromatography on silica gel (0 to 30% EtOAc in hexanes, then 30 to 100% EtOAc in hexanes) provided the title compound. Analytical data for the major isomer (trans cyclohexyl): LCMS m/z 263.17 [M+H]$^+$; $^1$H NMR (500 MHz, CDCl$_3$) δ 7.85 (d, J=8.5 Hz, 1H), 7.08-7.06 (m, 2H), 3.86 (s, 3H), 3.38 (s, 3H), 3.24-3.17 (m, 1H), 2.58 (s, 3H), 2.49 (dt, J=12.0, 3.5 Hz, 1H), 2.21-2.18 (m, 2H), 1.94-1.92 (m, 2H), 1.54-1.46 (m, 2H), 1.39-1.30 (m, 2H).

Step G. [4-(trans-4-Methoxycyclohexyl)-2-methylphenyl]methanol

To a cooled (−78° C.) solution of the title compound from Example 13 Step F (90.0 mg, 0.343 mmol) in THF (1.7 mL) was added DIBAL-H (1.03 mL, 1.0 M in toluene, 1.03 mmol). After 30 min, the reaction mixture was allowed to warm to 0° C. After 2 h, the reaction mixture was quenched by addition of MeOH (0.140 mL). The resulting mixture was diluted with diethyl ether and saturated aqueous sodium/potassium tartrate, and the mixture was stirred rapidly until a clear phase separation was achieved. The organic phase was then separated, dried over anhydrous sodium sulfate, and concentrated in vacuo to provide the title compound, which was used without further purification.

Step H. Ethyl 1-[6-(2-{[4-(trans)-4-methoxycyclohexyl)-2-methylbenzyl]oxy}phenyl)pyridin-2-yl]-5-(trifluoromethyl)-1H-pyrazole-4-carboxylate The title compound was prepared by Mitsunobu coupling of the title compound from Example 13 Step G with the title compound from Example 1 Step B, using chemistry described in Example 8 Step F: LCMS m/z 594.7 [M+H]$^+$

Step I. 1-[6-(2-{[4-(trans)-4-Methoxycyclohexyl)-2-methylbenzyl]oxy}phenyl)pyridin-2-yl]-5-(trifluoromethyl)-1H-pyrazole-4-carboxylic acid The title compound was prepared by hydrolysis of the title compound from Example 13 Step H, using chemistry described in Example 1 Step D: LCMS m/z 566.7 [M+H]$^+$; $^1$H NMR (500 MHz, d$_6$-DMSO) δ 8.29 (s, 1H), 8.08 (t, J=7.5 Hz, 1H), 8.03 (d, J=7.5 Hz, 1H), 7.71-7.68 (m, 2H), 7.46-7.42 (m, 1H), 7.32 (d, J=8.0 Hz, 1H), 7.25 (d, J=7.5 Hz, 1H), 7.09 (t, J=7.5 Hz, 1H), 7.03 (s, 1H), 6.98 (d, J=8.0 Hz, 1H), 5.16 (s, 1H), 3.24 (s, 3H), 3.18-3.13 (m, 1H), 2.43-2.40 (m, 1H), 2.08-2.06 (m, 2H), 1.79-1.76 (m, 2H), 1.48-1.42 (m, 2H), 1.24-1.17 (m, 2H).

Example 14

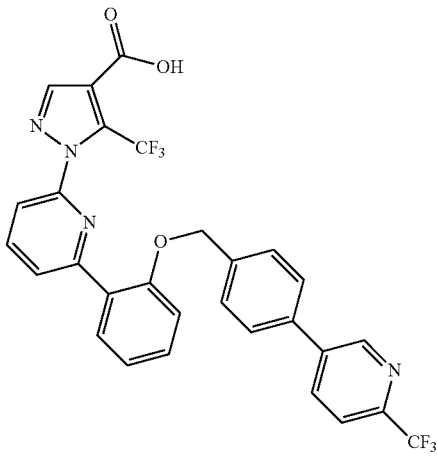

Step A. Ethyl 1-[6-(2-{[4-(4,4,5,5-tetramethyl-1,3,2-dioxaborolan-2-yl)benzyl]oxy}phenyl)pyridin-2-yl]-5-(trifluoromethyl)-1H-pyrazole-4-carboxylate A vial was charged with the product from Example 2 Step A (300 mg, 0.549 mmol), bis(pinacolato)diboron (153 mg, 0.604 mmol), bis(tricyclohexylphosphine)palladium(0) (25.0 mg, 0.037 mmol), and potassium acetate (135 mg, 1.37 mmol). The mixture was flushed with nitrogen, then degassed 1,4-dioxane (2.7 mL) was added. The vial was capped and stirred for 15 h, whereupon it was diluted with water and extracted with EtOAc. The organic phase was separated, dried over sodium sulfate, filtered, and concentrated. Purification by flash chromatography on silica gel (0 to 20% EtOAc in hexanes, then 20 to 100% EtOAc in hexanes) provided the title compound: LCMS m/z 594.8 [M+H]$^+$; $^1$H NMR (500 MHz, CDCl$_3$) δ 8.19 (d, J=8.0 Hz, 1H), 8.16 (s, 1H), 8.02 (d, J=7.0 Hz, 1H), 7.90 (t, J=8.0 Hz, 1H), 7.85 (d, J=7.0 Hz, 2H), 7.57 (d, J=8.0 Hz, 1H), 7.42 (d, J=7.0 Hz, 2H), 7.39-7.37 (m, 1H), 7.14 (t, J=7.5 Hz, 1H), 7.07 (d, J=8.0 Hz, 1H), 5.21 (s, 2H), 4.42 (q, J=7.0 Hz, 2H), 1.43 (t, J=7.0 Hz, 3H), 1.39 (s, 12H).

Step B. Ethyl 5-(trifluoromethyl)-1-{6-[2-({4-[6-(trifluoromethyl)pyridin-3-yl]benzyl}oxy)phenyl]pyridin-2-yl}-1H-pyrazole-4-carboxylate To a vial containing the title compound from Example 14 Step A (14.0 mg, 0.024 mmol) were added 3-bromo-6-trifluoromethylpyridine (6.4 mg, 0.028 mmol) and trans-dichlorobis(triphenylphosphine) palladium (II) (1.7 mg, 0.0024 mmol). Acetonitrile (0.500 mL) and sodium carbonate (0.059 mL, 1.0 M in water, 0.059 mmol) were added, and the resulting mixture was degassed by a nitrogen sparge. The reaction vial was capped and placed in a pre-heated oil bath (70° C.). After 6 h, the reaction mixture was allowed to cool to room temperature, then was purified by flash chromatography on silica gel: LCMS m/z 613.2 [M+H]$^+$.

Step C. 5-(Trifluoromethyl)-1-{6-[2-({4-[6-(trifluoromethyl)pyridin-3-yl]benzyl}oxy)phenyl]pyridin-2-yl}-1H-pyrazole-4-carboxylic acid To a solution of the title compound from Example 14 Step B in 1,4-dioxane (0.500 mL) was added lithium hydroxide (0.5 mL, 2.0 M in water, 1.00 mmol), and the resulting mixture was stirred at 50° C. After 30 min, the reaction mixture was rendered acidic by addition of aqueous hydrochloric acid, then was diluted with 1,4-dioxane and passed through a 0.45 micron syringe filter. Purification by reverse phase HPLC (50 to 100% acetonitrile in water, each with 0.1% v/v TFA) provided the title compound: LCMS m/z 585.2 [M+H]$^+$; $^1$H NMR (500 MHz, d$_6$-DMSO) δ 9.09 (d, J=2.0 Hz, 1H), 8.36 (dd, J=8.0, 2.0 Hz, 1H), 8.30 (s, 1H), 8.18 (d, J=7.0 Hz, 1H), 8.14 (t, J=8.0 Hz, 1H), 7.97 (d, J=8.0 Hz, 1H), 7.82 (d, J=8.5 Hz, 1H), 7.75 (dd, J=8.0, 2.0 Hz, 1H), 7.72 (d, J=8.0 Hz, 1H), 7.60 (d, J=8.5 Hz, 1H), 7.47-7.43 (m, 1H), 7.30 (d, J=8.0 Hz, 1H), 7.11 (t, J=7.5 Hz, 1H), 5.34 (s, 2H).

Example 15

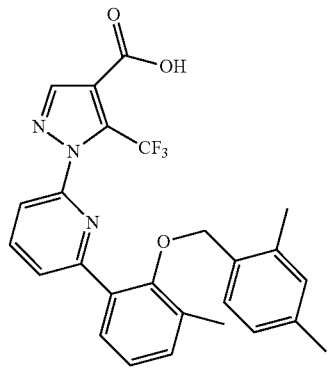 [SMILES: Cc1ccc(COc2c(C)cccc2-c2cccc(-n3ncc(C(=O)O)c3C(F)(F)F)n2)c(C)c1]

Step A. Ethyl 1-[6-(2-hydroxy-3-iodophenyl)pyridin-2-yl]-5-(trifluoromethyl)-1H-pyrazole-4-carboxylate To a suspension of the title compound from Example 1 Step B (2.00 g, 5.30 mmol) and silver sulfate (1.653 g, 5.30 mmol) in EtOH (53 mL) was added iodine (1.35 g, 5.30 mmol). The resulting suspension was stirred vigorously at ambient temperature. After 4 h, the reaction mixture was diluted with EtOAc, and the organic phase was washed successively with water, sat. aq. sodium bisulfate, and sat. aq. NaHCO$_3$. The organic phase was then concentrated in vacuo. The title compound was separated from the para-iodo isomer upon purification by flash chromatography on silica gel (0 to 15% EtOAc in hexanes, then 15% EtOAc in hexanes, then 15 to 100% EtOAc in hexanes; the title compound is the later eluting isomer): LCMS m/z 504.5 [M+H]$^+$; $^1$H NMR (500 MHz, CDCl$_3$) δ 13.08 (s, 1H), 8.17 (s, 1H), 8.10 (t, J=8.0 Hz, 1H), 8.06 (d, J=8.0 Hz, 1H), 7.86 (dd, J=7.5, 1.5 Hz, 1H), 7.82 (dd, J=8.0, 1.5 Hz, 1H), 7.52 (d, J=7.5 Hz, 1H), 6.75 (t, J=8.0 Hz, 1H), 4.33 (q, J=7.0 Hz, 2H), 1.43 (t, J=7.0 Hz, 3H).

Step B. Ethyl 1-(6-{2-[(2,4-dimethylbenzyl)oxy]-3-iodophenyl}pyridin-2-yl)-5-(trifluoromethyl)-1H-pyrazole-4-carboxylate To a solution of the title compound from Example 15 Step A (200 mg, 0.397 mmol), 2,4-dimethylbenzyl alcohol (81.0 mg, 0.596 mmol), and triphenylphosphine (156 mg, 0.596 mmol) in DCM (2 mL) was added diisopropyl azodicarboxylate (0.114 mL, 0.596 mmol), and the resulting mixture was stirred at ambient temperature. After 18 h, the reaction mixture was concentrated in vacuo. Purification by flash chromatography on silica gel (0 to 20% EtOAc in hexanes, then 20 to 100% EtOAc in hexanes) provided the title compound: LCMS m/z 594.8 [M+H]$^+$; $^1$H NMR (500 MHz, CDCl$_3$) δ 8.17 (s, 1H), 8.02 (d, J=8.0 Hz, 1H), 7.92 (d, J=7.5 Hz, 1H), 7.85-7.81 (m, 2H), 7.60 (d, J=7.5 Hz, 1H), 7.13 (d, J=7.5 Hz, 1H), 7.05 (t, J=7.5 Hz, 1H), 6.95-6.92 (m, 2H), 4.69 (s, 2H), 4.41 (q, J=7.0 Hz, 2H), 2.30 (s, 3H), 2.17 (s, 3H), 1.43 (t, J=7.0 Hz, 3H).

Step C. Ethyl 1-(6-{2-[(2,4-dimethylbenzyl)oxy]-3-methylphenyl}pyridin-2-yl)-5-(trifluoromethyl)-1H-pyrazole-4-carboxylate A vial was charged with the product from Example 15 Step B (40 mg, 0.064 mmol), trimethyl boroxine (49 mg, 50 wt. %, 0.193 mmol), and 1,1'-bis(diphenylphosphino)ferrocene-palladium(II)dichloride dichloromethane complex (5.3 mg, 0.006 mmol). Sodium carbonate (0.161 mL, 1.0 M aqueous, 0.161 mmol) and THF (0.25 mL) were added, and the resulting suspension was degassed by a nitrogen sparge. The vial was then capped and placed in a pre-heated (65° C.) oil bath. After 18 h, the reaction mixture was allowed to cool to ambient temperature, then was poured into water. The aqueous phase was extracted with EtOAc, and the organic phase was concentrated in vacuo. Purification by flash chromatography on silica gel (0 to 20% EtOAc in hexanes, then 20 to 100% EtOAc in hexanes) provided the title compound: LCMS m/z 510.8 [M+H]$^+$.

Step D. 1-(6-{2-[(2,4-Dimethylbenzyl)oxy]-3-methylphenyl}pyridin-2-yl)-5-(trifluoromethyl)-1H-pyrazole-4-carboxylic acid To a solution of the title compound from Example 15 Step C (12.0 mg, 0.023 mmol) in 1,4-dioxane (1.5 mL) was added lithium hydroxide (0.5 mL, 2.0 M in water, 1.00 mmol), and the resulting mixture was stirred at 50° C. After 30 min, the reaction mixture was rendered acidic by addition of aqueous hydrochloric acid, then was diluted with 1,4-dioxane and passed through a 0.45 micron syringe filter. Purification by reverse phase HPLC (40 to 100% acetonitrile in water, each with 0.1% v/v TFA) provided the title compound: LCMS m/z 482.8 [M+H]$^+$; $^1$H NMR (500 MHz, d$_6$-DMSO) δ 8.30 (s, 1H), 8.08 (t, J=8.0 Hz, 1H), 7.95 (d, J=8.0 Hz, 1H), 7.74 (d, J=8.0 Hz, 1H), 7.45 (dd, J=8.0, 1.5 Hz, 1H), 7.35-7.32 (m, 1H), 7.18 (t, J=7.5 Hz, 1H), 6.91-6.86 (m, 3H), 4.52 (s, 2H), 2.27 (s, 3H), 2.21 (s, 3H), 2.06 (s, 3H).

Example 16

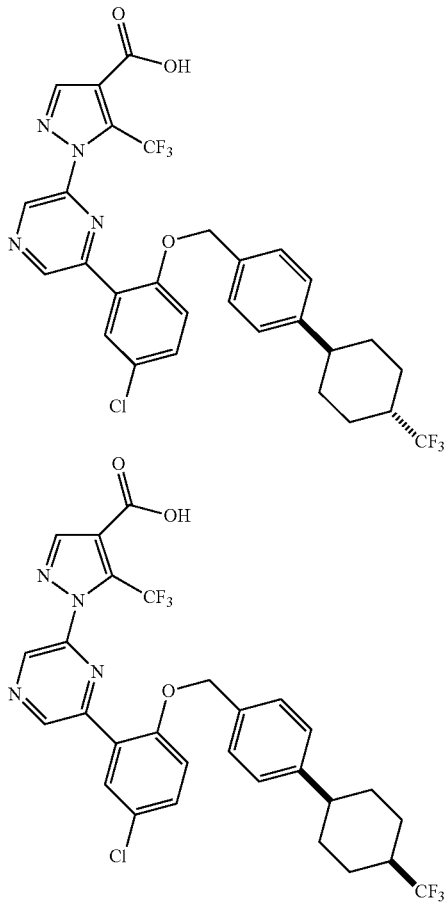

Step A. 2-(6-Chloropyrazin-2-yl)phenol

To a mixture of 2,6-dichloropyrazine (1.00 g, 6.71 mmol), 2-hydroxyphenylboronic acid (972 mg, 7.05 mmol) and trans dichlorobis(triphenylphosphine) palladium (II) (471 mg, 0.671 mmol) were added acetonitrile (20 mL) and sodium carbonate (13.4 mL, 1.0 M in water, 13.4 mmol), and the resulting mixture was degassed by a nitrogen sparge. The reaction flask was equipped with a reflux condenser, then was placed in a pre-heated oil bath (75° C.) and was stirred rapidly. After 5 h, the reaction mixture was allowed to cool to room temperature, then was poured into water and extracted with EtOAc. The organic phase was separated and concentrated in vacuo. Purification by chromatography on silica gel (0 to 25% EtOAc in hexanes, then 25 to 100% EtOAc in hexanes) provided the title compound: LCMS m/z 207.6 [M+H]$^+$; $^1$H NMR (500 MHz, CDCl$_3$) δ 11.64 (s, 1H), 9.11 (s, 1H), 8.53 (s, 1H), 7.85 (dd, J=8.0, 1.5 Hz, 1H), 7.40 (t, J=8.0 Hz, 1H), 7.07 (d, J=8.5 Hz, 1H), 6.99 (t, J=8.0 Hz, 1H).

Step B. Ethyl 1-[6-(2-hydroxyphenyl)pyrazin-2-yl]-5-(trifluoromethyl)-1H-pyrazole-4-carboxylate To a solution of the title compound from Example 16 Step A (0.500 grams, 2.42 mmol) in ethanol (20 mL) was added hydrazine hydrate (3.25 mL, 35% v/v, 36.3 mmol). The reaction flask was equipped with a reflux condenser, and the reaction mixture was stirred at 80° C. After 12 h, the mixture was allowed to cool to room temperature, whereupon a yellow solid precipitated. The solid was triturated with hexanes, filtered, washed with water, and dried in vacuo: LCMS m/z 203.2 [M+H]$^+$. To a solution of the crude pyrazinyl hydrazine in acetonitrile (10 mL) were added triethylamine (0.675 mL, 4.84 mmol) and ethyl 2-(ethoxymethylene)-4,4,4-trifluoro-3-oxobutyrate (0.872 g, 3.63 mmol). After 40 min at ambient temperature, the reaction mixture was placed in a 60° C. bath and was stirred for 30 min, at which point the reaction mixture was allowed to cool to ambient temperature, then was concentrated in vacuo. Purification by flash chromatography on silica gel (0 to 60% EtOAc in hexanes, then 60 to 100% EtOAc in hexanes) provided the title compound: LCMS m/z 379.1 [M+H]$^+$; $^1$H NMR (500 MHz, CDCl$_3$) δ 10.98 (s, 1H), 9.35 (s, 1H), 8.85 (s, 1H), 8.23 (s, 1H), 7.93 (dd, J=8.0, 1.5 Hz, 1H), 7.43 (t, J=8.0 Hz, 1H), 7.07 (d, J=8.5 Hz, 1H), 7.04 (t, J=8.0 Hz, 1H).

Step C. 1-{6-[5-Chloro-2-({4-[trans-4-(trifluoromethyl)cyclohexyl]benzyl}oxy)phenyl]pyrazin-2-yl}-5-(trifluoromethyl)-1H-pyrazole-4-carboxylic acid and 1-{6-[5-chloro-2-({4-[cis-4-(trifluoromethyl)cyclohexyl]benzyl}oxy)phenyl]pyrazin-2-yl}-5-(trifluoromethyl)-1H-pyrazole-4-carboxylic acid To a solution of the title compound from Example 16 Step B (100.0 mg, 0.264 mmol), the title compound from Example 8 Step E (102 mg, 0.397 mmol), and triphenylphosphine (104 mg, 0.397 mmol) in DCM (7 mL) was added diisopropyl azodicarboxylate (0.077 mL, 0.397 mmol), and the resulting mixture was stirred at ambient temperature. After 18 h, the reaction mixture was concentrated in vacuo. Purification by flash chromatography on silica gel (0 to 20% EtOAc in hexanes then 20 to 100% EtOAc in hexanes) provided the title compounds. The first eluting compound is the trans isomer: LCMS m/z 619.2 [M+H]$^+$; $^1$H NMR (500 MHz, CDCl$_3$) δ 9.44 (s, 1H), 8.85 (s, 1H), 8.17 (s, 1H), 8.00 (dd, J=7.5, 1.5 Hz, 1H), 7.46-7.43 (m, 1H), 7.33 (d, J=8.5 Hz, 2H), 7.21 (d, J=8.5 Hz, 2H), 7.16-7.12 (m, 2H), 5.18 (s, 2H), 4.40 (q, J=7.0 Hz, 2H), 2.54-2.51 (m, 1H), 2.11-2.00 (m, 5H), 1.50-1.45 (m, 4H), 1.42 (t, J=7.0 Hz, 3H). The second eluting compound is the cis isomer: LCMS m/z 619.2 [M+H]$^+$; $^1$H NMR (500 MHz, CDCl$_3$) δ 9.46 (s, 1H), 8.86 (s, 1H), 8.18 (s, 1 H), 8.01 (dd, J=7.5, 1.5 Hz, 1H), 7.47-7.44 (m, 1H), 7.35 (d, J=8.5 Hz, 2H), 7.27 (d, J=8.5 Hz, 2H), 7.17-7.13 (m, 1H), 5.20 (s, 2H), 4.41 (q, J=7.0 Hz, 2H), 2.74-2.71 (m, 1H), 2.36-2.29 (m, 1H), 2.01-1.90 (m, 4H), 1.81-1.71 (m, 4H), 1.41 (t, J=7.0 Hz, 3H).

Step D. Ethyl 1-{6-[5-chloro-2-({4-[trans-4-(trifluoromethyl)cyclohexyl]benzyl}oxy)phenyl]pyrazin-2-yl}-5-(trifluoromethyl)-1H-pyrazole-4-carboxylate and ethyl 1-{6-[5-chloro-2-({4-[cis-4-(trifluoromethyl)cyclohexyl]benzyl}oxy)phenyl]pyrazin-2-yl}-5-(trifluoromethyl)-1H-pyrazole-4-carboxylate To separate solutions of the title compounds from Example 16 Step C in 1,4-dioxane (1 mL) was added lithium hydroxide (0.5 mL, 2.0 M aqueous, 1.00 mmol), and the resulting mixtures were stirred at 50° C. After 30 min, the reaction mixtures were rendered acidic by addition of aqueous hydrochloric acid, then were diluted with 1,4-dioxane and passed through 0.45 micron syringe filters. Purification by reverse phase HPLC (40 to 100% acetonitrile in water, each with 0.1% v/v TFA) provided the title compounds. Analytical data for the trans isomer: LCMS m/z 591.5 [M+H]$^+$; $^1$H NMR (500 MHz, d$_6$-DMSO) δ 9.37 (s, 1H), 9.00 (s, 1H), 8.39 (s, 1H), 7.78 (dd, J=7.5, 1.5 Hz, 1H), 7.54-7.50 (m, 1H), 7.37-7.34 (m, 3H), 7.22 (d, J=8.0 Hz, 2H), 7.15 (t, J=7.5 Hz, 1H), 5.23 (s, 2H), 2.55-2.49 (m, 1H), 2.35-2.32 (m, 1H), 1.96-1.85 (m, 4H), 1.55-1.36 (m, 4H). Analytical data for the cis isomer: LCMS m/z 591.5 [M+H]$^+$; $^1$H NMR (500 MHz, d$_6$-DMSO) δ 9.38 (s, 1H), 9.00 (s, 1H), 8.38 (s, 1H), 7.78 (dd, J=7.5, 1.5 Hz, 1H), –54-7.50 (m, 1H), 7.39-7.34 (m, 3H), 7.25 (d, J=8.0 Hz, 2H), 7.15 (t, J=7.5 Hz, 1H), 5.24 (s, 2H), 2.76-2.73 (m, 1H), 2.52-2.48 (m, 1H), 1.82-1.77 (m, 2H), 1.75-1.70 (m, 6H).

Example 17

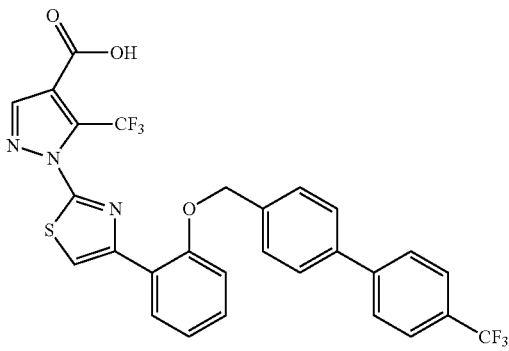 [SMILES: O=C(O)c1cnn(-c2nc(-c3ccccc3OCc3ccc(-c4ccc(C(F)(F)F)cc4)cc3)cs2)c1C(F)(F)F]

Step A. Ethyl 1-[4-(2-methoxyphenyl)-1,3-thiazol-2-yl]-5-(trifluoromethyl)-1H-pyrazole-4-carboxylate A solution of ethyl 1-(aminocarbonothioyl)-5-hydroxy-5-(trifluoromethyl)-4,5-dihydro-1H-pyrazole-4-carboxylate (470 mg, 1.65 mmol, prepared according to J. Comb. Chem. 2002, 4, 23-32) and 2-bromo-2'-methoxyacetophenone (377 mg, 1.65 mmol) in ethanol (8 mL) was heated at 80° C. After 1 h, the mixture was allowed to cool to ambient temperature, then was concentrated in vacuo. Purification by flash chromatography on silica gel (0 to 55% EtOAc in hexanes) provided the title compound as an off-white solid: LCMS m/z 398.5 [M+H]$^+$; $^1$H NMR (500 MHz, CD$_3$OD) δ 8.26 (dd, J=7.6, 1.6 Hz, 1H), 8.13 (s, 1H), 8.03 (s, 1H), 7.37 (ddd, J=8.9, 6.5, 1.8 Hz, 1H), 7.12-7.01 (m, 2H), 4.42 (q, J=7.0 Hz, 2H), 4.02 (s, 3H), 1.42 (t,=7.0 Hz, 3H).

Step B. Ethyl 1-[4-(2-hydroxyphenyl)-1,3-thiazol-2-yl]-5-(trifluoromethyl)-1H-pyrazole-4-carboxylate To a cooled (0° C.) solution of the title compound from Example 17 Step A (353 mg, 0.888 mmol) in DCM (6.3 ml) was added BBr$_3$ (2.67 ml, 1.0 M in DCM, 2.67 mmol) dropwise. After the addition was complete, the mixture was allowed to warm up to ambient temperature. After 1 h, the reaction mixture was quenched by addition of sat. aq. NaHCO$_3$ and extracted with DCM. The organic phase was separated and concentrated in vacuo. Purification by flash chromatography on silica gel (0 to 60% EtOAc in hexanes) provided the title compound as a yellow solid: LCMS m/z 384.5 [M+H]$^+$; $^1$H NMR (500 MHz, CD$_3$OD) δ 10.17 (s, 1H), 8.18 (s, 1H), 7.67 (dd, J=8.0, 1.9 Hz, 1H), 7.34 (t, J=8.5 Hz, 1H), 7.09 (dd, J=8.2, 0.9 Hz, 1H), 6.98 (t, J=7.4 Hz, 1H), 4.45 (m, 2H), 1.44 (t, J=7.1 Hz, 3H).

Step C. 5-(Trifluoromethyl)-1-[4-(2-{[4'-(trifluoromethyl)biphenyl-4-yl]methoxy}phenyl)-1,3-thiazol-2-yl]-1H-pyrazole-4-carboxylic acid The title compound was prepared from the title compound from Example 17 Step B by direct analogy to the procedures outlined in Example 2 Steps A-C: LCMS m/z 590.5 [M+H]$^+$; $^1$H NMR (500 MHz, d$_6$-DMSO) δ 8.40 (s, 1H), 8.22 (s, 1H), 8.08 (dd, J=7.5, 1.5 Hz, 1H), 7.93 (d, J=8.5 Hz, 2H), 7.83 (d, J=8.5 Hz, 2H), 7.81 (d, J=8.5 Hz, 2H), 7.68 (d, J=8.5 Hz, 2H), 7.40-7.37 (m, 1H), 7.31 (d, J=8.5 Hz, 1H), 7.11 (t, J=7.5 Hz, 1H), 5.43 (s, 2H).

Example 18

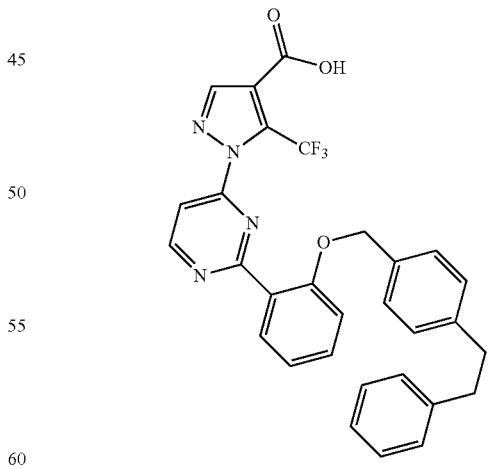

Step A. Ethyl 1-(2-chloropyrimidin-4-yl)-5-(trifluoromethyl)-1H-pyrazole-4-carboxylate To a solution 2-chloro-6-hydrazinopyrimidine (1.00 g, 6.92 mmol) and triethylamine (0.964 mL, 6.92 mmol) in acetonitrile (35 mL) was added ethyl 2-(ethoxymethylene)-4,4,4-trifluoro-3-oxobutyrate (1.35 mL, 6.97 mmol). After 45 min, the reaction mixture was placed in a 90° C. oil bath. After 1 h, the reaction mixture was allowed to cool to ambient temperature, then was concentrated in vacuo. Purification by flash chromatography on silica gel (0 to 60% EtOAc in hexanes, then 60 to 100% EtOAc in hexanes) provided the title compound: LCMS m/z 321.0 [M+H]$^+$; $^1$H NMR (500 MHz, CDCl$_3$) δ 8.80 (d, J=5.5 Hz, 1H), 8.12 (s, 1H), 7.76 (d, J=5.5 Hz, 1H), 4.39 (q, J=7.0 Hz, 2H), 1.39 (t, J=7.0 Hz, 3H).

Step B. 1-[2-(2-{[4-(2-Phenylethyl)benzyl]oxy}phenyl)pyrimidin-4-yl]-5-(trifluoromethyl)-1H-pyrazole-4-carboxylic acid Suzuki coupling of the title compound from Example 18 Step A with 2-methoxyphenylboronic acid, followed by treatment with BBr$_3$ (according to Example 8 Steps A and B) gave a pyrimidinyl phenol which was processed to the title compound according to Example 1 Steps C and D: LCMS m/z 545.3 [M+H]$^+$; $^1$H NMR (500 MHz, d$_6$-DMSO) δ 9.20 (d, J=5.5 Hz, 1H), 8.42 (s, 1H), 7.88 (d, J=5.5 Hz, 1H), 7.69 (dd, J=8.0, 2.0 Hz, 1H), 7.50-7.47 (m, 1H), 7.27-2.08 (m, 11H), 5.13 (s, 2H), 2.82 (s, 4H).

Example 19

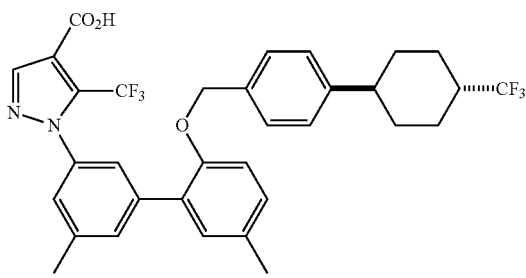

Step A. 2-Chloro-6-(2-methoxy-5-methylphenyl)-4-nitropyridine

The title compound was prepared according to the procedure described in Example 1 Step B, by reaction of 2-methoxy-5-methylphenylboronic acid with 2,6-dichloro-4-nitropyridine: LCMS m/z 279.5 [M+H]$^+$; $^1$H NMR (500 MHz, CDCl$_3$) δ 8.19 (d, J=8.5 Hz, 1H), 7.52 (d, J=2.1 Hz, 1H), 7.44 (d, J=8.5 Hz, 1H), 7.28 (dd, J=8.5, 2.1 Hz, 1H), 6.83 (d, J=8.5 Hz, 1H), 3.72 (s, 3H), 2.42 (s, 3H).

Step B. Di-tert-butyl 1-[6-(2-methoxy-5-methylphenyl)-4-nitropyridin-2-yl]hydrazine-1,2-dicarboxylate A mixture of the title compound from Example 19 Step A (1.5 g, 5.4 mmol), di-tert-butyl hydrazine-1,2-dicarboxylate (1.375 g, 5.92 mmol), DPPF (360 mg, 0.65 mmol), Pd$_2$dba$_3$ (0.4 g, 0.43 mmol), Cs$_2$CO$_3$ (1.90 g, 5.83 mmol) and 12 mL toluene was stirred at 100° C. After 20 h, the mixture was allowed to cool to ambient temperature, then purification by flash chromatography on silica gel using hexane-EtOAc (20:1 to 4:1 v/v) as mobile phase provided the title compound: LCMS m/z 375.6 (observed [M+H]$^+$ for the ion corresponding to loss of one Boc group); $^1$H NMR (400 MHz, acetone-d$_6$) δ 7.86 (d, J=2.1 Hz, 1H), 7.26 (dd, J=8.4, 2.1 Hz, 1H), 7.07 (d, J=8.4, 2.1 Hz, 1H), 3.93 (s, 3H), 2.31 (s, 3H), 1.54 (s, 9H), 1.47 (s, 9H).

Step C. 2-Hydrazino-6-(2-methoxy-5-methylphenyl)-4-nitropyridine

A mixture of the title compound from Example 19 Step B (2.0 g, 2.2 mmol), 23 mL 1,4-dioxane and concentrated HCl (2 mL) was stirred for 14 h. Concentrated HCl (8 mL) was added dropwise. After 1 h, concentrated HCl (4 mL) was added dropwise. After 4 h, the reaction mixture was diluted with water and concentrated to a solid form. The solid was further washed by ether twice to give the crude title compound which was used without further purification: LCMS m/z 275.5 [M+H]$^+$.

Step D. Ethyl 1-[6-(2-methoxy-5-methylphenyl)-4-nitropyridin-2-yl]-5-(trifluoromethyl)-1H-pyrazole 4-carboxylate Reaction of the title compound from Example 19 Step C with ethyl 2-(ethoxymethylene)-4,4,4-trifluoro-3-oxobutyrate, according to chemistry described in Example 1 Step A, provided the title compound: LCMS m/z 451.6 [M+H]$^+$.

Step E. Ethyl 1-[4-amino-6-(2-methoxy-5-methylphenyl)pyridin-2-yl]-5-(trifluoromethyl)-1H-pyrazole-4-carboxylate A mixture of the title compound from Example 19 Step D (1.2 g, 2.7 mmol), DMF (15 mL), water (1.5 mL) and tin (II) chloride dihydrate (1.8 g, 7.9 mmol) was heated at 70° C. for 1.5 h, leading to reduction of the nitro group to the corresponding hydroxylamine. A second addition of tin (II) chloride dehydrate (2.4 g, 10.6 mmol) followed by heating at 100° C. overnight led to little progress. Water was added, and the reaction mixture was extracted with hexanes-EtOAc. The organic phase was separated and passed through a pad of silica gel. Hydrogenation using Pd-black (450 mg, 4.2 mmol) in EtOAc:EtOH (100 mL, 1:1 v/v) under 50 psi H$_2$, followed by filtration and concentration, provided the title compound: LCMS m/z 421.6 [M+H]$^+$; $^1$H NMR (400 MHz, acetone-d$_6$) δ 8.09 (s, 1H), 7.71 (d, J=2.1 Hz, 1H), 7.45 (d, J=1.9 Hz, 1H), 7.13 (dd, J=8.4 Hz, 2.1 Hz, 1H), 6.96 (d, J=8.4 Hz, 1H), 6.84 (d, J=1.9 Hz, 1H), 4.31 (q, J=7.1 Hz, 2H), 3.82 (s, 3H), 2.26 (s, 3H), 1.34 (t, J=7.1 Hz, 3H).

Step F. Ethyl 1-[4-iodo-6-(2-methoxy-5-methylphenyl)pyridin-2-yl]-5-(trifluoromethyl)-1H-pyrazole-4-carboxylate Tert-butyl nitrite (0.68 mL, 0.59 mmol) was added to a solution of the title compound from Example 19 Step E (1.2 g, 2.9 mmol) and iodine (0.87 g, 3.4 mmol) in chloroform (20 mL). The resulting mixture was heated at 60° C. for 30 min, cooled and quenched with aqueous sodium sulfite. Extraction with hexane-EtOAc, followed by silica gel flash chromatography using Hexane-EtOAc (20/1 to 7/1) provided the title compound: LCMS m/z 532.6 [M+H]$^+$; $^1$H NMR (500 MHz, CDCl$_3$) δ 8.54 (d, J=1.1 Hz, 1H), 8.15 (s, 1H), 7.98 (d, J=1.1 Hz, 1H), 7.79 (d, J=2.1 Hz, 1H), 7.25 (dd, J=8.5 Hz, 2.1 Hz, 1H), 6.94 (d, J=8.5 Hz, 1H), 4.43 (q, J=7.1 Hz, 2H), 3.93 (s, 3H), 2.39 (s, 3H), 1.42 (t, J=7.1 Hz, 3H).

Step G. Ethyl 1-[6-(2-hydroxy-5-methylphenyl)-4-iodopyridin-2-yl]-5-(trifluoromethyl)-1H-pyrazole-4-carboxylate A solution of the title compound from Example 19 Step F (1 g, 1.88 mmol) and iodotrimethylsilane (3.6 mL) in 15 mL chloroform was heated at 80° C. for 7 h. A second portion of iodotrimethylsilane (2 mL) was added and heating was continued at 90° C. overnight. The volatiles were removed in vacuo. Toluene was added, and the volatiles were removed in vacuo. Finally, dry MeOH was added, and the volatiles were removed in vacuo. Silica gel flash chromatography using hexanes:EtOAc (20:1 to pure EtOAc) gave the title compound: LCMS m/z 518.6 [M+H]$^+$; $^1$H NMR (400 MHz, acetone-$d_6$) δ 8.87 (d, J=1.1 Hz, 1H), 8.24 (s, 1H), 8.12 (d, J=1.1 Hz, 1H), 7.89 (d, J=2 Hz, 1H), 7.18 (dd, J=8.5, 2.0 Hz, 1H), 6.84 (d, J=8.3 Hz, 1H), 4.37 (q, J=7.1 Hz, 2H), 2.30 (s, 3H), 1.35 (t, J=7.1 Hz, 3H).

Step H. 1-(Chloromethyl)-4-[trans-4-(trifluoromethyl)cyclohexyl]benzene and 1-(chloromethyl)-4-[cis]-4-(trifluoromethyl)cyclohexyl]benzene To a solution of the title compound from Example 8 Step E (140 mg, 0.542 mmol) in chloroform (1.4 mL) was added thionyl chloride (0.100 mL, 1.37 mmol). The mixture was stirred at ambient temperature for 30 min, then was concentrated in vacuo. Purification by flash chromatography on silica gel (0 to 15% EtOAc in hexanes then 15 to 25% EtOAc in hexanes) gave the title compounds, as a mixture of cis:trans isomers: LCMS m/z 241.6 [M−Cl]$^+$.

Step I. Ethyl 1-{4-iodo-6-[5-methyl-2-({4-[trans-4-(trifluoromethyl)cyclohexyl]benzyl}oxy)phenyl]pyridin-2-yl}-5-(trifluoromethyl)-1H-pyrazole-4-carboxylate A mixture of the title compound from Example 19 Step G (150 mg, 0.289 mmol), the title compound from Example 19 Step H (100 mg, 0.361 mmol), Cs$_2$CO$_3$ (141 mg, 0.434 mmol) and DMF (1 mL) was stirred at RT overnight. 2 N HCl was added and the reaction mixture was extracted with mixture of hexanes and EtOAc. The combined organic layer was concentrated and purified by prep TLC (20% EtOAc in hexanes) to give the title compound: LCMS m/z 758.7 [M+H]$^+$

Step J. 1-{4-Methyl-6-[5-methyl-2-({4-[trans-4-(trifluoromethyl)cyclohexyl]benzyl}oxy)phenyl]pyridin-2-yl}-5-(trifluoromethyl)-1H-pyrazole-4-carboxylic acid A mixture of the title compound from Example 19 Step I (20 mg, 0.026 mmol) Pd(PPh$_3$)$_4$ (10.7 mg, 0.009 mmol), K$_2$CO$_3$ (11 mg, 0.08 mmol), trimethyl boroxine (11.6 mg, 0.09 mmol), and dioxane (0.5 mL) was heated in a microwave reactor at 140° C. for 1 h, cooled, diluted with hexanes and passed through a pad of silica gel eluted by dichloromethane. The solvent was removed in vacuo. Treatment with a mixture of 1,4-dioxane (0.1 mL), MeOH (0.1 mL) and 3 N NaOH (0.1 mL) at 50° C. for 15 min, followed by reverse phase HPLC using a YMC C-18 column (45 to 95% acetonitrile in water, each with 0.1% v/v TFA) provided the title compound: LCMS m/z 618.8 [M+H]$^+$; $^1$H NMR (400 MHz, acetone-$d_6$), δ 8.17 (s, 1H), 8.08 (s, 1H), 7.75 (d, J=2.1 Hz, 1H), 7.48 (s, 1H), 7.41 (d, J=8.1 Hz, 2H), 7.27 (d, J=8.1 Hz, 2H), 7.20 (dd, J=8.4 Hz, 2.1 Hz, 1H), 7.12 (d, J=8.4 Hz, 1H), 2.43 (s, 3H), 2.29 (s, 3H), 2.59 (m, 1H), 1.96 (m, 2H), 1.67-1.39 (m, 4H).

The compounds in TABLE 1 were prepared using the chemistry described in Examples 1-19.

TABLE 1

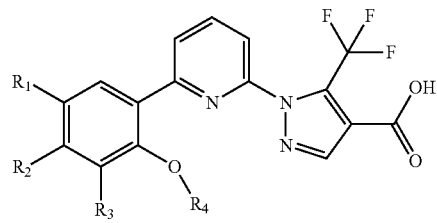

| Entry | R1 | R2 | R3 | R4 | MS |
|---|---|---|---|---|---|
| 20 | —CF$_3$ | H | H | —CH$_2$—C$_6$H$_4$—OCF$_3$ | 592.1 [M + H]$^+$ |
| 21 | H | H | H | —CH$_2$—C$_6$H$_4$—O—C$_6$H$_5$ | 546.2 [M + H]$^+$ |
| 22 | H | H | H | —CH$_2$—C$_6$H$_4$—C$_6$H$_4$—Cl | 572.1 [M + Na]$^+$ |

TABLE 1-continued

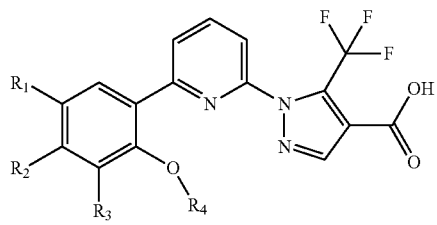

| Entry | R1 | R2 | R3 | R4 | MS |
|---|---|---|---|---|---|
| 23 | H | H | H | —CH₂—C₆H₄—C₆H₄—CF₃ (4-(3'-CF₃)biphenyl-methyl) | 584.1 [M + H]⁺ |
| 24 | Me | H | H | —CH₂—C₆H₄—C₆H₄—CF₃ (4-(4'-CF₃)biphenyl-methyl) | 598.7 [M + H]⁺ |
| 25 | Me | H | H | —CH₂—C₆H₄—C₆H₄—Cl (4-(4'-Cl)biphenyl-methyl) | 564.6 [M + H]⁺ |
| 26 | Me | H | H | —CH₂—C₆H₄—C₆H₅ (4-biphenyl-methyl) | 528.4 [M − H]⁻ |
| 27 | Br | H | H | —CH₂—C₆H₄—CH₂—C₆H₅ | 624.5 [M + H]⁺ |
| 29 | cPr | H | H | —CH₂—C₆H₄—CH₂—C₆H₅ | 584.5 [M + H]⁺ |
| 30 | CF₃ | H | H | —CH₂—C₆H₄—C₆H₄—Cl | 618.2 [M + H]⁺ |
| 31 | CF₃ | H | H | —CH₂—(pyridyl)—C₆H₄—CF₃ | 652.3 [M + H]⁺ |
| 32 | CF₃ | H | H | —CH₂—C₆H₄—C₆H₄—F | 602.2 [M + H]⁺ |
| 33 | H | H | H | —CH₂—C₆H₃(Cl)—C₆H₄—Cl | 584.4 [M + H]⁺ |
| 34 | H | H | H | —CH₂—C₆H₃(Cl)—C₆H₄—F | 568.1 [M + H]⁺ |

TABLE 1-continued
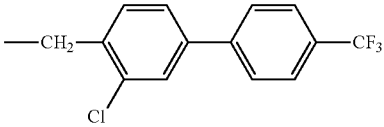 [SMILES: CCc1ccc(-c2ccc(C(F)(F)F)cc2)cc1Cl]
| Entry | R1 | R2 | R3 | R4 | MS |
|---|---|---|---|---|---|
| 35 | H | H | H | 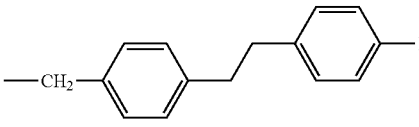 | 618.0 [M + H]⁺ |
| 36 | H | H | H | 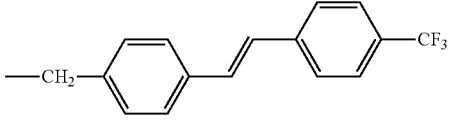 | 562.5 [M + H]⁺ |
| 37 | H | H | H | 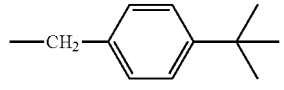 | 610.5 [M + H]⁺ |
| 38 | Me | H | H | 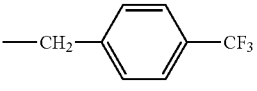 | 510.6 [M + H]⁺ |
| 39 | Me | H | H | 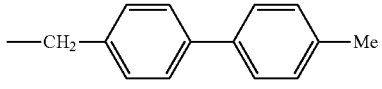 | 522.5 [M + H]⁺ |
| 40 | H | H | H | 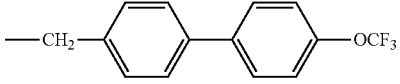 | 552.2 [M + Na]⁺ |
| 41 | H | H | H | 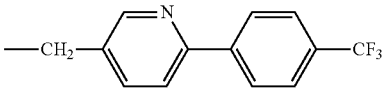 | 600.2 [M + H]⁺ |
| 42 | Me | H | H |  | 599.6 [M + H]⁺ |
| 43 | H | H | H | 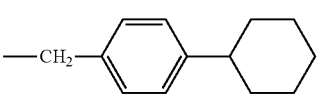 | 508.6 [M + H]⁺ |
| 44 | H | H | H | 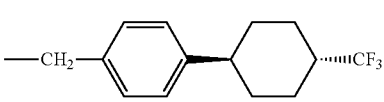 | 522.6 [M + H]⁺ |
| 45 | H | H | H | 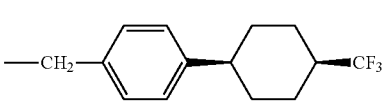 | 590.5 [M + H]⁺ |
| 46 | H | H | H |  | 590.5 [M + H]⁺ |

TABLE 1-continued

| Entry | R1 | R2 | R3 | R4 | MS |
|---|---|---|---|---|---|
| 47 | Me | H | I | —CH₂—(C₆H₄)—(cyclohexyl)—CF₃ | 730.6 [M + H]⁺ |
| 48 | Cl | H | I | —CH₂—(C₆H₄)—(cyclohexyl)—CF₃ | 750.6 [M + H]⁺ |
| 49 | H | H | I | —CH₂—(C₆H₃-Me)—(cyclohexyl)—OMe | 692.9 [M + H]⁺ |
| 50 | cPr | H | H | —CH₂—(C₆H₄)—(C₆H₄)—CF₃ | 624.2 [M + H]⁺ |
| 51 | H | H | H | —CH₂—(C₆H₃-Me)—(C₆H₄)—CF₃ | 598.2 [M + H]⁺ |
| 52 | H | H | H | —CH₂—(C₆H₃-Me)—(C₆H₄)—Cl | 586.2 [M + Na]⁺ |
| 53 | H | H | H | —CH₂—(C₆H₃-Me)—(C₆H₄)—CF₃ | 598.2 [M + H]⁺ |
| 54 | H | H | H | —CH₂—(C₆H₃-Me)—(C₆H₄)—Cl | 564.2 [M + H]⁺ |
| 55 | H | H | H | —CH₂—(C₆H₄)—tBu | 496.6 [M + H]⁺ |
| 56 | H | H | H | —CH₂—(C₆H₃-F)—(C₆H₄)—CF₃ | 602.4 [M + H]⁺ |
| 57 | H | H | H | —CH₂—(C₆H₃-F)—(C₆H₄)—Cl | 568.5 [M + H]⁺ |

TABLE 1-continued

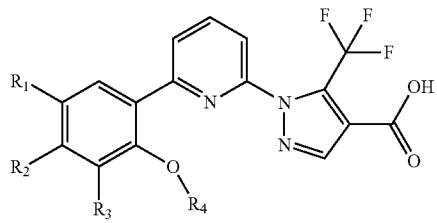

| Entry | R1 | R2 | R3 | R4 | MS |
|---|---|---|---|---|---|
| 58 | H | H | H | —CH₂-(3-F,4-(4-OCF₃-phenyl)phenyl) | 618.4 [M + H]⁺ |
| 59 | H | H | H | —CH₂-(3-F,4-(4-F-phenyl)phenyl) | 552.4 [M + H]⁺ |
| 60 | H | H | H | —CH₂-(3-F,4-(4-F,3-CF₃-phenyl)phenyl) | 620.4 [M + H]⁺ |
| 61 | H | H | H | —(CH₂)₂-(4-tert-butylphenyl) | 510.5 [M + H]⁺ |
| 62 | F | H | H | —CH₂-(4-(4-CF₃-phenyl)phenyl) | 602.3 [M + H]⁺ |
| 63 | F | H | H | —CH₂-(4-(4-Cl-phenyl)phenyl) | 566.3 [M − H]⁻ |
| 64 | F | H | H | —CH₂-(4-(4-OCF₃-phenyl)phenyl) | 618.3 [M + H]⁺ |
| 65 | F | H | H | —CH₂-(5-(4-F-phenyl)pyridin-2-yl) | 552.4 [M + H]⁺ |
| 66 | F | H | H | —CH₂-(4-(4-F,3-CF₃-phenyl)phenyl) | 620.4 [M + H]⁺ |
| 67 | F | H | H | —CH₂-(4-(3-CF₃-phenyl)phenyl) | 602.4 [M + H]⁺ |
| 68 | H | H | H | —CH₂-(2-methyl-4-(2-methyl-4-F-phenyl)phenyl) | 562.6 [M + H]⁺ |

TABLE 1-continued
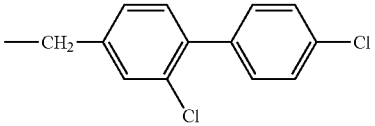 [SMILES: CCc1ccc(-c2ccc(Cl)cc2)c(Cl)c1]
| Entry | R1 | R2 | R3 | R4 | MS |
|---|---|---|---|---|---|
| 69 | H | H | H | 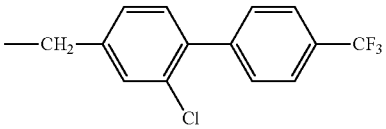 | 584.0 [M + H]+ |
| 70 | H | H | H | 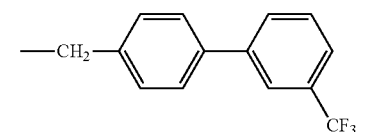 | 618.0 [M + H]+ |
| 71 | Me | H | H | 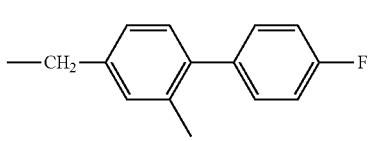 | 598.2 [M + H]+ |
| 72 | H | H | H | 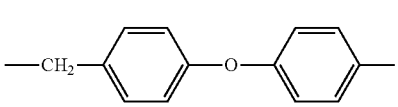 | 548.2 [M + H]+ |
| 73 | H | H | H | 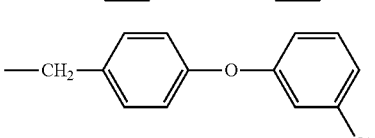 | 548.5 [M − H]− |
| 74 | H | H | H | 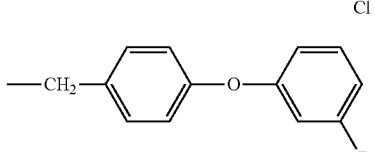 | 564.4 [M − H]− |
| 75 | H | H | H | 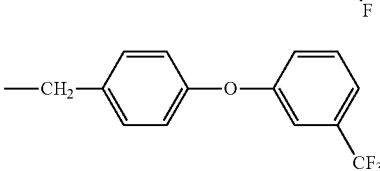 | 548.5 [M − H]− |
| 76 | H | H | H | 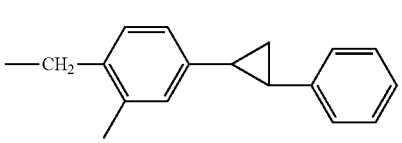 | 598.4 [M − H]− |
| 77 | H | H | H | 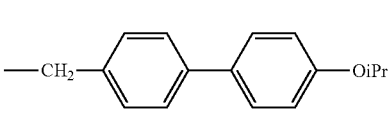 | 568.5 [M − H]− |
| 78 | H | H | H | —CH₂—⌬—⌬—OiPr | 596.2 [M + Na]+ |

TABLE 1-continued

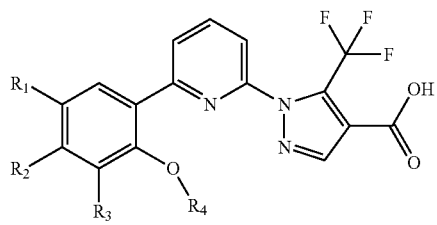

| Entry | R1 | R2 | R3 | R4 | MS |
|---|---|---|---|---|---|
| 79 | H | H | H | —CH$_2$-(4-(3,4-difluorophenyl)phenyl) | 552.2 [M + H]$^+$ |
| 80 | H | H | H | —CH$_2$-(4-(3,4-dichlorophenyl)phenyl) | 584.0 [M + H]$^+$ |
| 81 | H | H | H | —CH$_2$-(4-(3-chloro-4-methoxyphenyl)phenyl) | 602.1 [M + Na]$^+$ |
| 82 | H | H | H | —CH$_2$-(4-(3-chloro-4-trifluoromethylphenyl)phenyl) | 617.8 [M + H]$^+$ |
| 83 | H | H | H | —CH$_2$-(4-(4-chloro-3-trifluoromethylphenyl)phenyl) | 617.8 [M + H]$^+$ |
| 84 | Me | H | H | —CH$_2$-(3-methyl-4'-trifluoromethylbiphenyl) | 612.2 [M + H]$^+$ |
| 85 | Me | H | H | —CH$_2$-(3-methyl-4'-methylbiphenyl) | 580.1 [M + Na]$^+$ |
| 86 | Me | H | H | —CH$_2$-(3-methyl-4'-chlorobiphenyl) | 600.0 [M + Na]$^+$ |
| 87 | Me | H | H | —CH$_2$-(2,3-bis(trifluoromethyl)... 5-CF$_3$ phenyl) | 590.0 [M + H]$^+$ |

TABLE 1-continued

| Entry | R1 | R2 | R3 | R4 | MS |
|---|---|---|---|---|---|
| 88 | Me | H | H | —CH₂-(2,3-dimethylphenyl, 5-methyl) | 482.1 [M + H]⁺ |
| 89 | H | H | H | —CH₂-(2-chloro-6-(4-trifluoromethylphenyl)pyridin-3-yl) | 619.1 [M + H]⁺ |
| 90 | H | H | H | —CH₂-(3-methyl-3',4'-difluorobiphenyl-4-yl) | 566.1 [M + H]⁺ |
| 91 | H | H | H | —CH₂-(4-bromo-2-methylphenyl) | 534.0 [M + H]⁺ |
| 92 | H | H | H | —CH₂-(4-cyclohexyl-2-methylphenyl) | 558.1 [M + Na]⁺ |
| 93 | H | H | H | —CH₂-(4-cyclopentyl-2-methylphenyl) | 544.1 [M + Na]⁺ |
| 94 | H | H | H | —CH₂-(2,4-dimethylphenyl) | 468.0 [M + H]⁺ |
| 95 | Me | H | H | —(CH₂)₃-cyclohexyl | 488.0 [M + H]⁺ |
| 96 | Me | H | H | —CH₂-(2-methyl-5-phenylfuran-3-yl) | 556.1 [M + Na]⁺ |
| 97 | Me | H | H | —CH₂-cyclohexyl | 460.0 [M + H]⁺ |

TABLE 1-continued

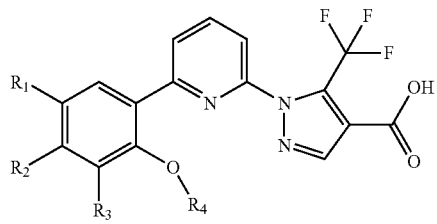

| Entry | R1 | R2 | R3 | R4 | MS |
|---|---|---|---|---|---|
| 98 | Me | H | H | —CH₂-(2-benzothiazolyl) | 511.1 [M + H]⁺ |
| 99 | H | H | H | —CH₂-(3-position of 2-cyclopropyl-6-(4-trifluoromethylphenyl)pyridine) | 625.4 [M + H]⁺ |
| 100 | H | H | H | —CH₂-(4-(trans-4-trifluoromethylcyclohexyl)-2-methylphenyl) | 604.4 [M + H]⁺ |
| 101 | H | H | H | —CH₂-(4-(cis-4-trifluoromethylcyclohexyl)-2-methylphenyl) | 604.5 [M + H]⁺ |
| 102 | Me | H | H | —CH₂-(2,4,6-trimethylphenyl) | 518.0 [M + Na]⁺ |
| 103 | CF3 | H | H | —CH₂-(2,4-dimethylphenyl) | 536.6 [M + H]⁺ |
| 104 | CF3 | H | H | —CH₂-(4-tert-butylphenyl) | 564.6 [M + H]⁺ |
| 105 | Me | H | H | —CH₂-(3-(4-tert-butylphenyl)-1,2,4-oxadiazol-5-yl) | 578.6 [M + H]⁺ |
| 106 | Me | H | H | —CH₂-(4-cyclopropyl-2-methylphenyl) | 508.6 [M + H]⁺ |

TABLE 1-continued

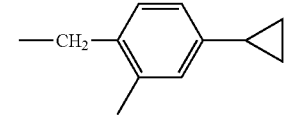

| Entry | R1 | R2 | R3 | R4 | MS |
|---|---|---|---|---|---|
| 107 | CF3 | H | H | 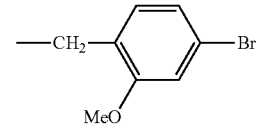 —CH₂— (2-methyl-5-cyclopropylphenyl) | 584.5 [M + H]⁺ |
| 108 | H | H | H | 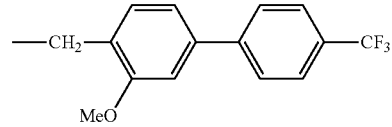 —CH₂— (2-MeO-5-Br-phenyl) | 548.0 [M + H]⁺ |
| 109 | H | H | H | 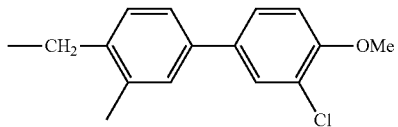 —CH₂—(3-MeO-4'-CF₃-biphenyl) | 614.1 [M + H]⁺ |
| 110 | H | H | H | 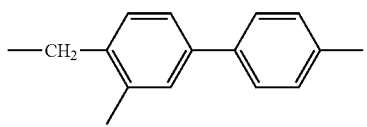 —CH₂—(3-methyl-3'-Cl-4'-OMe-biphenyl) | 616.2 [M + Na]⁺ |
| 111 | H | H | H | 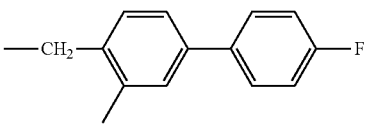 —CH₂—(3-methyl-4'-methyl-biphenyl) | 566.2 [M + Na]⁺ |
| 112 | H | H | H | 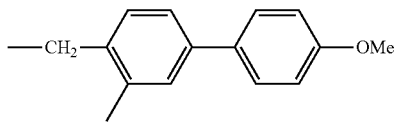 —CH₂—(3-methyl-4'-F-biphenyl) | 570.0 [M + Na]⁺ |
| 113 | H | H | H | 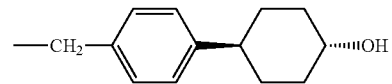 —CH₂—(3-methyl-pyridyl-OMe) | 582.0 [M + Na]⁺ |
| 114 | H | H | H | 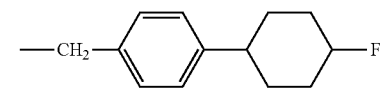 —CH₂—(phenyl-cyclohexyl-OH) | 538.8 [M + H]⁺ |
| 115 | H | H | H | 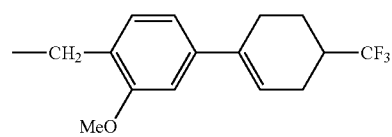 —CH₂—(phenyl-cyclohexyl-F) | 540.9 [M + H]⁺ |
| 116 | H | H | H | —CH₂—(3-MeO-phenyl-cyclohexenyl-CF₃) | 618.1 [M + H]⁺ |

TABLE 1-continued

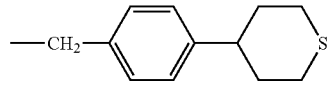

| Entry | R1 | R2 | R3 | R4 | MS |
|---|---|---|---|---|---|
| 117 | H | H | H | —CH₂—(C₆H₄)—(tetrahydrothiopyran-4-yl) | 540.5 [M + H]⁺ |
| 118 | H | H | H | —CH₂—(C₆H₄)—(1,1-dioxo-tetrahydrothiopyran-4-yl) | 572.5 [M + H]⁺ |
| 119 | H | H | H | —CH₂—(3-AllylO-biphenyl-4'-CF₃) | 640.2 [M + H]⁺ |
| 120 | Me | H | H | —CH₂—(3-AllylO-4-Me-phenyl) | 524.6 [M + H]⁺ |
| 121 | H | H | H | —CH₂—(3-cPrCH₂O-biphenyl-4'-CF₃) | 564.2 [M + H]⁺ |
| 122 | H | H | H | —CH₂—(3-cPr-biphenyl-4'-CF₃) | 624.2 [M + H]⁺ |
| 123 | H | H | H | —CH₂—(3-AllylO-5-Me-pyridyl) | 510.6 [M + H]⁺ |
| 124 | Me | H | H | —CH₂—(3-cPr-4-Me-phenyl) | 530.7 [M + H]⁺ |
| 125 | H | H | H | —CH₂—(C₆H₄)—(tetrahydropyran-4-yl) | 546.6 [M + Na]⁺ |
| 126 | Cl | H | H | —CH₂—(C₆H₄)—(tetrahydropyran-4-yl) | 580.6 [M + Na]⁺ |

TABLE 1-continued

| Entry | R1 | R2 | R3 | R4 | MS |
|---|---|---|---|---|---|
| 127 | H | H | H | —CH₂—(C₆H₄)—(C₆H₁₀)— | 536.7 [M + H]⁺ |
| 128 | H | H | H | —CH₂—(C₆H₄)—(C₆H₁₀)— | 536.9 [M + H]⁺ |
| 129 | Cl | H | H | —CH₂—(C₆H₄)—(C₆H₁₀)— | 568.7 [M − H]⁻ |
| 130 | Cl | H | H | —CH₂—(C₆H₄)—(C₆H₁₀)— | 568.8 [M − H]⁻ |
| 131 | H | H | H | —CH₂—(C₆H₄)—(C₆H₁₀)—Et | 548.8 [M − H]⁻ |
| 132 | H | H | H | —CH₂—(C₆H₄)—(C₆H₁₀)—Et | 548.8 [M − H]⁻ |
| 133 | Cl | H | H | —CH₂—(Me-C₆H₃)—(C₆H₄)—OMe | 616.6 [M + Na]⁺ |
| 134 | Cl | H | H | —CH₂—(Me-C₆H₃)—(C₆H₄)—CF₃ | 630.8 [M − H]⁻ |
| 135 | Cl | H | H | —CH₂—(Me-C₆H₃)—(Cl,OMe-pyridine) | 626.7 [M − H]⁻ |
| 136 | Me | H | H | —CH₂—(C₆H₄)—(tetrahydropyran) | 538.8 [M + H]⁺ |
| 137 | Me | H | H | —CH₂—(C₆H₄)—(C₆H₁₀)— | 550.9 [M + H]⁺ |
| 138 | Me | H | H | —CH₂—(C₆H₄)—(C₆H₁₀)— | 550.9 [M + H]⁺ |

TABLE 1-continued

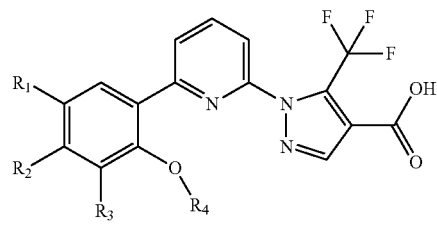

| Entry | R1 | R2 | R3 | R4 | MS |
|---|---|---|---|---|---|
| 139 | H | H | H | —CH₂—(3-methyl-4'-SO₂Me-biphenyl) | 608.8 [M + H]⁺ |
| 140 | Me | H | H | —CH₂—(4-(trans-4-OMe-cyclohexyl)phenyl) | 566.6 [M + H]⁺ |
| 141 | Me | H | H | —CH₂—(4-(cis-4-OMe-cyclohexyl)phenyl) | 586.6 [M + H]⁺ |
| 142 | H | H | H | —CH₂—(4-(trans-4-OH-cyclohexyl)phenyl) | 550.9 [M − H]⁻ |
| 143 | cPr | H | H | —CH₂—(2,4-dimethylphenyl) | 508.8 [M + H]⁺ |
| 144 | Cl | H | H | —CH₂—(2,4-dimethylphenyl) | 500.7 [M − H]⁻ |
| 145 | H | H | H | —CH(Me)—(4'-Cl-biphenyl) | 562.4 [M − H]⁻ |
| 146 | H | Cl | H | —CH₂—(4-(2-phenylethyl)phenyl) | 578.5 [M + H]⁺ |
| 147 | H | F | H | —CH₂—(4'-OMe-biphenyl) | 586.5 [M + Na]⁺ |
| 148 | H | F | H | —CH₂—(3'-Cl-4'-OMe-biphenyl) | 620.5 [M + Na]⁺ |
| 149 | H | F | H | —CH₂—(4'-CF₃-biphenyl) | 602.6 [M + H]⁺ |

TABLE 1-continued

| Entry | R1 | R2 | R3 | R4 | MS |
|---|---|---|---|---|---|
| 150 | H | H | cPr | —CH₂-(2,4-dimethylphenyl) | 508.8 [M + H]⁺ |
| 151 | H | H | Cl | —CH₂-(2,4-dimethylphenyl) | 500.7 [M − H]⁻ |
| 152 | Me | H | Cl | —CH₂-(2,4-dimethylphenyl) | 516.7 [M + H]⁺ |
| 153 | I | H | H | —CH₂-(2,4-dimethylphenyl) | 592.7 [M − H]⁻ |
| 154 | H | H | I | —CH₂-(2,4-dimethylphenyl) | 592.7 [M − H]⁻ |
| 155 | Me | H | Cl | —CH₂-(2,4,6-trimethylphenyl) | 530.7 [M + H]⁺ |
| 156 | Me | H | Cl | —CH₂-(4-CF₃-phenyl) | 556.7 [M + H]⁺ |
| 157 | Me | H | Cl | —CH₂-(4-Cl-phenyl) | 522.6 [M + H]⁺ |
| 158 | H | H | H | —CH₂-phenyl-cyclohexyl-N(Me)₂ | 580.0 [M + H]⁺ |
| 159 | H | H | Me | —CH₂-phenyl-cyclohexyl-CF₃ | 604.9 [M + H]⁺ |
| 160 | H | H | Me | —CH₂-phenyl-cyclohexyl-CF₃ | 604.9 [M + H]⁺ |

TABLE 1-continued
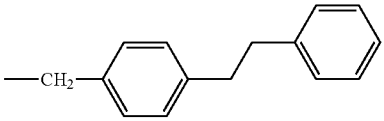
| Entry | R1 | R2 | R3 | R4 | MS |
|---|---|---|---|---|---|
| 161 | —CF₃ | H | H | 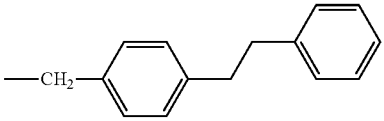 | 612.6 [M + H]⁺ |
| 162 | Cl | H | H | 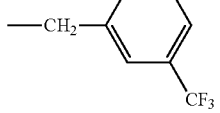 | 558.5 [M + H]⁺ |
| 163 | H | H | H | 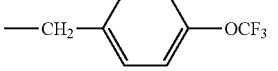 | 508.6 [M + H]⁺ |
| 164 | H | H | H | 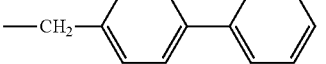 | 524.5 [M + H]⁺ |
| 165 | H | H | H | 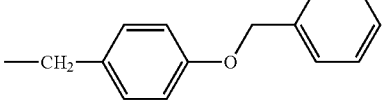 | 516.6 [M + H]⁺ |
| 166 | Cl | H | H | 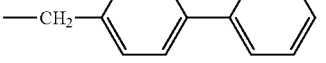 | 578.4 [M − H]⁻ |
| 167 | Cl | H | H | 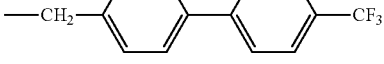 | 550.2 [M + H]⁺ |
| 168 | Cl | H | H | 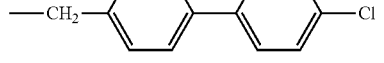 | 618.2 [M + H]⁺ |
| 169 | Cl | H | H | 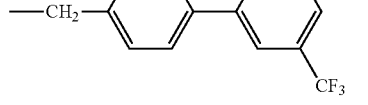 | 584.2 [M + H]⁺ |
| 170 | Cl | H | H | 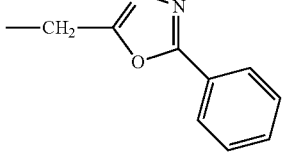 | 618.2 [M + H]⁺ |
| 171 | H | H | H |  | 508.5 [M + H]⁺ |

TABLE 1-continued

| Entry | R1 | R2 | R3 | R4 | MS |
|---|---|---|---|---|---|
| 172 | H | H | H | —CH₂-(5-(4-chlorophenyl)-1,2,4-oxadiazol-3-yl) | 542.4 [M + H]⁺ |
| 173 | H | H | H | —CH₂-(6-phenylpyridin-3-yl) | 517.5 [M + H]⁺ |
| 174 | H | H | H | —CH₂-(6-(4-chlorophenyl)pyridin-3-yl) | 551.4 [M + H]⁺ |
| 175 | H | H | H | —CH₂-(6-(4-trifluoromethylphenyl)pyridin-3-yl) | 585.4 [M + H]⁺ |
| 176 | Me | H | H | —CH₂-(4-(2-phenylethyl)phenyl) | 558.5 [M + H]⁺ |
| 177 | F | H | H | —CH₂-(4-(2-phenylethyl)phenyl) | 562.5 [M + H]⁺ |

The compounds in TABLE 2 were prepared using the chemistry described in Examples 1-9.

TABLE 2

| Entry | R1 | R2 | R3 | R4 | MS |
|---|---|---|---|---|---|
| 178 | H | H | Me | —CH₂-(4-(2-phenylethyl)phenyl) | 490.2 [M + H]⁺ |

TABLE 2-continued
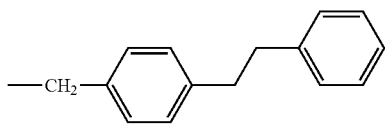
| Entry | R1 | R2 | R3 | R4 | MS |
|---|---|---|---|---|---|
| 179 | Cl | H | Me |  | 524.1 [M + H]+ |
| 180 | H | H | Me |  | 462.2 [M + H]+ |
| 181 | Cl | H | Me | 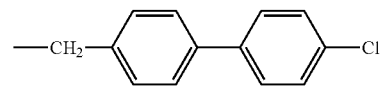 | 496.1 [M + H]+ |
| 182 | H | H | Me | 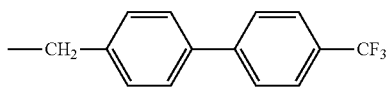 | 496.1 [M + H]+ |
| 183 | H | H | Me | 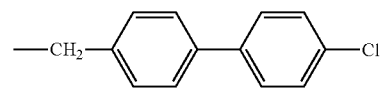 | 529.9 [M + H]+ |
| 184 | H | H | CF2H | 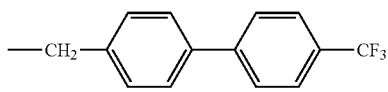 | 532.0 [M + H]+ |
| 185 | H | H | CF2H | 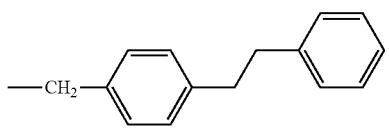 | 566.2 [M + H]+ |
| 186 | H | H | CF2H | 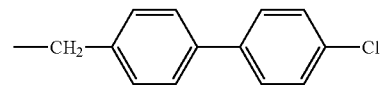 | 526.2 [M + H]+ |
| 187 | Cl | H | CF2H | 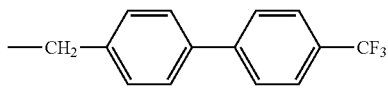 | 566.0 [M + H]+ |
| 188 | Cl | H | CF2H | 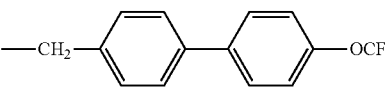 | 600.0 [M + H]+ |
| 189 | H | H | CF2H | 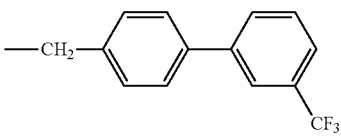 | 582.0 [M + H]+ |
| 190 | H | H | CF2H |  | 566.1 [M + H]+ |

TABLE 2-continued
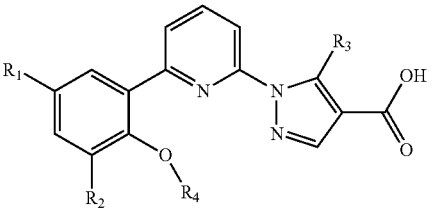
| Entry | R1 | R2 | R3 | R4 | MS |
|---|---|---|---|---|---|
| 191 | Me | H | CF2H | 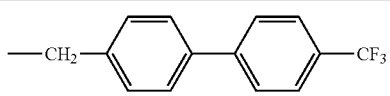 | 580.5 [M + H]+ |
| 192 | Me | H | CF2H | 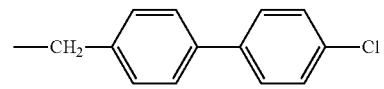 | 546.5 [M + H]+ |
| 193 | H | H | CF2H | 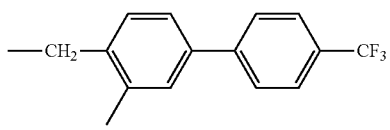 | 580.5 [M + H]+ |
| 194 | H | H | CF2H | 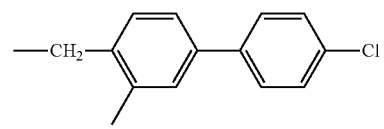 | 546.5 [M + H]+ |
| 195 | H | H | CF2H | 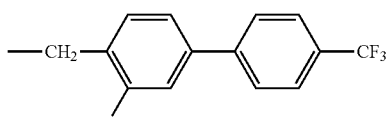 | 584.4 [M + H]+ |
| 196 | H | H | CF2H | 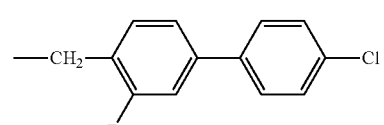 | 550.4 [M + H]+ |
| 197 | H | H | Et | 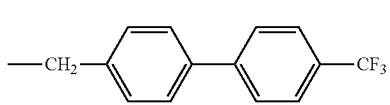 | 544.5 [M + H]+ |
| 198 | H | H | iPr | 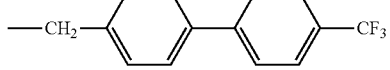 | 558.5 [M + H]+ |
| 199 | H | H | cPr | 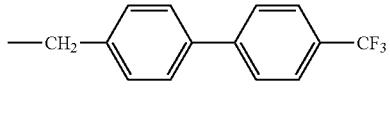 | 556.5 [M + H]+ |
| 200 | H | H | —CH2OMe | 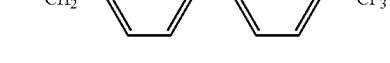 | 560.5 [M + H]+ |
| 201 | H | H | Et | 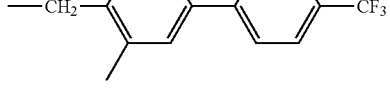 | 558.5 [M + H]+ |

TABLE 2-continued

[Structure: 2-aryl-6-(pyrazol-1-yl)pyridine with pyrazole bearing R3 and COOH; aryl ring bears R1, R2, and OR4]

| Entry | R1 | R2 | R3 | R4 | MS |
|---|---|---|---|---|---|
| 202 | H | H | iPr | —CH₂—(3-methyl-4'-(trifluoromethyl)biphenyl-4-yl) | 572.5 [M + H]⁺ |
| 203 | H | H | cPr | —CH₂—(3-methyl-4'-(trifluoromethyl)biphenyl-4-yl) | 570.5 [M + H]⁺ |
| 204 | H | H | —CH₂OMe | —CH₂—(3-methyl-4'-(trifluoromethyl)biphenyl-4-yl) | 574.5 [M + H]⁺ |
| 205 | H | H | CF2H | —CH₂—(4-(trans-4-(trifluoromethyl)cyclohexyl)phenyl) | 572.6 [M + H]⁺ |
| 206 | H | H | CF2H | —CH₂—(4-(trans-4-(trifluoromethyl)cyclohexyl)phenyl) | 572.6 [M + H]⁺ |
| 207 | H | H | Pr | —CH₂—(3-methyl-4'-(trifluoromethyl)biphenyl-4-yl) | 572.6 [M + H]⁺ |
| 208 | H | H | Ph | —CH₂—(3-methyl-4'-(trifluoromethyl)biphenyl-4-yl) | 606.6 [M + H]⁺ |
| 209 | Cl | Cl | CF2H | —CH₂—(3-methyl-4'-(trifluoromethyl)biphenyl-4-yl) | 648.4 [M + H]⁺ |
| 210 | Cl | H | CF2H | —CH₂—(3-methyl-4'-(trifluoromethyl)biphenyl-4-yl) | 614.5 [M + H]⁺ |
| 211 | Cl | H | CF2H | —CH₂—(4-(trans-4-(trifluoromethyl)cyclohexyl)phenyl) | 606.5 [M + H]⁺ |
| 212 | Cl | H | CF2H | —CH₂—(4-(trans-4-(trifluoromethyl)cyclohexyl)phenyl) | 606.5 [M + H]⁺ |

TABLE 2-continued
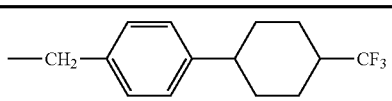
| Entry | R1 | R2 | R3 | R4 | MS |
|---|---|---|---|---|---|
| 213 | Cl | Cl | CF2H | 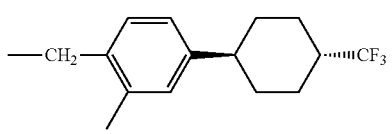 | 640.5 [M + H]+ |
| 214 | H | H | CF2H | 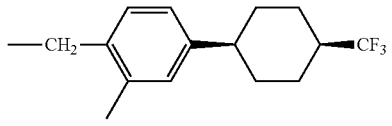 | 587.0 [M + H]+ |
| 215 | H | H | CF2H | 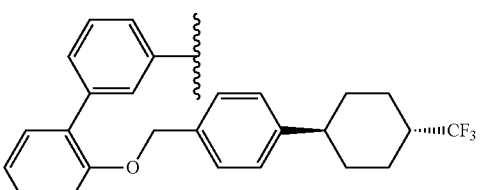 | 587.0 [M + H]+ |
The compounds in TABLE 3 were synthesized using chemistry described in Examples 1-19.
TABLE 3
| Entry | R | MS |
|---|---|---|
| 216 | 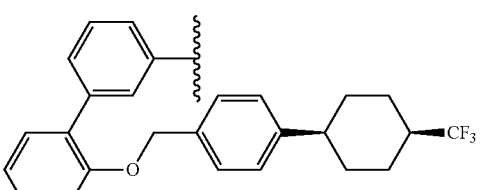 | 589.5 [M + H]+ |
| 217 | 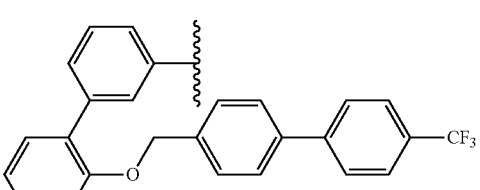 | 589.5 [M + H]+ |
| 218 | | 583.5 [M + H]+ |

TABLE 3-continued
| Entry | R | MS |
|---|---|---|
| 219 | 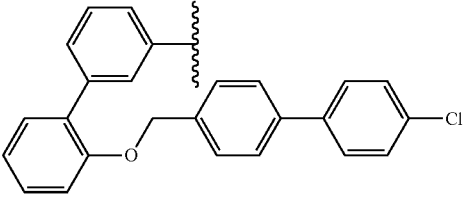 | 549.5 [M + H]+ |
| 220 | 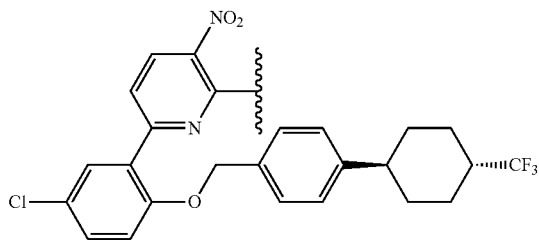 [SMILES: *c1nc(-c2cc(Cl)ccc2OCc2ccc([C@H]3CC[C@H](C(F)(F)F)CC3)cc2)ccc1[N+](=O)[O-]] | 669.9 [M + H]+ |
| 221 | 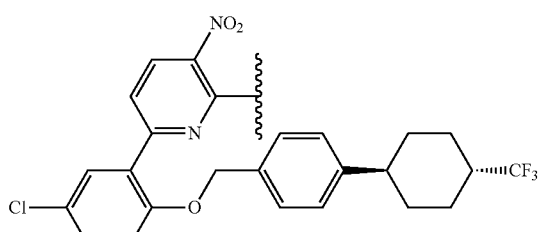 | 669.9 [M + H]+ |
| 222 | 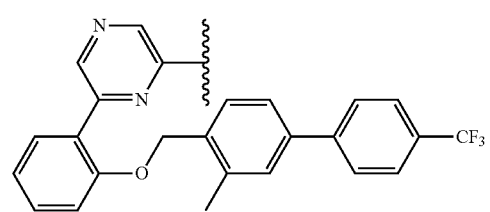 [SMILES: *c1cncc(-c2ccccc2OCc2ccc(-c3ccc(C(F)(F)F)cc3)cc2C)n1] | 599.5 [M + H]+ |
| 223 | 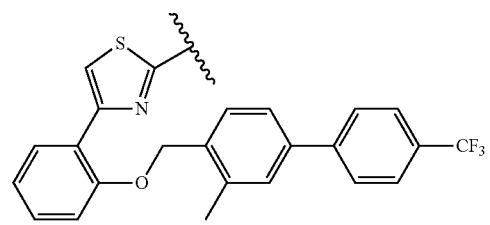 [SMILES: *c1nc(-c2ccccc2OCc2ccc(-c3ccc(C(F)(F)F)cc3)cc2C)cs1] | 604.5 [M + H]+ |
| 224 | 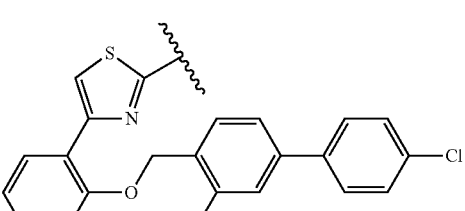 | 570.4 [M + H]+ |
| 225 | 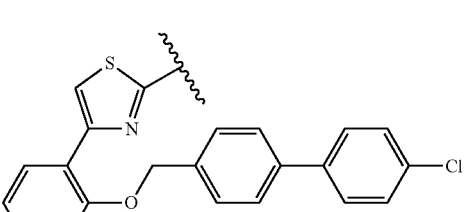 | 556.5 [M + H]+ |

TABLE 3-continued
| Entry | R | MS |
|---|---|---|
| 226 | 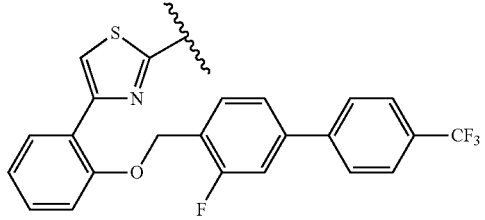 [SMILES: *c1nc(-c2ccccc2OCc2ccc(-c3ccc(C(F)(F)F)cc3)cc2F)cs1] | 608.5 [M + H]+ |
| 227 | 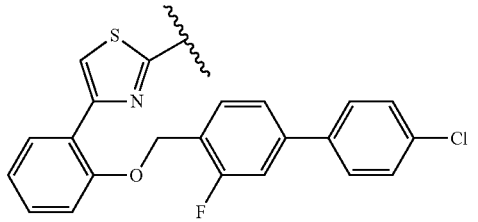 [SMILES: *c1nc(-c2ccccc2OCc2ccc(-c3ccc(Cl)cc3)cc2F)cs1] | 574.4 [M + H]+ |
| 228 | 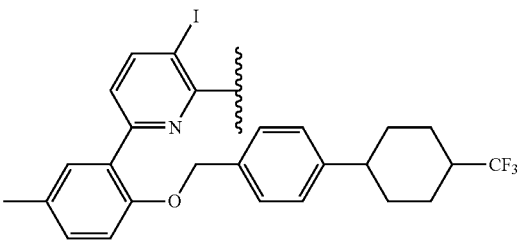 [SMILES: *c1nc(-c2cc(C)ccc2OCc2ccc(C3CCC(C(F)(F)F)CC3)cc2)ccc1I] | 730.8 [M + H]+ |
| 229 | 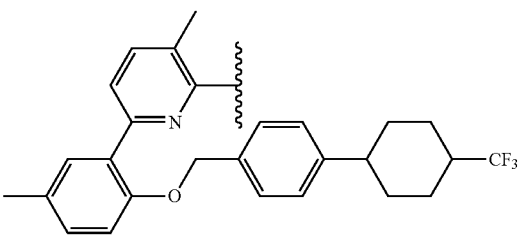 [SMILES: *c1nc(-c2cc(C)ccc2OCc2ccc(C3CCC(C(F)(F)F)CC3)cc2)ccc1C] | 618.8 [M + H]+ |
| 230 | 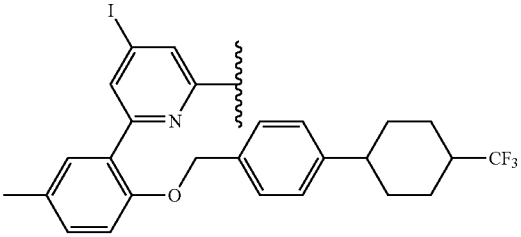 [SMILES: *c1cc(I)cc(-c2cc(C)ccc2OCc2ccc(C3CCC(C(F)(F)F)CC3)cc2)n1] | 730.8 [M + H]+ |
| 231 | 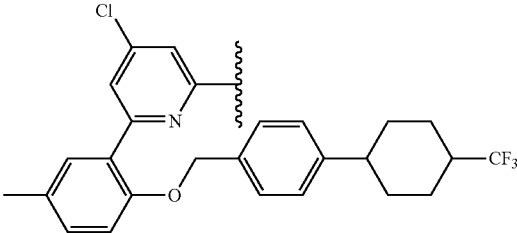 | 638.8 [M + H]+ |

TABLE 3-continued

| Entry | R | MS |
|---|---|---|
| 232 | (structure) | 551.1 [M + H]+ |
| 233 | (structure) | 517.2 [M + H]+ |
| 234 | (structure) | 750.9 [M + H]+ |
| 235 | (structure) | 750.9 [M + H]+ |

Example 236

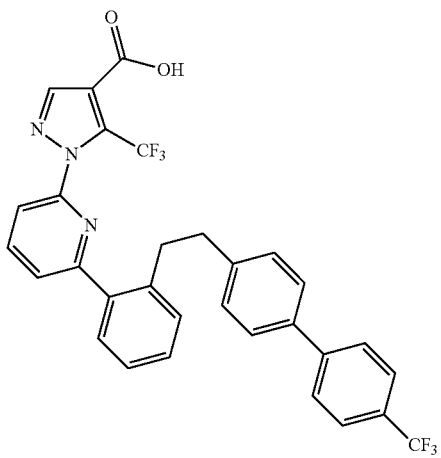 [SMILES: O=C(O)c1cnn(-c2cccc(-c3ccccc3CCc3ccc(-c4ccc(C(F)(F)F)cc4)cc3)n2)c1C(F)(F)F]

Step A. Ethyl 1-(6-{2-[(4-methoxyphenyl)ethynyl]phenyl}pyridin-2-yl)-5-(trifluoromethyl)-1H-pyrazole-4-carboxylate To a cooled (0° C.) solution of the title compound from Example 1 Step B (374 mg, 0.991 mmol) and pyridine (0.241 mL, 2.97 mmol) in DCM (5 mL) was added trifluoromethanesulfonic anhydride (0.251 mL, 1.487 mmol). The cooling bath was immediately removed, and the reaction mixture was allowed to stir at ambient temperature. After 45 min, the reaction mixture was poured into water and extracted with DCM. The layers were separated and the organic phase was concentrated in vacuo, yielding material that was sufficiently pure for use in the next step: LCMS m/z 510.0 [M+H]+. To a flask containing the unpurified triflate were added copper (I) iodide (56.1 mg, 0.294 mmol), trans-dichlorobis(triphenylphosphine) palladium (II) (68.9 mg, 0.098 mmol), tetrabutylammonium iodide (1.088 g, 2.94 mmol), and 4-methoxyphenylacetylene (195 mg, 1.47 mmol). The flask with flushed with nitrogen, and acetonitrile (5 mL) was added. The mixture was degassed with nitrogen, triethylamine (1.00 mL, 7.17 mmol) was added, and the resulting mixture was stirred at ambient temperature. After 20 h, the reaction mixture was concentrated in vacuo. Purification by flash chromatography on silica gel (0 to 30% EtOAc in hexanes, then 30 to 100% EtOAc in hexanes) provided the title compound: LCMS m/z 492.1 [M+H]+; $^1$H NMR (500 MHz, CDCl$_3$) δ 8.32 (d, J=8.0 Hz, 1H), 8.14 (s, 1H), 7.99 (t, J=8.0 Hz, 1H), 7.89 (d, J=7.5 Hz, 1H), 7.65-7.63 (m, 2H), 7.47-7.39 (m, 2H), 7.33 (d, J=8.5 Hz, 2H), 6.86 (d, J=8.5 Hz, 2H), 4.38 (q, J=7.0 Hz, 2H), 3.82 (s, 3H), 1.39 (t, J=7.0 Hz, 3H).

Step B. Ethyl 1-(6-{2-[2-(4-methoxyphenyl)ethyl]phenyl}pyridin-2-yl)-5-(trifluoromethyl)-1H-pyrazole-4-carboxylate To a degassed solution of the title compound from Example 236 Step A (255 mg, 0.519 mmol) in EtOAc (3 mL) and EtOH (3 mL) was added platinum(IV) oxide (175 mg). The reaction mixture was fitted with a hydrogen balloon attached to a 3-way adapter. The reaction flask was then evacuated and back-filled with hydrogen. After this process was repeated three times, the reaction mixture was placed under a hydrogen atmosphere, and was stirred vigorously. After 2 h, the reaction mixture was filtered through Celite, rinsing with EtOAc. The mixture was then concentrated in vacuo, and used without further purification: LCMS m/z 496.2 [M+H]$^+$.

Step C. Ethyl 5-(trifluoromethyl)-1-(6-{2-[2-(4-{[(trifluoromethyl)sulfonyl]oxy}phenyl)ethyl]phenyl}pyridin-2-yl)-1H-pyrazole-4-carboxylate To a cooled (0° C.) solution of the title compound from Example 236 Step B (177 mg, 0.357 mmol) in DCM (3 mL) was added boron tribromide (1.07 mL, 1.0 M in DCM, 1.07 mmol). After 45 min, the reaction mixture was quenched by addition of sat. aq. NaHCO$_3$, then was allowed to warm to ambient temperature. The aqueous phase was extracted with DCM. The organic phase was dried over sodium sulfate, filtered, and concentrated in vacuo. The resulting phenol was used without further purification: LCMS m/z 482.2 [M+H]$^+$. To a cooled (0° C.) DCM (5 mL) solution of the product obtained above were added pyridine (0.087 mL, 1.07 mmol) and trifluoromethanesulfonic anhydride (0.091 mL, 0.536 mmol), and the resulting mixture was allowed to warm to ambient temperature. After 1 h, the reaction mixture was quenched by addition of sat. aq. NaHCO$_3$ and extracted with DCM. The organic phase was separated and concentrated in vacuo. Purification by flash chromatography on silica gel (0 to 40% EtOAc in hexanes, then 40 to 100% EtOAc in hexanes) provided the title compound: LCMS m/z 614.2 [M+H]$^+$.

Step D. 5-(Trifluoromethyl)-1-[6-(2-{2-[4'-(trifluoromethyl)biphenyl-4-yl]ethyl}phenyl)pyridin-2-yl]-1H-pyrazole-4-carboxylic acid A vial was charged with the title compound from Example 236 Step C (60.0 mg, 0.098 mmol), 4-trifluoromethylphenyl boronic acid (24.2 mg, 0.127 mmol), and trans-dichlorobis(triphenylphosphine) palladium (II) (6.9 mg, 0.010 mmol). Acetonitrile (0.400 mL) and sodium carbonate (0.244 mL, 1.0 M aqueous, 0.244 mmol) were added, and the mixture was degassed with nitrogen. The vial was then capped and placed in a pre-heated oil bath (70° C.). After 15 h, the mixture was diluted with water and DCM and the organic phase was filtered through a short pad of silica gel and Celite with DCM, then was concentrated in vacuo: LCMS m/z 610.4 [M+H]$^+$. To a solution of the unpurified Suzuki product in 1,4-dioxane (2.0 mL) was added lithium hydroxide (1.0 mL, 2.0 M in water, 2.00 mmol), and the resulting mixture was stirred at 50° C. After 1 h, the reaction mixture was rendered acidic by addition of aqueous hydrochloric acid, then was diluted with 1,4-dioxane and passed through a 0.45 micron syringe filter. Purification by reverse phase HPLC (60 to 100% acetonitrile in water, each with 0.1% v/v TFA) provided the title compound: LCMS m/z 582.4 [M+H]$^+$; $^1$H NMR (500 MHz, d$_6$-DMSO) δ 8.34 (s, 1H), 8.20 (t, J=8.0 Hz, 1H), 7.82-7.73 (m, 6H), 7.50 (d, J=8.0 Hz, 2H), 7.44-7.34 (m, 4H), 6.99 (d, J=8.0 Hz, 2H), 2.97-2.93 (m, 2H), 2.78-2.74 (m, 2H).

Example 237

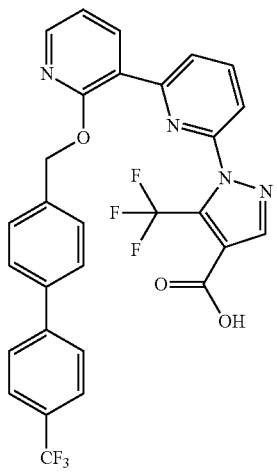 [SMILES: O=C(O)c1cnn(-c2cccc(-c3cccnc3OCc3ccc(-c4ccc(C(F)(F)F)cc4)cc3)n2)c1C(F)(F)F]

Step A. Ethyl 1-(2'-fluoro-2,3'-bipyridin-6-yl)-5-(trifluoromethyl)-1H-pyrazole-4-carboxylate A mixture of the title compound from Example 1 Step A (100 mg, 0.3 mmol), (2-fluoropyridin-3-yl)boronic acid (66 mg, 0.47 mmol), trans dichlorobis(triphenylphosphine) palladium (II) (31.0 mg, 0.05 mmol), Na$_2$CO$_3$ (0.47 mL, 2.0 M aqueous, 0.94 mmol) and acetonitrile (1 mL) in a nitrogen-filled capped vial was stirred at 100° C. After 50 min, the mixture was allowed to cool to ambient temperature, then was concentrated in vacuo. Purification by flash chromatography on silica gel using hexane:EtOAc (6:1 to 4:1 v/v) as mobile phase provided the title compound: LCMS m/z 381.1 [M+H]$^+$; $^1$H NMR (400 MHz, CDCl$_3$) δ 8.63 (m, 1H), 8.27 (m, 1H), 8.13 (s, 1H), 8.10 (d, J=7.9 Hz, 1H), 8.03 (t, J=7.9 Hz, 1H), 7.70 (d, J=7.8 Hz, 1H), 7.35 (m, 1H), 4.39 (q, J=7.1 Hz, 2H), 1.39 (t, J=7.1 Hz, 3H).

Step B. 5-(Trifluoromethyl)-1-(2'-{[4'-(trifluoromethyl)biphenyl-4-yl]methoxy}-2,3'-bipyridin-6-yl)-1H-pyrazole-4-carboxylic acid To a vial were added successively KOtBu (15.0 mg, 0.13 mmol), [4'-(trifluoromethyl)biphenyl-4-yl]methanol (US Patent 2004209936) (36.0 mg, 0.14 mmol) and DMF (0.3 mL). After 5 min, the title compound from Example 237 Step A (20.0 mg, 0.05 mmol) was added. After 30 min, the reaction mixture was treated with NaOH (0.1 mL, 3 N aqueous, 0.3 mmol), MeOH (0.1 mL) and 1,4-dioxane (0.1 mL) at 50° C. for 20 min. Reverse phase HPLC using a YMC C-18 column (65 to 100% acetonitrile in water, each with 0.1% v/v TFA) gave the title compound: LCMS m/z 584.9 [M+H]$^+$; $^1$H NMR (400 MHz, CDCl$_3$) δ 8.44 (dd, J=7.6, 1.9 Hz, 1H), 8.31 (d, J=7.8 Hz, 1H), 8.27 (dd, J=4.9, 2.0 Hz, 1H), 8.20 (s, 1H), 7.94 (t, J=7.9 Hz, 1H), 7.69 (s, 4H), 7.62-7.53 (m, 5H), 7.10 (dd, J=7.5, 4.9 Hz, 1H), 5.63 (s, 2H).

Example 238

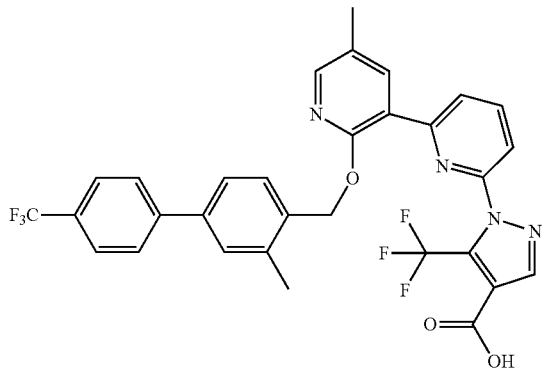 [SMILES: Cc1cnc(OCc2ccc(-c3ccc(C(F)(F)F)cc3)cc2C)c(-c2cccc(-n3ncc(C(=O)O)c3C(F)(F)F)n2)c1]

Step A. Ethyl 1-(5'-bromo-2'-fluoro-2,3'-bipyridin-6-yl)-5-(trifluoromethyl)-1H-pyrazole-4-carboxylate A mixture of the title compound from Example 1 Step A (2.0 g, 6.3 mmol), chloroform (20 mL) and 57% HI (20 mL) was heated at 100° C. with vigorous stirring. After 22 h, the organic phase was washed with brine, water, and aq. NaHCO$_3$ and the combined aqueous phases were extracted with DCM. The combined organic phases were concentrated in vacuo. Purification by flash chromatography on silica gel (hexanes-EtOAc, 9:1 to 4:1 v/v) provided a mixture (~2:1) of the title compound (LCMS m/z 412.0 [M−H]$^+$) and the title compound from Example 1 Step A. The crude mixture obtained above (1.95 g), (5-bromo-2-fluoropyridin-3-yl)boronic acid (1.31 g, 5.96 mmol), tetrakis(triphenylphosphine)palladium (0) (274 mg, 0.237 mmol), Na$_2$CO$_3$ (9.5 mL, 2 M aqueous, 19 mmol) and acetonitrile (25 mL) were stirred at 100° C. for 30 min. Aqueous workup and purification by silica gel flash chromatography using hexane-triethylamine (19:1 to 7:1 v/v) as mobile phase provided the title compound: LCMS m/z 461.0 [M+H]$^+$; $^1$H NMR (500 MHz, CD$_2$Cl$_2$) δ 8.78 (dd, J=8.5, 2.5 Hz, 1H), 8.36 (m, 1H), 8.17 (s, 1 H), 8.13 (m, 2H), 7.80 (m, 1H), 4.41 (q, J=7.1 Hz, 2H), 1.42 (t, J=7.1 Hz, 3H).

Step B. Ethyl 1-(2'-fluoro-5'-methyl-2,3'-bipyridin-6-yl)-5-(trifluoromethyl)-1H-pyrazole-4-carboxylate A mixture of the title compound from Example 238 Step A (120 mg, 0.26 mmol), tetrakis(triphenylphosphine)palladium (0) (30.0 mg, 0.026 mmol), K$_2$CO$_3$ (72.0 mg, 0.52 mmol), trimethyl boroxine (33.0 mg, 0.26 mmol), and dioxane (1.5 mL) was heated in a microwave reactor at 140° C. for 35 min, cooled, filtered and purified by silica gel flash chromatography (hexanes-EtOAc, 93:7 to 85:15 v/v) to yield the title compound: LCMS m/z 395.1 [M+H]$^+$.

Step C. 1-(5'-Methyl-2'-{[3-methyl-4'-(trifluoromethyl)biphenyl-4-yl]methoxy}-2,3'-bipyridin-6-yl-5-(trifluoromethyl)-1H-pyrazole-4-carboxylic acid The title compound was prepared according to the procedure described in Example 237 Step B, by reaction of the title compound from Example 238 Step B with [3-methyl-4'-(trifluoromethyl)biphenyl-4-yl]methanol (PCT Publication WO2005118542): LCMS m/z 612.9 [M+H]$^+$; $^1$H NMR (500 MHz, acetone-d$_6$) δ 8.18 (m, 2H), 7.91 (d, J=8.2 Hz, 2H), 7.80 (m, 3H), 7.63 (m, 2H), 5.66 (s, 2H), 2.51 (s, 3H), 2.37 (s, 3H).

Example 239

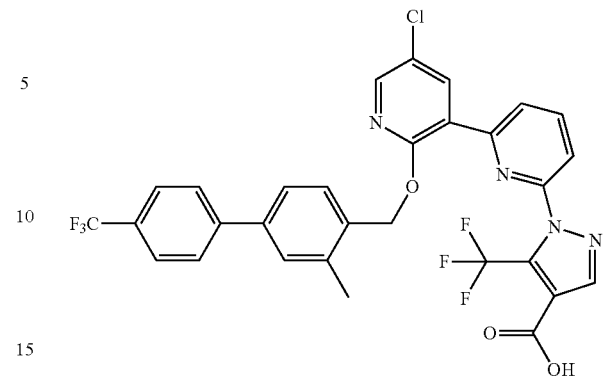

Step A. Ethyl 1-(5'-chloro-2'-fluoro-2,3'-bipyridin-6-yl)-5-(trifluoromethyl)-1H-pyrazole-4-carboxylate A mixture of the title compound from Example 238 Step A (115 mg, 0.25 mmol), CuCl (74 mg, 0.75 mmol) and DMF (1 mL) was heated in a microwave reactor at 170° C. for 10 min, diluted with DCM, filtered, concentrated and purified by silica gel flash chromatography (hexanes:EtOAc, 95:5 to 85:15 v/v) to provide the title compound: LCMS m/z 415.1 [M+H]$^+$; $^1$H NMR (500 MHz, CD$_2$Cl$_2$) δ 8.64 (dd, J=8.4, 2.6 Hz, 1H), 8.26 (m, 1H), 8.17 (s, 1H), 8.13 (m, 2H), 7.80 (m, 1H), 4.41 (q, J=7.2 Hz, 2H), 1.42 (t, J=7.2 Hz, 3H).

Step B. 1-(5'-Chloro-2'-{[3-methyl-4'-(trifluoromethyl)biphenyl-4-yl]methoxy}-2,3'-bipyridin-6-yl)-5-(trifluoromethyl)-1H-pyrazole-4-carboxylic acid The title compound was prepared according to the procedure described in Example 237 Step B, by reaction of the title compound from Example 239 Step A with [3-methyl-4'-(trifluoromethyl)biphenyl-4-yl]methanol (PCT Publication WO2005118542): LCMS m/z 632.7 [M+H]$^+$; $^1$H NMR (500 MHz, acetone-d$_6$) δ 8.22 (m, 2H), 7.92 (d, J=8.2 Hz, 2H), 7.83 (m, 3H), 7.63 (m, 2H), 5.70 (s, 2H), 2.52 (s, 3H).

Example 240

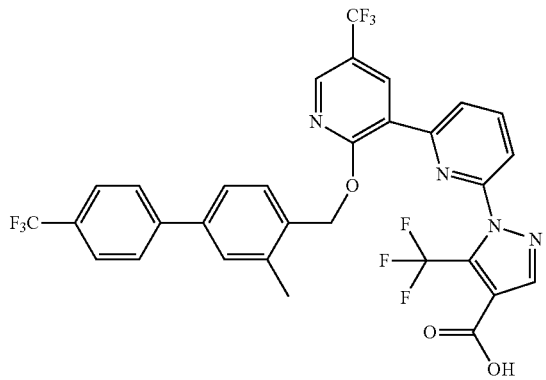 [SMILES: Cc1cc(-c2ccc(C(F)(F)F)cc2)ccc1COc1ncc(Cl)cc1-c1cccc(-n2ncc(C(=O)O)c2C(F)(F)F)n1]

Step A. Ethyl 1-[2'-fluoro-5'-(trifluoromethyl)-2,3'-bipyridin-6-yl]-5-(trifluoromethyl)-1H-pyrazole-4-carboxylate A mixture of 3-chloro-2-fluoro-5-(trifluoromethyl)pyridine (1.30 g, 6.52 mmol), bis(pinacolato)diboron (2.00 g, 7.87 mmol), KOAc (1.52 g, 15.5 mmol), 260 mg bis(tricyclohexylphosphine)palladium(0) (260 mg, 0.40 mmol) and 1,4-dioxane (10 mL) was heated at 100° C. for 50 min. Water was added and the reaction mixture was extracted with EtOAc. The organic phase was dried over sodium sulfate, passed through a silica pad and concentrated. Hexane was added and the reaction mixture was filtered, and concentrated to give crude 2-fluoro-3-(4,4,5,5-tetramethyl-1,3,2-dioxaborolan-2-yl)-5-(trifluoromethyl)pyridine. A mixture of the title compound from Example 1 Step A (1.00 g, 3.1 mmol), the crude compound obtained above (2-fluoro-3-(4,4,5,5-tetramethyl-1,3,2-dioxaborolan-2-yl)-5-(trifluoromethyl)pyridine, 2.09 g), trans-dichlorobis(triphenylphosphine) palladium (II) (154 mg, 0.22 mmol), CsF (1.43 g, 9.40 mmol), $Na_2CO_3$ (3.9 mL, 2.0 M aqueous, 7.8 mmol) and acetonitrile (15 mL) was stirred at 100° C. for 45 min. Aqueous work up with water, hexane and EtOAc, followed by silica gel flash chromatography (hexanes:EtOAc, 9:1 to 8.5:1.5 v/v) gave the title compound: LCMS m/z 449.1 [M+H]$^+$; $^1$H NMR (400 MHz, CDCl$_3$) δ 8.96 (dd, J=8.7, 2.5 Hz, 1H), 8.56 (s, 1H), 8.16-8.12 (m, 2H), 8.08 (t, J=7.9 Hz, 1H), 7.79 (dd, J=7.8, 0.8 Hz, 1H), 4.39 (q, J=7.2 Hz, 2H), 1.40 (t, J=7.2 Hz, 3H).

Step B. 1-[2'-{[3-Methyl-4'-(trifluoromethyl)biphenyl-4-yl]methoxy}-5'-(trifluoromethyl)-2,3'-bipyridin-6-yl]-5-(trifluoromethyl)-1H-pyrazole-4-carboxylic acid The title compound was prepared according to the procedure described in Example 237 Step B, by reaction of the title compound from Example 240 Step A with [3-methyl-4'-(trifluoromethyl)biphenyl-4-yl]methanol (PCT Publication WO2005118542): LCMS m/z 666.8 [M+H]$^+$; $^1$H NMR (500 MHz, acetone-d$_6$) δ (ppm) 8.78 (d, J=2.3 Hz, 1H), 8.71 (s, 1H), 8.47 (d, J=8.0 Hz, 1H), 8.26 (m, 2H), 8.22 (m, 1H), 7.92 (d, J=8.2 Hz, 2H), 7.88 (m, 1H), 7.81 (d, J=8.5 Hz, 2H), 7.66 (s, 1H), 7.59 (dd, J=7.9, 1.7 Hz, 1H), 5.80 (s, 2H), 2.54 (s, 3H).

Example 241

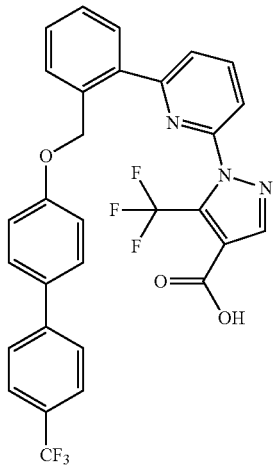 [SMILES: O=C(O)c1cnn(-c2cccc(-c3ccccc3COc3ccc(-c4ccc(C(F)(F)F)cc4)cc3)n2)c1C(F)(F)F]

Step A. Ethyl 1-{6-[2-(hydroxymethyl)phenyl]pyridin-2-yl}-5-(trifluoromethyl)-1H-pyrazole-4-carboxylate A mixture of the title compound from Example 1 Step A (300 mg, 0.94 mmol), 2,1-benzoxaborol-1(3H)-ol (189 mg, 1.40 mmol), trans-dichlorobis(triphenylphosphine) palladium (II) (94 mg, 0.14 mmol), $Na_2CO_3$ (1.4 mL, 2.0 M aqueous, 2.8 mmol) and acetonitrile (1.5 mL) in a nitrogen-filled capped vial was stirred at 100° C. for 1.5 h, cooled, concentrated and purified by silica gel flash chromatography (hexanes-EtOAc, 3:1 to 2:1 v/v) to provide the title compound: LCMS 374.1 [M−OH]$^+$; $^1$H NMR (400 MHz, CDCl$_3$) δ 8.16 (s, 1H), 8.06 (t, J=7.9 Hz, 1H), 7.77 (d, J=7.6 Hz, 1H), 7.59-7.41 (m, 5H), 4.51 (s, 2H), 4.36 (q, J=7.1 Hz, 2H), 1.40 (t, J=7.1 Hz, 3H).

Step B. 5-(Trifluoromethyl)-1-{6-[2-({[4'-(trifluoromethyl)biphenyl-4-yl]oxy}methyl)phenyl]pyridin-2-yl}-1H-pyrazole-4-carboxylic acid DIAD (0.03 mL, 0.15 mmol) was added dropwise to a solution of the title compound from Example 241 Step A (33.0 mg, 0.08 mmol), 4'-(trifluoromethyl)biphenyl-4-ol (33 mg, 0.14 mmol) and PPh$_3$ (34 mg, 0.13 mmol) in THF (0.5 mL). The reaction mixture was aged for 15 min, concentrated and treated with a mixture of 1,4-dioxane (0.15 mL), MeOH (0.15 mL) and 3 N NaOH (0.15 mL) at 60° C. for 30 min. Reverse phase HPLC using a YMC C-18 column (45 to 100% acetonitrile in water, each with 0.1% v/v TFA) provided the title compound: LCMS m/z 584.2 [M+H]$^+$; $^1$H NMR (500 MHz, CDCl$_3$) δ 8.23 (s, 1H), 8.05 (t, J=7.9 Hz, 1H), 7.78 (d, J=7.8 Hz, 1H), 7.74-7.48 (m, 11H), 6.98 (d, J=8.7 Hz, 2H), 5.28 (s, 2H).

Example 242

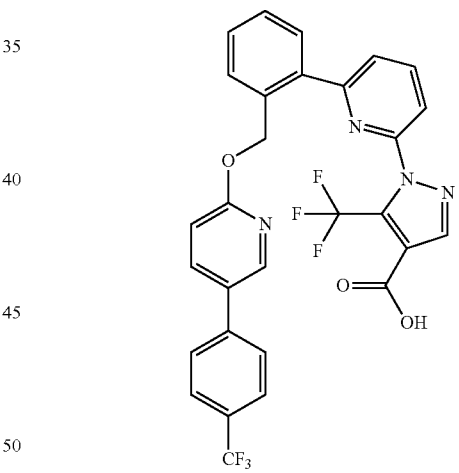

Step A. 5-(Trifluoromethyl)-1-(6-{2-[({5-[4-(trifluoromethyl)phenyl]pyridin-2-yl}oxy)methyl]phenyl}pyridin-2-yl)-1H-pyrazole-4-carboxylic acid To a solution of 5-bromo-2-fluoropyridine (72 mg, 0.41 mmol) and the title compound from Example 241 Step A (80 mg, 0.2 mmol) in DMF (1 mL) was added KOtBu (15 mg, 0.22 mmol). After 25 minutes the reaction mixture was quenched by addition of sat. aq. NH$_4$Cl. The reaction mixture was concentrated and purified by silica gel flash chromatography (7% to 20% EtOAc in hexanes) to give a mixture containing about 50% of the desired product, ethyl 1-[6-(2-{[(5-bromopyridin-2-yl)oxy]methyl}phenyl)pyridin-2-yl]-5-(trifluoromethyl)-1H-pyrazole 4-carboxylate, according to LCMS analysis: LCMS m/z 548.9 [M+H]+. A mixture of the material obtained above (35 mg), 4-trifluoromethylphenylboronic acid (24 mg, 0.13 mmol), tetrakis(triphenylphosphine)palladium(0) (15.0 mg, 0.013 mmol), Na$_2$CO$_3$ (0.128 mL, 2 M aqueous, 0.256 mmol) and DME (0.7 mL) in a nitrogen-filled capped vial was stirred at 112° C. for 15 min, cooled, concentrated and treated with a mixture of 3 N NaOH (0.1 mL), MeOH (0.1 mL) and 1,4-dioxane (0.1 mL) at 60° C. for 30 min. Reverse phase HPLC using a YMC C-18 column (45 to 100% acetonitrile in water, each with 0.1% v/v TFA) gave the title compound: LCMS m/z 584.9 [M+H]+; $^1$H NMR (500 MHz, d$_6$-DMSO) δ 8.40 (d, J=2.4 Hz, 1H), 8.22 (m, 2H), 8.04 (dd, J=8.7, 2.4 Hz, 1H), 7.89 (d, J=7.8 Hz, 1H), 7.86 (d, J=8.0 Hz, 2H), 7.80 (d, J=8.0 Hz, 2H), 7.76 (d, J=8.0 Hz, 1H), 7.51 (m, 2H), 6.83 (d, J=8.5 Hz, 1H).

Example 243

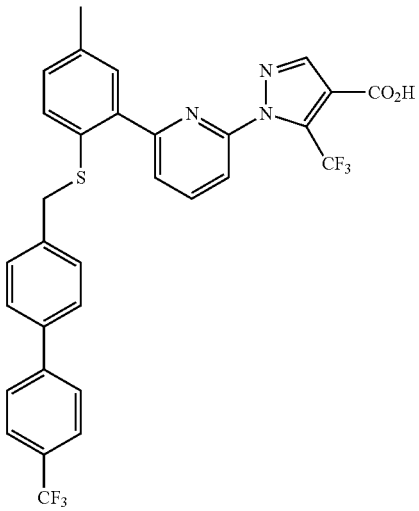 [SMILES: Cc1ccc(SCc2ccc(-c3ccc(C(F)(F)F)cc3)cc2)c(-c2cccc(-n3ncc(C(=O)O)c3C(F)(F)F)n2)c1]

Step A. Ethyl 1-[6-(5-methyl-2-{[(trifluoromethyl)sulfonyl]oxy}phenyl)pyridin-2-yl]-5-(trifluoromethyl)-1H-pyrazole-4-carboxylate To a cooled (−78° C.) solution of the title compound from Example 8 Step B (2.05 g, 5.24 mmol) and pyridine (1.06 mL, 13.1 mmol) in DCM (50 mL) was added triflic anhydride (1.06 mL, 6.29 mmol), and the reaction mixture was allowed to warm to ambient temperature. After the reaction was complete, the mixture was quenched with 2 N aqueous HCl and the aqueous phase was extracted with hexanes:ethyl acetate (3:1 v/v). The organic phase was separated, dried over sodium sulfate, passed through a pad of silica gel, eluting with DCM, and concentrated in vacuo. The title compound was used without further purification: LCMS m/z 524.6 [M+H]+; $^1$H NMR (500 MHz, CDCl$_3$) δ 8.14 (s, 1H), 8.02 (t, J=7.9 Hz, 1H), 7.81 (d, J=7.8 Hz, 1H), 7.71 (s, 1H), 7.68 (d, J=8.0 Hz, 1H), 7.30 (s, 2H), 4.39 (q, J=7.2 Hz, 2H), 2.44 (s, 3H), 1.39 (t, J=7.2 Hz, 3H).

Step B. Ethyl 1-(6-{2-[(4-methoxybenzyl)thio]-5-methylphenyl}pyridin-2-yl)-5-(trifluoromethyl)-1H-pyrazole-4-carboxylate To a solution of title compound from Example 243 Step A (2.74 g, 5.23 mmol), 4-methoxy α-toluenethiol (0.88 mL, 6.28 mmol) in 1,4-dioxane (75 mL) were added DIEA (1.83 mL, 10.5 mmol), Xantphos (0.61 g, 1.05 mmol) and tris(dibenzylideneacetone)dipalladium (0) (0.48 g, 0.52 mmol), and the reaction mixture was heated at 90° C. After 15 h, the reaction mixture was allowed to cool to ambient temperature, then was diluted with hexane. The resulting yellow solid was removed by filtration, and the collected organic filtrate was concentrated in vacuo. Purification by flash chromatography on silica gel (5 to 20% ethyl acetate in hexanes) provided the title compound: LCMS m/z 528.6 [M+H]+; $^1$H NMR (500 MHz, CD$_2$Cl$_2$) δ 8.11 (s, 1H), 7.94 (t, J=7.9 Hz, 1H), 7.72 (d, J=7.8 Hz, 1H), 7.59 (d, J=8.0 Hz, 1H), 7.36 (m, 2 H), 7.17 (d, J=8.0 Hz, 1H), 7.04 (d, J=8.5 Hz, 2H) 6.74 (d, J=8.7 Hz, 2H) 4.35 (q, J=7.1 Hz, 2H), 3.87 (s, 2H), 3.73 (s, 3H), 2.37 (s, 3H), 1.37 (t, J=7.1 Hz, 3H).

Step C. Ethyl 1-[6-(2-mercapto-5-methylphenyl)pyridin-2-yl]-5-(trifluoromethyl)-1H-pyrazole-4-carboxylate and diethyl 1,1'-{dithiobis[(5-methyl-2,1-phenylene)pyridine-6,2-diyl]}bis[5-(trifluoromethyl)-1H-pyrazole-4-carboxylate]

To a solution of the title compound from Example 243 Step B (2.76 g, 5.23 mmol) in TFA (15 mL) was added anisole (1.71 mL, 15.7 mmol), and the resulting mixture was heated at 60° C. After 15 h, the mixture was allowed to cool to ambient temperature then was concentrated in vacuo. Purification by flash chromatography on silica gel (5 to 20% ethyl acetate in hexanes) provided the title compound as a mixture of monomer and disulfide dimer. LCMS m/z 408.6 [M+H]+ (monomer), LCMS m/z 406.6 [M+H]+ (dimer); $^1$H NMR (500 MHz, CD$_2$Cl$_2$) (dimer) δ 8.14 (s, 1H), 7.97 (t, J=7.9 Hz, 1H), 7.67 (d, J=7.8 Hz, 1H), 7.58 (d, J=8.1 Hz, 1H), 7.53 (d, J=8.1 Hz, 1H), 7.35 (d, J=1.1 Hz, 1H), 7.13 (dd, J=8.1, 1.5 Hz, 1H), 4.36 (q, J=7.2 Hz, 2H), 2.35 (s, 3H), 1.37 (t, J=7.1 Hz, 3H).

Step D. Ethyl 1-(6-{2-[(4-bromobenzyl)thio]-5-methylphenyl}pyridin-2-yl)-5-(trifluoromethyl)-1H-pyrazole-4-carboxylate To a solution of the title compounds from Example 243 Step C (mixture of monomer and dimer, 209 mg, ca. 0.54 mmol) and 4-bromobenzyl bromide (192 mg, 0.77 mmol) in DMF (3 mL) was added cesium carbonate (501 mg, 1.54 mmol), and the resulting mixture was stirred for 30 minutes, until the monomer was consumed. Next, sodium borohydride (58 mg, 1.54 mmol) was added, and the reaction mixture was stirred again for 45 minutes, resulting in cleavage of the disulfide bond of the dimer and formation of the desired product. Once the reaction reached completion, the mixture was cooled to 0° C. and quenched by addition of 2 N aqueous HCl. The aqueous phase was extracted with a 3:1 mixture of ethyl acetate in hexanes, and the organic phase was dried over sodium sulfate and concentrated in vacuo. Purification by flash chromatography on silica gel (0 to 15% ethyl acetate in hexanes) provided the title compound: LCMS m/z 576.6 [M+H]+; $^1$H NMR (500 MHz, CD$_2$Cl$_2$) δ 8.12 (s, 1H), 7.96 (t, J=7.8 Hz, 1H), 7.70 (d, J=7.8 Hz, 1H), 7.60 (d, J=8.1 Hz, 1H), 7.36 (d, J=1.4 Hz, 1H), 7.32 (d, J=8.2 Hz, 3H), 7.16 (dd, J=7.9, 1.5 Hz, 1H), 6.97 (d, J=8.5 Hz, 2H), 4.35 (q, J=7.1 Hz, 2H), 3.81 (s, 2H), 2.37 (s, 3H), 1.37 (t, J=7.2 Hz, 3H).

Step E. 1-{6-[5-Methyl-2-({[4'-(trifluoromethyl)biphenyl-4-yl]methyl}thio)phenyl]pyridin-2-yl}-5-(trifluoromethyl)-1H-pyrazole-4-carboxylic acid A solution of the title compound from Example 243 Step D (24 mg, 0.04 mmol), 4-(trifluoromethyl)phenylboronic acid (10.4 mg, 0.06 mmol), trans dichlorobis(triphenylphosphine) palladium (II) (8.9 mg, 0.01 mmol), and cesium fluoride (19 mg, 0.13 mmol), in acetonitrile (0.5 mL) was stirred for 5 min, then sodium carbonate (0.13 mL, 1.0 M aqueous, 0.13 mmol) was added. The resulting mixture was stirred at 90° C. After 30 minutes, the reaction mixture was allowed to cool to ambient temperature, then was quenched with water and extracted with 30% ethyl acetate in hexane. The organic phase was dried over sodium sulfate, passed through a silica pad, eluting with DCM, and concentrated in vacuo. To a solution of the crude reaction product in 1,4-dioxane (0.200 mL) and methanol (0.030 mL) was added sodium hydroxide (0.040 mL, 1.0 M aqueous, 0.040 mmol), and the reaction mixture was then heated at 50° C. After 15 min, the reaction mixture was allowed to cool to ambient temperature. The reaction mixture was concentrated in vacuo then acidified with TFA (2 N in DMSO). Purification by reverse phase HPLC (65 to 100% acetonitrile in water, each with 0.1% v/v TFA) provided the title compound: LCMS m/z 614.9 [M+H]$^+$; $^1$H NMR (500 MHz, CD$_2$Cl$_2$) δ 8.13 (s, 1H), 7.96 (t, J=7.9 Hz, 1H), 7.74 (d, J=7.8 Hz, 1H), 7.69-7.65 (m, 4H), 7.60 (d, J=8.0 Hz, 1H), 7.46 (d, J=8.0 Hz, 2H), 7.41 (d, J=8.0 Hz, 1H), 7.37 (s, 1H), 7.18 (d, J=8.2 Hz, 3H), 3.94 (s, 2H), 2.36 (s, 3H).

The compounds listed in TABLE 4 were prepared using chemistry described in Examples 236-243.

TABLE 4

| Entry | X  | R1 | R2                                              | MS ([M + H]$^+$) |
|-------|----|----|-------------------------------------------------|------------------|
| 244   | CH | H  | —CH$_2$O—(C$_6$H$_4$)—(C$_6$H$_4$)—Cl           | 549.9            |
| 245   | CH | H  | —CH$_2$O—(C$_6$H$_4$)—(C$_6$H$_4$)—Br           | 595.8            |
| 246   | CH | Cl | —CH$_2$O—(C$_6$H$_4$)—(C$_6$H$_4$)—CF$_3$       | 617.8            |
| 247   | CH | H  | —CH$_2$O—(3-Cl-C$_6$H$_3$)—(C$_6$H$_4$)—CF$_3$  | 617.8            |
| 248   | CH | H  | —CH$_2$O—(3-Me-C$_6$H$_3$)—(C$_6$H$_4$)—CF$_3$  | 597.9            |
| 249   | CH | Me | —CH$_2$O—(3-F-C$_6$H$_3$)—(C$_6$H$_4$)—CF$_3$   | 615.8            |
| 250   | CH | Me | —CH$_2$O—(3-Me-C$_6$H$_3$)—(C$_6$H$_4$)—CF$_3$  | 611.8            |
| 251   | CH | H  | —(CH$_2$)$_2$—(C$_6$H$_4$)—(C$_6$H$_4$)—Cl      | 548.4            |
| 252   | N  | H  | —OCH$_2$—(C$_6$H$_4$)—CH$_2$CH$_2$—(C$_6$H$_5$) | 544.9            |

TABLE 4-continued

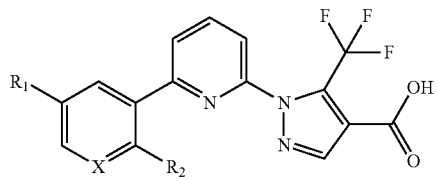

| Entry | X | R1 | R2 | MS ([M + H]+) |
|---|---|---|---|---|
| 253 | N | H | —OCH₂—⟨⟩—⟨⟩—CF₃ (with 3-Me on inner ring) | 599.0 |
| 254 | N | Cl | —OCH₂—⟨⟩—⟨⟩—Cl (with 3-Cl on inner ring) | 620.8 |
| 255 | N | Cl | —OCH₂—⟨⟩—⟨⟩—F (with 3-Cl on inner ring) | 602.8 |
| 256 | N | Me | —OCH₂—⟨⟩—⟨⟩—Cl (with 3-Cl on inner ring) | 598.8 |
| 257 | N | Me | —OCH₂—⟨⟩—⟨⟩—F (with 3-Cl on inner ring) | 582.9 |
| 258 | N | Cl | —OCH₂—⟨⟩—⟨⟩—Me (with 3-F on inner ring) | 582.9 |
| 259 | N | Cl | —OCH₂—⟨⟩—⟨⟩—Cl (with 3-F on inner ring) | 602.8 |
| 260 | N | Cl | —OCH₂—⟨⟩—⟨⟩—CF₃ (with 3-F on inner ring) | 636.7 |
| 261 | N | Cl | —OCH₂—⟨⟩—⟨⟩—Me (with 3-Cl on inner ring) | 598.8 |
| 262 | N | Cl | —OCH₂—⟨⟩—⟨⟩—CF₃ (with 3-Cl on inner ring) | 652.8 |

TABLE 4-continued
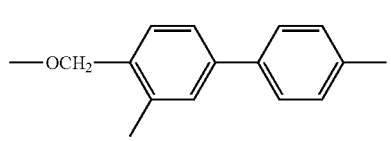
| Entry | X | R1 | R2 | MS ([M + H]⁺) |
|---|---|---|---|---|
| 263 | N | Cl | 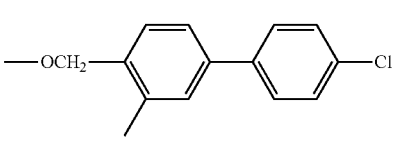 | 578.9 |
| 264 | N | Cl | 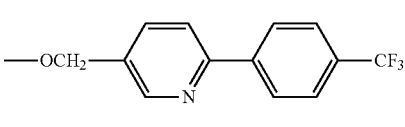 | 598.8 |
| 265 | N | Cl | 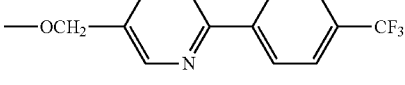 | 619.9 |
| 266 | N | Me | 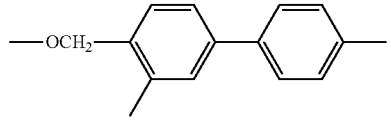 | 600.0 |
| 267 | N | CF₃ | 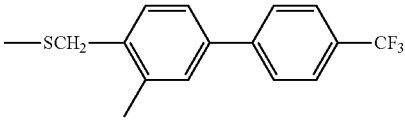 | 613.0 |
| 268 | CH | H | 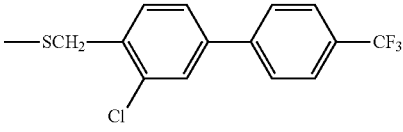 | 614.9 |
| 269 | CH | H | 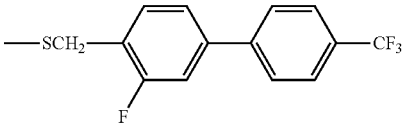 | 634.9 |
| 270 | CH | H | 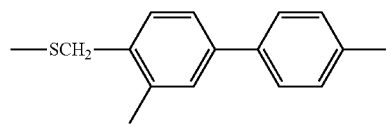 | 618.9 |
| 271 | CH | H | 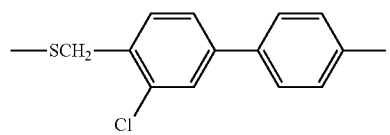 | 560.9 |
| 272 | CH | H |  | 580.9 |

TABLE 4-continued
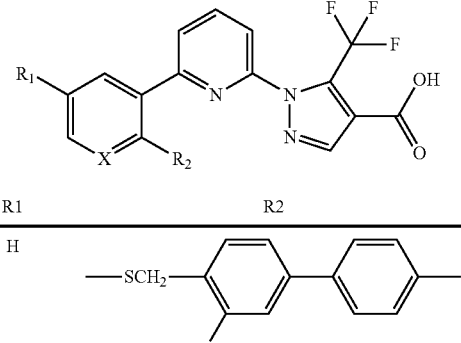
| Entry | X | R1 | R2 | MS ([M + H]+) |
|---|---|---|---|---|
| 273 | CH | H | 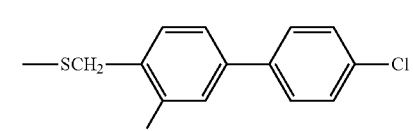 | 564.9 |
| 274 | CH | H | 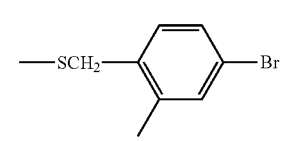 | 584.8 |
| 275 | CH | Me | 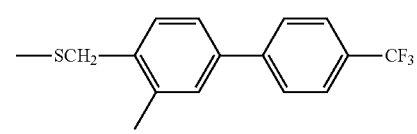 | 562.7 |
| 276 | CH | Me | 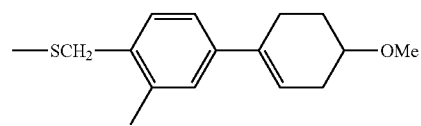 | 628.9 |
| 277 | CH | Me | 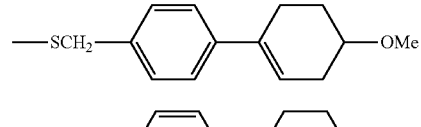 | 595.0 |
| 278 | CH | Me |  | 580.9 |
| 279 | CH | Me | 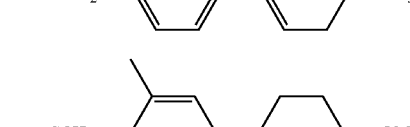 | 632.9 |
| 280 | CH | Me | 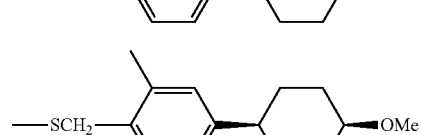 | 618.9 |
| 281 | CH | Me |  | 596.8 |
| 282 | CH | Me |  | 596.8 |
| 283 (isomer A) | CH | Me | | 635.0 |

TABLE 4-continued
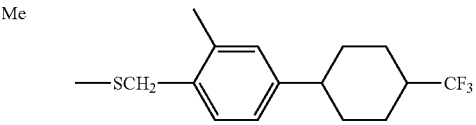
| Entry | X | R1 | R2 | MS ([M + H]+) |
|---|---|---|---|---|
| 284 (isomer B) | CH | Me | 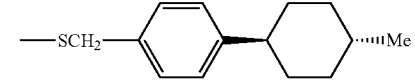 | 635.0 |
| 285 | CH | Me | 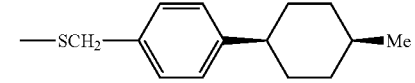 | 566.9 |
| 286 | CH | Me | 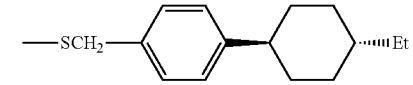 | 566.9 |
| 287 | CH | Me | 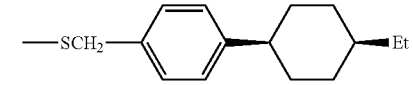 | 580.9 |
| 288 | CH | Me | 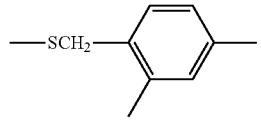 | 580.9 |
| 289 | CH | Me | 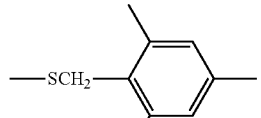 | 498.7 |
| 290 | CH | Me | 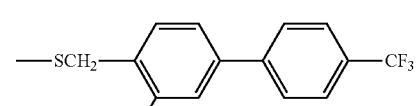 | 512.7 |
| 291 | CH | Cl | 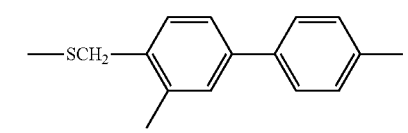 | 648.7 |
| 292 | CH | Cl | 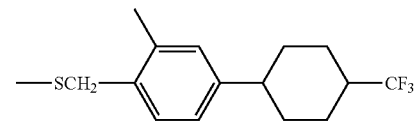 | 594.7 |
| 293 (isomer A) | CH | Cl | 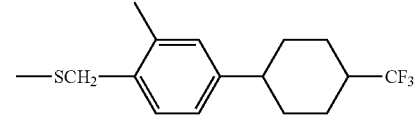 | 654.8 |
| 294 (isomer B) | CH | Cl | 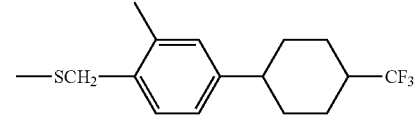 | 654.7 |

TABLE 4-continued

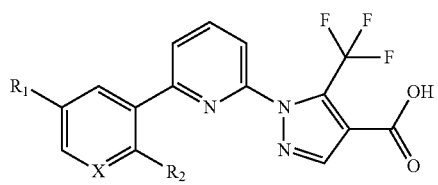

| Entry | X | R1 | R2 | MS ([M + H]+) |
|---|---|---|---|---|
| 295 | CH | Cl | —SCH₂—(2,5-dimethylphenyl) | 518.7 |
| 296 | CH | Cl | —SCH₂—(2,3,5-trimethylphenyl) | 532.8 |
| 297 | CH | Cl | —SCH₂—(2,6-dimethyl-4-tert-butylphenyl) | 574.9 |
| 298 | CH | Cl | —SCH₂—(2,3,5,6-tetramethylphenyl) | 532.8 |
| 299 | CH | Cl | —SCH₂—(4-methoxyphenyl) | 520.7 |

Example 300

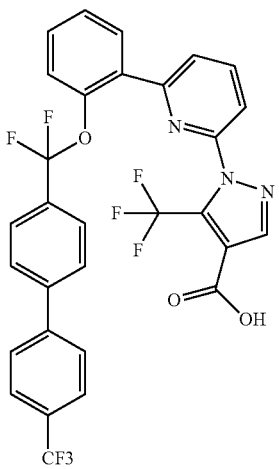 [SMILES: O=C(O)c1cnn(-c2cccc(-c3ccccc3OC(F)(F)c3ccc(-c4ccc(C(F)(F)F)cc4)cc3)n2)c1C(F)(F)F]

Step A. Ethyl 1-(6-{2-[(4-bromophenyl)(difluoro)methoxy]phenyl}pyridin-2-yl)-5-(trifluoromethyl)-1H-pyrazole-4-carboxylate To a cooled (0° C.) solution of the title compound from Example 1 Step B (515 mg, 1.37 mmol) in DMF (5 mL) was added NaH (35.0 mg, 1.46 mmol). The reaction vessel was then allowed to warm to ambient temperature for 25 min, followed by addition of 1-bromo-4-[bromo(difluoro)methyl]benzene (445 mg, 1.56 mmol, synthesized according to U.S. Pat. No. 6,939,990) and heated at 60° C. After 24 h, the reaction mixture was cooled, quenched by addition of 2 N HCl and extracted with hexane-EtOAc. Purification by silica gel flash chromatography (5% EtOAc in hexanes to 10% EtOAc in hexanes) yielded the title compound: LCMS m/z 564.1 [M−F]+; $^1$H NMR (400 MHz, CDCl$_3$) δ 8.12 (s, 1H), 7.88-7.82 (m, 2H), 7.78 (d, J=7.1 Hz, 1H), 7.57 (dd, J=7.8, 0.7 Hz, 1H), 7.50 (d, J=8.5 Hz, 2H), 7.46-7.41 (m, 2H), 7.39-7.32 (m, 3H), 4.37 (q, J=7.1 Hz, 2H), 1.38 (t, J=7.1 Hz, 3H).

Step B. 1-[6-(2-{Difluoro[4'-(trifluoromethyl)biphenyl-4-yl]methoxy}phenyl)pyridin-2-yl]-5-(trifluoromethyl)-1H-pyrazole-4-carboxylic acid A mixture of the title compound from Example 300 Step A (50.0 mg, 0.086 mmol), 4-trifluoromethylphenylboronic acid (35 mg, 0.18 mmol), trans-dichlorobis(triphenylphosphine)palladium (II) (9.0 mg, 0.013 mmol), Na$_2$CO$_3$ (0.1 mL, 2.0 M aqueous, 0.2 mmol), and MeCN (1 mL) was stirred at 90° C. for 35 min. The crude mixture was dried concentrated in vacuo. Treatment with a mixture of 0.1 mL each of 3 N NaOH, dioxane and MeOH at 50° C. for 10 min, followed by reverse phase HPLC using a YMC C-18 column (65 to 100% acetonitrile in water, each with 0.1% v/v TFA) provided the title compound: LCMS m/z 599.9 [M−F]⁺; ¹H NMR (500 MHz, acetone-$d_6$) δ 8.34 (m, 2H), 8.03 (d, J=7.6 Hz, 1H), 7.99 (d, J=8.2 Hz, 1H), 7.95-7.78 (m, 7H), 7.69 (d, J=8.5 Hz, 2H), 7.62 (m, 2H).

Example 301

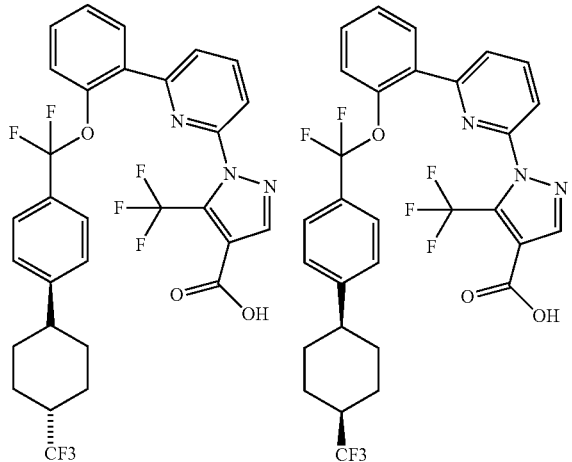

Step A. 1-{6-[2-(Difluoro{4-[trans-4-(trifluoromethyl)cyclohexyl]phenyl}methoxy)phenyl]pyridin-2-yl}-5-(trifluoromethyl)-1H-pyrazole-4-carboxylic acid and 1-{6-[2-(difluoro{4-[cis-4-(trifluoromethyl)cyclohexyl]phenyl}methoxy)phenyl]pyridin-2-yl}-5-(trifluoromethyl)-1H-pyrazole-4-carboxylic acid A mixture of the title compound from Example 300 Step A (40 mg, 0.068 mmol), 4,4,5,5-tetramethyl-2-[4-(trifluoromethyl)cyclohex-1-en-1-yl]-1,3,2-dioxaborolane (38 mg, 0.14 mmol, prepared according to *J. Med. Chem.*, 2006, 49, 3719), trans-dichlorobis(triphenylphosphine)palladium (II) (12 mg, 0.017 mmol), $Na_2CO_3$ (0.1 mL, 2.0 M aqueous, 0.2 mmol), CsF (32 mg, 0.2 mmol) and MeCN (0.5 mL) was stirred at 90° C. for 40 min. The crude mixture was dried and polar material was removed by preparative TLC (5:1 hexane:EtOAc). The remaining material was dissolved in EtOH (0.5 mL) and hydrogenated in the presence of about 12 mg Pd black for 6 hours. The resulting two isomers were separated by preparative TLC (5:1 hexane:EtOAc). For each respective isomer, treatment with a mixture of 3 N NaOH (0.1 mL), dioxane (0.1 mL) and MeOH (0.1 mL) at 50° C. for 15 min, followed by acidification with TFA (2 M in DMSO) and reverse phase HPLC using a YMC C-18 column (65 to 100% acetonitrile in water, each with 0.1% v/v TFA) gave the trans (from hydrolysis of the faster-moving isomer on normal-phase TLC) and cis (from hydrolysis of the slower-moving isomer on normal-phase TLC) title compounds. Analytical data for the trans isomer: LCMS (ESI) m/z 605.8 [M−F]⁺; ¹H NMR (500 MHz, acetone-$d_6$) δ 8.27 (s, 1H), 8.19 (t, J=7.9 Hz, 1H), 8.01 (d, J=7.8 Hz, 1H), 7.82 (d, J=8.0 Hz, 1H), 7.34 (d, J=8.0 Hz, 2H), 2.65 (m, 1H), 2.32 (m, 1H), 2.08 (m, 2H), 1.98 (m, 2H), 1.67-1.45 (m, 4H). Analytical data for the cis isomer: LCMS m/z 605.8 [M−F]⁺; ¹H NMR (400 MHz, acetone-$d_6$) δ 8.20 (s, 1H), 8.14 (t, J=7.9 Hz, 1H), 7.96 (d, J=7.9 Hz, 1H), 7.83 (d, J=7.8 Hz, 1H), 7.77 (d, J=7.9 Hz, 1H), 7.46 (d, J=8.2 Hz, 2H), 7.33 (d, J=8.2 Hz, 2H), 2.80 (m, 1H), 2.43 (m, 1H), 1.82 (m, 6H).

Example 302

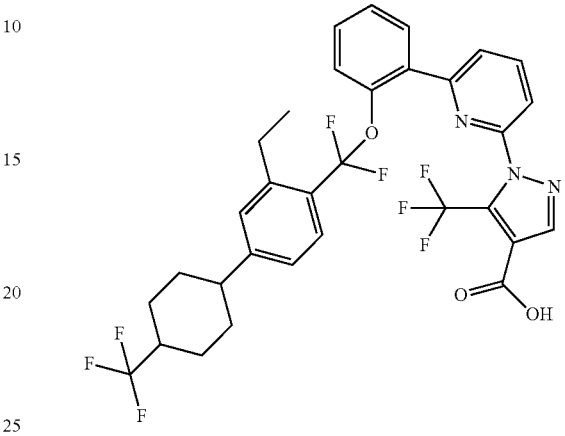

Step A. 5-Bromo-2-(difluoromethyl)benzonitrile

A mixture of 4-bromo-1-(difluoromethyl)-2-fluorobenzene (5.0 g, 22 mmol) and KCN (4.34 g, 67 mmol) was heated at 150° C. in NMP (50 mL) for 16 h. After trituration with a mixture of water, hexane, EtOAc and DCM, the organic layer was concentrated and purified by silica gel flash chromatography using hexanes:DCM (4:1 to 4:1.5 v/v) as mobile phase to yield the title compound: ¹H NMR (500 MHz, $CD_2Cl_2$) δ 7.97 (s, 1H), 7.93 (d, J=8.5 Hz, 1H), 7.67 (d, J=8.5 Hz, 1H), 6.95 (t, J=54.5 Hz, 1H).

Step B.
5-Bromo-2-[bromo(difluoro)methyl]benzonitrile

A mixture of the title compound from Example 302 Step A (2.44 g, 10.5 mmol), $CCl_3Br$ (8 mL) and $Na_2CO_3$ (480 mg, 4.5 mmol) in a sealed vessel was illuminated by a sunlamp for 30 h. Purification by silica gel flash chromatography using 8:1 to 6:1 to 4:1 hexanes:DCM as mobile phase yielded the title compound: ¹H NMR (500 MHz, $CD_2Cl_2$) δ 8.03 (s, 1H), 7.92 (d, J=8.5 Hz, 1H), 7.65 (d, J=8.5 Hz, 1H).

Step C.
5-Bromo-2-[bromo(difluoro)methyl]benzaldehyde

To a cooled (−78° C.) solution of the title compound from Example 302 Step B (1.23 g, 3.95 mmol) in toluene (10 mL) was added dropwise DIBAL-H (5.14 mL, 1.0 M in toluene, 5.14 mmol). The reaction mixture was then immediately quenched by addition of HOAc (1.5 mL), followed by MeOH (0.5 mL) and 2 N HCl. Extraction with hexanes:EtOAc, followed by flash chromatography on silica gel (hexanes:DCM, 8:1 to 3:1) to provide the title compound: ¹H NMR (500 MHz, $CD_2Cl_2$) δ(ppm) 10.63 (t, J=2.2 Hz, 1H), 8.22 (d, J=1.6 Hz, 1H), 7.87 (d, J=8.2, 1.6 Hz, 1H), 7.61 (d, J=8.2 Hz, 1H).

Step D. Ethyl 1-(6-{2-[(4-bromo-2-formylphenyl)(difluoro)methoxy]phenyl}pyridin-2-yl)-5-(trifluoromethyl)-1H-pyrazole-4-carboxylate By analogy to Example 300 Step A, reaction of the title compound from Example 302 Step C with the title compound from Example 1 Step B provided the title compound: LCMS m/z 592.5 [M−F]+.

Step E. Ethyl 1-(6-{2-[(4-bromo-2-vinylphenyl)(difluoro)methoxy]phenyl}pyridin-2-yl)-5-(trifluoromethyl)-1H-pyrazole-4-carboxylate To a cooled (0° C.) suspension of methyltriphenyl phosphonium bromide (5.33 g, 14.9 mmol) in THF (100 mL) was added dropwise n-BuLi (5.5 mL, 2.5 M in hexanes, 13.8 mmol). After aging for 40 min, the reaction mixture was allowed to warm up to ambient temperature for 25 min, at which point 7.4 mL of the supernatant was taken and added to the title compound from Example 302 Step D (270 mg, 0.442 mmol). After 30 min, the mixture was quenched by addition of water and the aqueous phase was extracted with hexane-EtOAc. The organic phase was separated and concentrated in vacuo. Purification by silica gel flash chromatography (5% to 15% EtOAc in hexanes) provided the title compound: LCMS m/z 590.5 [M−F]+; $^1$H NMR (500 MHz, CD$_2$Cl$_2$) δ 8.13 (s, 1H), 7.86 (m, 2H), 7.77 (m, 2H), 7.60 (d, J=8.0 Hz, 1H), 7.55-7.48 (m, 2H), 7.45-7.40 (m, 3H), 7.08 (m, 1H), 5.68 (d, J=17.2 Hz, 1H), 5.32 (d, J=11.0 Hz, 1H), 4.38 (q, J=7.2 Hz, 2H), 1.40 (t, J=7.2 Hz, 3H).

Step F. 1-(6-{2-[{2-Ethyl-4-[4-(trifluoromethyl)cyclohexyl]phenyl}(difluoro)methoxy]phenyl}pyridin-2-yl)-5-(trifluoromethyl)-1H-pyrazole-4-carboxylic acid The title compound was prepared according to the procedure described in Example 301, starting from the title compound from Example 302 Step E: LCMS m/z 634.6 [M−F]+; $^1$H NMR (500 MHz, acetone-d$_6$) δ 8.24 (s, 1H), 8.10 (m, 1H), 7.93 (d, J=7.8 Hz, 1H), 7.87 (d, J=7.6 Hz, 1H), 7.78 (d, J=8.0 Hz, 1H), 7.58 (m, 2H), 7.50 (d, J=8.2 Hz, 1H), 7.48 (m, 1H), 7.27 (s, 1H), 7.15 (d, 1H), 2.76 (q, J=7.6 Hz, 2H), 2.63 (m, 1H), 2.31 (m, 1H), 2.07 (m, 2H), 1.99 (m, 2H), 1.67-1.46 (m, 4H), 1.16 (t, J=7.6 Hz, 3H).

Example 303

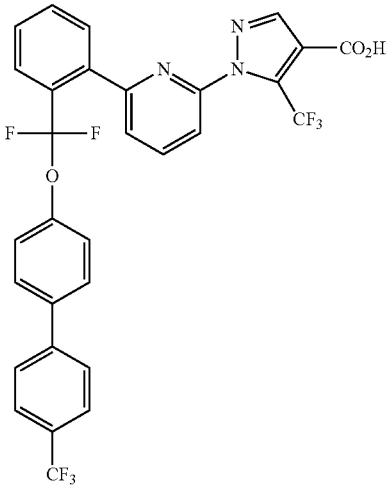 [SMILES: O=C(O)c1cnn(-c2cccc(-c3ccccc3C(F)(F)Oc3ccc(-c4ccc(C(F)(F)F)cc4)cc3)n2)c1C(F)(F)F]

Step A. 1-Bromo-2-[bromo(difluoro)methyl]benzene

A solution of 1-bromo-2-difluoromethylbenzene (9.6 g, 46.8 mmol) and N-bromosuccinimide (24.8 g, 139 mmol) in carbon tetrachloride (100 mL) was irradiated with a sunlamp. After 3 days, the reaction mixture was diluted with hexane, the precipitate was filtered off, and the collected organic filtrate was concentrated in vacuo. Purification by flash chromatography on silica gel (100% hexanes) provided the title compound: $^1$H NMR (500 M=Hz, CD$_2$Cl$_2$) δ7.74 (d, J=8.0 Hz, 1H), 7.66 (dd, J=8.0, 1.5 Hz, 1H), 7.44 (t, J=7.7 Hz, 1H), 7.37 (td, J=7.7, 1.3 Hz, 1H).

Step B. (2-Bromophenyl)(difluoro)methyl 4'-(trifluoromethyl)biphenyl-4-yl ether-4-[(2-bromophenyl)(difluoro)methoxy]-4'-(trifluoromethyl)biphenyl To a cooled (0° C.) solution of 4'-(trifluoromethyl)[1,1'-biphenyl]-4-ol (178 mg, 0.75 mmol) in DMF was added sodium hydride (27.0 mg, 1.12 mmol). Once the hydrogen evolution subsided, the reaction mixture was allowed to warm to ambient temperature. The title compound from Example 303 Step A (373 mg, 1.30 mmol) was then added to the reaction flask, and the reaction mixture was stirred at 60° C. After 15 h, the reaction mixture was quenched by addition of 2 N aqueous HCl. The aqueous phase was extracted with hexanes/ethyl acetate (3:1 v/v). The organic phase was separated, dried over sodium sulfate and concentrated in vacuo. Purification was by flash chromatography on silica gel (0-20% dichloromethane in hexanes) provided the title compound: LCMS m/z 423.5 [M−F]+; $^1$H NMR (500 MHz, CD$_2$Cl$_2$) δ 7.85 (dd, J=7.8, 1.6 Hz, 1H), 7.76 (d, J=8.0 Hz, 1H), 7.72 (s, 4H), 7.65 (dd, J=6.8, 1.9 Hz, 2H), 7.45 (d, J=8.7 Hz, 3H), 7.40 (td, J=7.7, 1.5 Hz, 1H).

Step C. Ethyl 1-[6-(4,4,5,5-tetramethyl-1,3,2-dioxaborolan-2-yl)pyridin-2-yl]-5-(trifluoromethyl)-1H-pyrazole-4-carboxylate The title compound from Example 1 Step A (538 mg, 1.68 mmol), bis(pinacolato)diboron (513 mg, 2.02 mmol), 1-1'-bis(diphenylphosphino)ferrocene (93 mg, 0.17 mmol), 1-1'-bis(diphenylphosphino) ferrocene palladium (II) chloride complex with dichloromethane (137 mg, 0.17 mmol) and potassium acetate (495 mg, 5.05 mmol) were dissolved in DMSO (10 mL), and the resulting mixture was heated at 100° C. After 2 h, the reaction mixture was allowed to cool to ambient temperature, then was quenched with brine and extracted with ether. The organic layer was separated, dried over sodium sulfate and concentrated in vacuo. Purification by flash chromatography on silica gel (20% ethyl acetate in hexanes) provided the title compound: LCMS (mass of the boronic acid observed) m/z 330.5 [M+H]+; $^1$H NMR (500 MHz, CD$_2$Cl$_2$) δ 8.10 (s, 1H), 7.92 (m, 2H), 7.57 (dd, J=6.6, 2.5 Hz, 1H), 4.36 (q, J=7.1 Hz, 2H), 1.37 (t, J=7.1 Hz, 3H), 1.37 (s, 12H).

Step D. 1-{6-[2-(Difluoro{[4'-(trifluoromethyl)biphenyl-4-yl]oxy}methyl)phenyl]pyridin-2-yl}-5-(trifluoromethyl)-1H-pyrazole-4-carboxylic acid To a solution of the title compound from Example 303 Step B (95.5 mg, 0.22 mmol) and the title compound from Example 303 Step C (106 mg, 0.33 mmol) in acetonitrile (2.0 mL) were added trans-dichlorobis(triphenylphosphine) palladium (II) (30 mg, 0.04 mmol), cesium fluoride (98 mg, 0.65 mmol), and sodium carbonate (0.90 mL, 1.0 M aqueous, 0.90 mmol). The resulting mixture was heated at 90° C. After 1.5 h, the reaction mixture was allowed to cool to ambient temperature, then was quenched with brine and extracted with 30% ethyl acetate in hexanes. The organic phase was separated and dried over sodium sulfate. The mixture was then was passed through a pad of silica gel, eluting with DCM, and concentrated in vacuo. To a solution of the crude product obtained above in dioxane (0.50 mL) and methanol (0.050 mL) was added sodium hydroxide (0.100 mL, 1.0 M aqueous, 0.100 mmol) and the resulting mixture was stirred at 50° C.

After 15 min, the reaction mixture was allowed to cool to ambient temperature and was concentrated in vacuo. The mixture was then acidified with TFA (2 M in DMSO). Purification by reverse phase HPLC (65 to 100% acetonitrile in water, each with 0.1% v/v TFA) provided the title compound: LCMS m/z 600.8 [M−F]+; 1H NMR (500 MHz, CD2Cl2) δ 8.10 (s, 1H), 8.02 (t, J=7.9 Hz, 1H), 7.74-7.60 (m, 9H), 7.53 (dd, J=6.8, 1.9 Hz, 3H), 7.06 (d, J=8.7 Hz, 2H).

The compounds in TABLE 5 were prepared using chemistry described in Examples 300-303.

TABLE 5

| Entry | R1 | R2 | R3 | MS ([M − F]+) |
|---|---|---|---|---|
| 304 | Me | H | —OCF2—(C6H4)—(C6H4)—CF3 | 613.9 |
| 305 | H | H | —OCF2—(C6H4)—(C6H4)—Cl | 565.9 |
| 306 | H | H | —OCF2—(C6H4)—cyclohexyl | 538.0 |
| 307 | H | H | —OCF2—(C6H4)—cyclopentyl | 524.0 |
| 308 | H | H | —OCF2—(C6H4)—cyclohexyl-CF3 (trans) | 605.8 |
| 309 | H | H | —OCF2—(C6H4)—cyclohexyl-CF3 (cis) | 605.8 |
| 310 | H | H | —OCF2—(C6H4)—(4,4-dimethylcyclohexyl) | 566.0 |
| 311 | Me | H | —OCF2—(C6H4)—Cl | 504.0 |
| 312 | Me | H | —OCF2—(C6H4)—SEt | 530.0 |
| 313 | Me | H | —OCF2—(C6H4)—cPr | 510.1 |
| 314 | Me | H | —OCF2—(C6H4)—cyclohexyl | 552.0 |

TABLE 5-continued
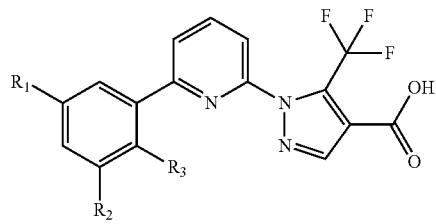
| Entry | R1 | R2 | R3 | MS ([M − F]+) |
|---|---|---|---|---|
| 315 | H | H | —OCF₂—C₆H₃(CN)—C₆H₄—Cl | 590.8 |
| 316 | H | H | —OCF₂—C₆H₃(CN)—C₆H₄—CF₃ | 624.8 |
| 317 | Cl | H | —OCF₂—C₆H₄—C₆H₄—Cl | 599.8 |
| 318 | H | H | —OCF₂—C₆H₄—C₆H₄—CO₂H | 575.9 |
| 319 | Cl | H | —OCF₂—C₆H₄—C₆H₄—CF₃ | 639.9 |
| 320 | Cl | H | —OCF₂—C₆H₄—C₆H₁₀—CF₃ | 639.9 |
| 321 | Cl | H | —OCF₂—C₆H₄—C₆H₄—OMe | 595.9 |
| 322 | H | H | —OCF₂—Pyr—C₆H₄—OMe | 561.9 |
| 323 | Me | H | —OCF₂—C₆H₄—C₆H₄—OMe | 576.0 |
| 324 | Cl | H | —OCF₂—C₆H₄—C₆H₃(Cl)—OMe | 629.9 |
| 325 | H | H | —OCF₂—C₆H₄—C₆H₃(Cl)—OMe | 595.9 |

TABLE 5-continued

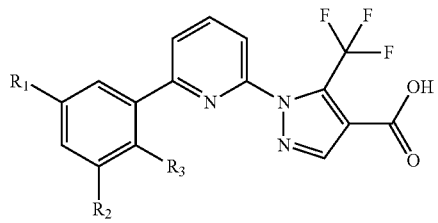

| Entry | R1 | R2 | R3 | MS ([M − F]⁺) |
|---|---|---|---|---|
| 326 | Me | H | —OCF₂—⟨phenyl⟩—⟨cyclohexyl⟩—ᴵᴵᴵOMe | 582.6 |
| 327 | Me | Br | —OCF₂—⟨phenyl⟩—⟨cyclohexyl⟩—ᴵᴵᴵCF₃ | 698.5 |
| 328 | H | H | CF₂O—⟨phenyl⟩—⟨phenyl⟩—OMe | 562.9 |
| 329 | H | H | —CF₂O—⟨phenyl (F)⟩—⟨phenyl⟩—CF₃ | 618.9 |

Example 330

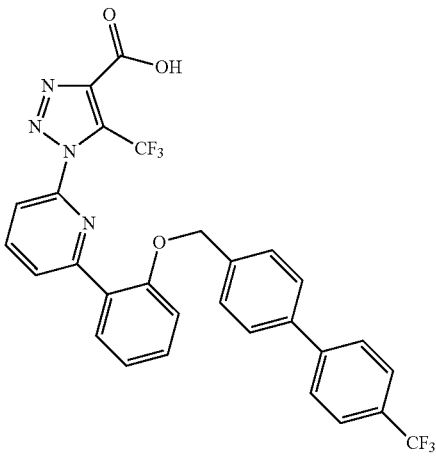

Step A. 2-Azido-6-chloropyridine

To a 250 ml round-bottom flask equipped with a mechanical stirrer, a Claisen head and an addition funnel were added 2-chloro-6-hydrazinopyridine (4.00 g, 27.9 mmol), Et₂O (20 mL) and concentrated hydrochloric acid (12 mL, 146 mmol). A solution of sodium nitrite (2.211 g, 32.0 mmol) in water (28 mL) was added dropwise to the cooled (0° C.) reaction mixture. The insoluble starting material gradually dissolved. After 2 h, the aqueous phase was extracted with ether (2×50 mL). The combined organic phase was dried over MgSO₄, and concentrated in vacuo to provide the title compound as yellow crystals: LCMS m/z 155.14 [M+H]⁺.

Step B. Ethyl 1-(6-chloropyridin-2-yl)-5-(trifluoromethyl)-1H-1,2,3-triazole-4-carboxylate To a solution of the title compound from Example 330 Step A (300 mg, 1.94 mmol) in acetonitrile (4 mL) was added ethyl 2-(ethoxymethylene)-4,4,4-trifluoro-3-oxobutyrate (0.284 mL, 1.94 mmol) followed by TEA (0.271 mL, 1.94 mmol), and the mixture was heated at 70° C. After 16 h, the reaction mixture was concentrated in vacuo. Purification by flash chromatography on silica gel (0 to 65% EtOAc in hexanes) provided the title compound as a yellow oil: LCMS m/z 320.85 [M+H]⁺; ¹H NMR (500 MHz, CD₃OD) δ 8.03 (t, J=7.9 Hz, 1H), 7.77 (d, J=7.7 Hz, 1H), 7.64 (d, J=8.0 Hz, 1H), 4.55 (q, J=7.2 Hz, 2H), 1.49 (t, J=7.2 Hz, 3H).

Step C. 5-(Trifluoromethyl)-1-[6-(2-{[4'-(trifluoromethyl)biphenyl-4-yl]methoxy}phenyl)pyridin-2-yl]-1H-1,2,3-triazole-4-carboxylic acid The title compound was prepared from the title compound from Example 330 Step B by direct analogy to the procedures outlined in Example 2 steps A-C: LCMS m/z 585.2 [M+H]⁺; ¹H NMR (500 MHz, d₆-DMSO) δ 8.29 (d, J=8.0 Hz, 1H), 8.24 (t, J=8.0 Hz, 1H), 7.91-7.88 (m, 3H), 7.81 (d, J=8.5 Hz, 2H), 7.75-7.72 (m, 3H), 7.56 (d, J=8.5 Hz, 1H), 7.49-7.45 (m, 1H), 7.32 (d, J=8.0 Hz, 1H), 7.12 (t, J=7.5 Hz, 1H), 5.33 (s, 2H).

The compounds in TABLE 6 were prepared using chemistry described in Examples 1 and 330.

TABLE 6

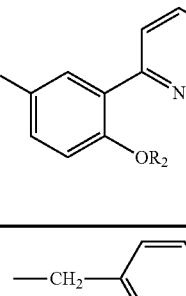

| Entry | R1 | R2 | MS |
|---|---|---|---|
| 331 | H | —CH₂—[biphenyl]—Cl | 551.0 [M + H]⁺ |
| 332 | Me | —CH₂—[biphenyl]—CF₃ | 599.5 [M + H]⁺ |
| 333 | Me | —CH₂—[methyl-biphenyl]—CF₃ | 613.5 [M + H]⁺ |
| 334 | Me | —CH₂—[fluoro-biphenyl]—CF₃ | 617.4 [M + H]⁺ |

Measurement of Soluble Guanylyl Cyclase (cGC) Activation (Cell-Based)

The activity of compounds for sGC was determined by measuring their ability to activate heterologously expressed sGC in CHO cells through the generation of intracellular cyclic guanine monophosphate (cGMP).

Human sGC subunits α1 and β1 were cloned from cDNA and inserted into a mammalian expression vector using the CMVie promoter using standard molecular biological methods. A Stably transfected CHO cell line overexpressing both sGC subunits was generated using standard cell biological methods.

Test compounds (5 ul) were dissolved in DMSO and diluted in DMSO to 50 times the desired final concentrations for 3-fold serial dilution dose response curves. The compounds were incubated with 3500-4000 cells in 5 ul phosphate-buffered saline (PBS) containing 1 nM IBMX (3-isobutyl-1-methylzanthine) at 37° C. for 1 hr in a 384-well plate (Greiner #784076) in the presence and absence of [1,2,4]oxadiazolo[4,3-a]quinoxalin-1-one (ODQ). ODQ is used to differentiate between Heme-dependent (HDA) and Heme Independent (HIA) compounds. At the end of the incubation period, the reaction is terminated and the cells are lysed. The level of intracellular cGMP is determined by an HTRF-based assay kit (CisBio, 62GM2PEC), which detects the displacement of a labeled cGMP from its specific antibody. Inflection point, maximum % of activation, and $EC_{50}$ were derived based on the plot of compound concentration vs. % activation. Compounds were determined to have an inflection point less than 10 μM and at least 20% activation.

Measurement of Soluble Guanylyl Cyclase (cGC) Activation (Enzyme-Based)

Activities of test compounds against purified sGC were evaluated in PCASA assay which is a cell-free enzymatic assay.

Human recombinant sGC enzyme with greater than 95% purity was obtained from Axxora, LLC (San Diego, Calif.).

Compounds were incubated with 0.1 ng of sGC enzyme in presence of its substrate GTP for 1 hr at 37° C. At the end of the incubation period, the reaction was stopped and the amount of cGMP generated was measured by an HTRF-based assay (CisBio, 62GN2PEC), which detects the displacement of a fluorophore-labeled cGMP from its specific antibody.

Inflection point, maximum % of activation, and EC50 were derived based on the plot of compound concentration vs % activation. In this assay, 1-{6-[5-Chloro-2-({4-[trans-4-(trifluoromethyl)cyclohexyl]-benzyl}oxy)phenyl]pyridin-2-yl}-5-(trifluoromethyl)-1H-pyrazole-4-carboxylic acid (Example 9) gave an inflection point of 11 nm and EC50 of 1.7 nM.

What is claimed is:

1. A compound of formula I, or a pharmaceutically acceptable salt thereof:

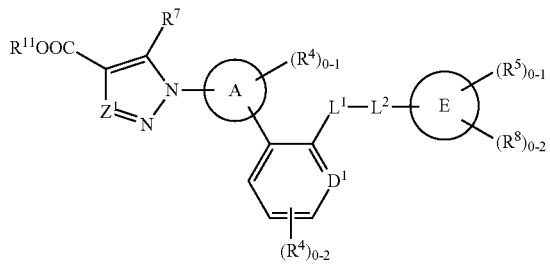

I wherein
$Z^1$ is CH;
A is

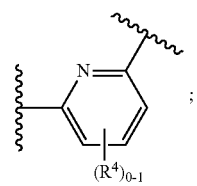

$D^1$ is CH, $CR^4$ or N;
$R^7$ is selected from the group consisting of
1) hydrogen,
2) $C_{1-6}$ alkyl wherein the alkyl group may be unsubstituted or substituted with 1-3 fluorine atoms and unsubstituted or monosubstituted with $OC_{1-3}$ alkyl,
3) $C_{3-6}$ cycloalkyl wherein the cycloalkyl group may be unsubstituted or substituted with 1-3 fluorine atoms and unsubstituted or monosubstituted with $OC_{1-3}$ alkyl, and
4) phenyl, wherein the phenyl group is unsubstituted or substituted with $C_{1-4}$ alkyl, —$OC_{1-4}$ alkyl, halogen, CN, $NO_2$, and $S(O)_{0-2}C_{1-4}$ alkyl, wherein $C_{1-4}$ alkyl and —$OC_{1-4}$ alkyl are unsubstituted or substituted with 1-3 flourine atoms;
$L^1$ is selected from the group consisting of O, S, $C(R^{12})_2$ and $CF_2$;
$L^2$ is selected from the group consisting of $(CH_2)_{2-4}$, —$C(R^{12})_2$, —$CF_2$—, O, and S, provided that when $L^1$ is O or S, $L^2$ is not O or S;
$R^{12}$ is independently selected from the group consisting of hydrogen and $C_{1-3}$ alkyl, wherein $C_{1-3}$ alkyl is unsubstituted or substituted with 1-3 flourine atoms;

E is a ring selected from the group consisting of
1) a 6-10 membered aryl ring,
2) a 5-10 membered heteroaryl ring having 1, 2 or 3 heteroatoms independently selected from the group consisting of 0, 1, 2, and 3 N atoms, 0 or 1 O atoms, and 0 or 1 S atoms,
3) a $C_{3-8}$ cycloalkyl ring;
wherein aryl, heteroaryl, and C3-8 cycloalkyl are unsubstituted or monosubstituted with R5, and unsubstituted, monosubstituted or independently disubstituted with R8;

R4, in each instance in which it occurs, is independently selected from the group consisting of halogen,
$C_{1-6}$ alkyl, wherein the alkyl group may be unsubstituted or substituted with 1-3 fluorine atoms,
—O—$C_{1-6}$ alkyl, wherein the alkyl group may be unsubstituted or substituted with 1-3 fluorine atoms,
$C_{3-8}$ cycloalkyl, unsubstituted or substituted with 1-3 fluorine atoms,
—O—$C_{3-8}$ cycloalkyl, unsubstituted or substituted with 1-3 fluorine atoms,
CN, and
$NO_2$;

$R^5$, in each instance in which it occurs, is independently selected from the group consisting of
1) $R^6$,
2) —$OR^6$,
3) $C_{1-6}$ alkyl which may be unsubstituted or substituted with 1-3 fluorine atoms, and unsubstituted or monosubstituted with a group independently selected from $C_{3-6}$ cycloalkyl, —O—$C_{1-4}$ alkyl, OH, =O, $S(O)_{0-2}C_{1-4}$ alkyl, —$OR^6$ and $R^6$,
4) $C_{1-6}$ alkenyl which may be unsubstituted or substituted with 1-3 fluorine atoms and unsubstituted or monosubstituted with a group independently selected from —O—$C_{1-4}$ alkyl, OH, =O, $S(O)_{0-2}C_{1-4}$ alkyl, —$OR^6$ and $R^6$,
5) O—$C_{1-6}$ alkyl wherein the alkyl group may be unsubstituted or substituted with 1-3 fluorine atoms, and unsubstituted or monosubstituted with a group independently selected from $C_{3-6}$ cycloalkyl and $R^6$,
6) —S—$C_{1-6}$ alkyl,
7) a $C_{3-8}$ cycloalkyl ring which is unsubstituted or mono, di- or tri-substituted with groups independently selected from fluoro and C1-4 alkyl, and unsubstituted or monosubstituted with a group independently selected from (a) $C_{1-4}$ alkyl wherein the alkyl group may be unsubstituted or substituted with 1-3 fluorine atoms, (b) —O—$C_{1-4}$ alkyl, (c) OH, (d) =O, (e) $S(O)_{0-2}C_{1-4}$ alkyl, (f) —$OR^6$, (g) $R^6$, and (h) $NR^9R^{10}$,
8) a $C_{5-8}$ cycloalkenyl ring which is unsubstituted or mono, di- or tri-substituted with a group independently selected from fluoro and $C_{1-4}$ alkyl, and unsubstituted or monosubstituted with a group independently selected from (a) $C_{1-4}$ alkyl, wherein the alkyl group may be unsubstituted or substituted with 1-3 fluorine atoms, (b) —O—$C_{1-4}$ alkyl, (c) OH, (d) =O, (e) $S(O)_{0-2}C_{1-4}$ alkyl, and (f) $R^6$, and
9) halogen;

$R^6$ is selected from the group consisting of
1) a phenyl ring which is unsubstituted, monosubstituted or disubstituted with a group independently selected from the group consisting of (a) halogen, (b) OH, (c) CN, (d) $C_{1-4}$ alkyl wherein the alkyl group may be unsubstituted or substituted with 1-3 fluorine atoms, (e) $OC_{1-4}$ alkyl wherein the alkyl group may be unsubstituted or substituted with 1-3 fluorine atoms, (f) $NO_2$, (g) $S(O)_{0-2}C_{1-4}$ alkyl, (h) $C_{2-4}$ alkenyl, (i) O—$C_{2-4}$ alkenyl, (j) $NR^9R^{10}$, and (k) COOH, and 2) a 5-6 membered heteroaryl ring containing 1-2 heteroatoms which are independently selected from N, O and S, wherein the heteroaryl ring is unsubstituted, monosubstituted or disubstituted with a group independently selected from: (a) halogen, (b) OH, (c) CN, (d) $C_{1-4}$ alkyl wherein the alkyl group may be unsubstituted or substituted with 1-3 fluorine atoms, (e) $OC_{1-4}$ alkyl wherein the alkyl group may be unsubstituted or substituted with 1-3 fluorine atoms, (f) $NO_2$, (g) $S(O)_{0-2}C_{1-6}$ alkyl, (h) $S(O)_{0-2}$ aryl, (i) $C_{2-6}$ alkenyl, (j) $OC_{2-6}$ alkenyl, (k) $NR^9R^{10}$, and (l) COOH;

$R^8$ is selected from the group consisting of
$C_{1-4}$ alkyl wherein the alkyl group may be unsubstituted or substituted with 1-3 fluorine atoms,
$C_{2-4}$ alkenyl,
halogen,
$C_{3-6}$ cycloalkyl, wherein the cycloalkyl group may be unsubstituted or substituted with 1-3 fluorine atoms,
$OC_{1-4}$ alkyl wherein the alkyl group may be unsubstituted or substituted with 1-3 fluorine atoms;
O—$C_{2-4}$ alkenyl,
$NO_2$,
$S(O)_{0-2}C_{1-4}$ alkyl, and
CN;

$R^9$ and $R^{10}$ are independently selected from the group consisting of hydrogen and $C_{1-6}$ alkyl; and
$R^{11}$ is selected from the group consisting of hydrogen and $C_{1-6}$ alkyl.

2. The compound of claim 1, or a pharmaceutically acceptable salt thereof, wherein

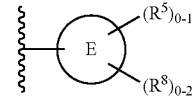

is selected from the group consisting of

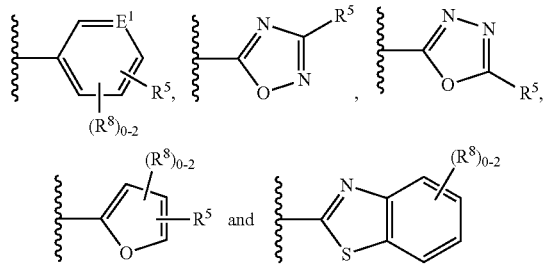

wherein $E^1$ is CH or N.

3. The compound of claim 2, or a pharmaceutically acceptable salt thereof, wherein

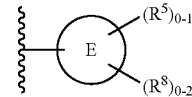

is selected from the group consisting of

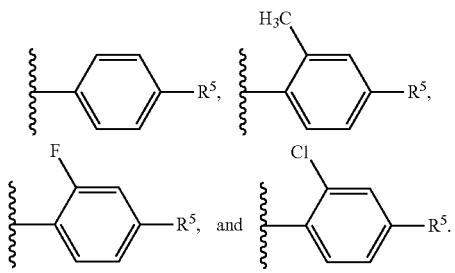

4. The compound of claim 1, or a pharmaceutically acceptable salt thereof, wherein $R^7$ is selected from the group consisting of $CH_3$, $CF_3$ and $CF_2H$.

5. The compound of claim 1, or a pharmaceutically acceptable salt thereof, wherein $L^1$ is selected from the group consisting of O and S.

6. The compound of claim 1, or a pharmaceutically acceptable salt thereof, wherein $L^2$ is selected from the group consisting of $CH_2$, $CH(CH_3)$, O, $CH_2CH_2$, $CF_2$ and $CH_2CH_2CH_2$, provided that when $L^2$ is O, $L^1$ is not O.

7. The compound of claim 6, or a pharmaceutically acceptable salt thereof, wherein $L^2$ is selected from the group consisting of $CH_2$ and $CF_2$.

8. The compound of claim 1, or a pharmaceutically acceptable salt thereof, wherein $R^4$ is selected from the group consisting of Cl, F, Br, $CH_3$, cyclopropyl, $NO_2$, and $CF_3$.

9. The compound of claim 8, or a pharmaceutically acceptable salt thereof, wherein $R^4$ is selected from the group consisting of Cl and $CH_3$.

10. The compound of claim 1, or a pharmaceutically acceptable salt thereof, wherein $R^6$ is a phenyl ring which is unsubstituted, or monosubstituted or disubstituted with a group independently selected from the group consisting of Cl, F, —$CH_3$, —$C(CH_3)_3$, $CF_3$, —$OCF_3$, —$OCH_3$, —$OCH(CH_3)_2$ and COOH.

11. The compound of claim 1, or a pharmaceutically acceptable salt thereof, wherein $R^5$ is selected from the group consisting of
1) $R^6$,
2) a $C_{3-6}$ cycloalkyl ring which is unsubstituted or mono, di- or tri-substituted with a group independently selected from phenyl, F, $CF_3$, $CH_3$, OH, and =O,
3) a pyridinyl ring, wherein the point of attachment to the pyridinyl ring is a carbon atom, and wherein the pyridinyl ring is unsubstituted or mono-substituted with $CF_3$,
4) —$CH_2$-$L^3$-$R^6$, wherein $L^3$ is —$CH_2$— or —O—,
5) —$OR^6$,
6) —$OCH_2R^6$,
7)

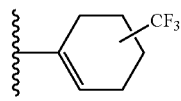

8) —$CF_3$
9) Cl, F, or Br,
10) —$CH_3$,
11) $OCH_3$,
12) $OCF_3$,
13) —CH=$CHR^6$, and
14) —$SCH_2CH_3$.

12. The compound of claim 1, or a pharmaceutically acceptable salt thereof, wherein $R^5$ is selected from the group consisting of Cl, F, Br, —$CH_3$, —$C(CH_3)_3$, $OCH_3$, $OCF_3$, —$SCH_2CH_3$,

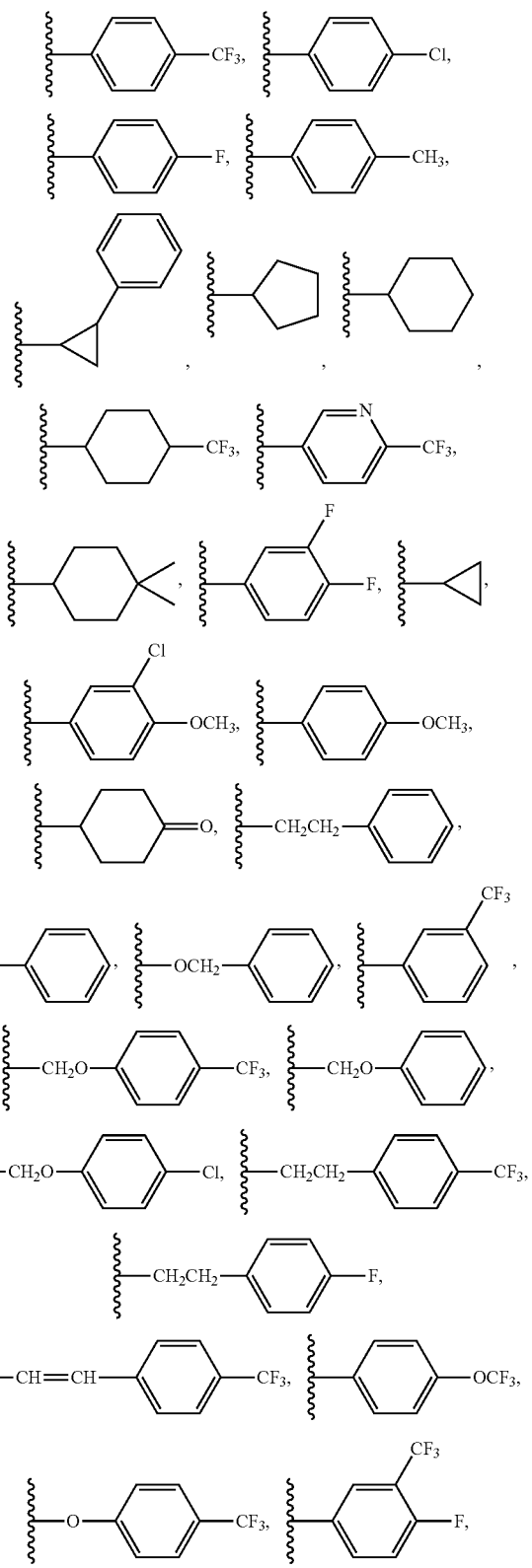

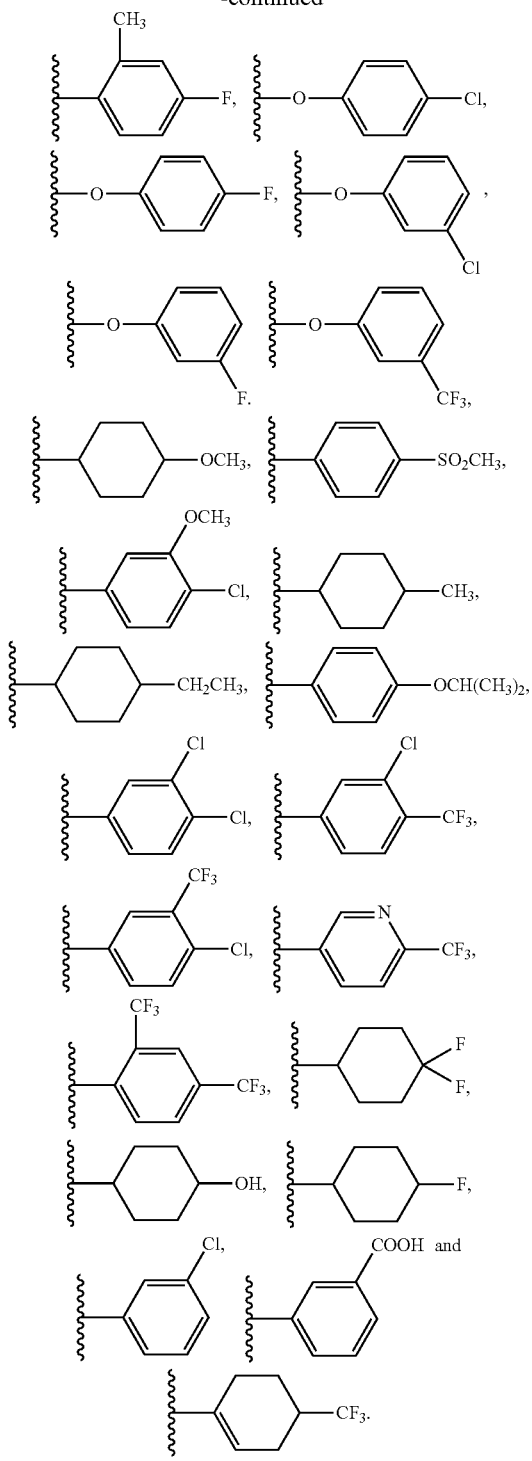

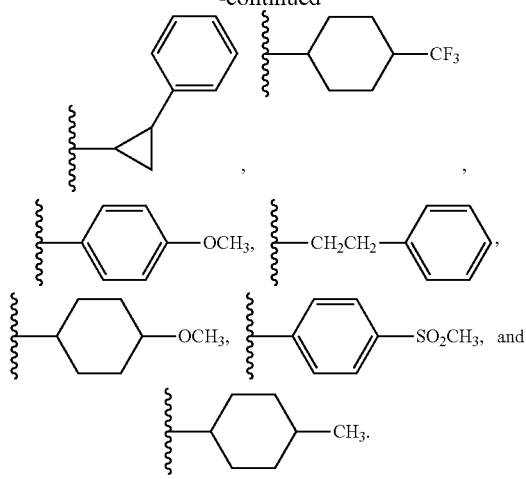

13. The compound of claim 12, or a pharmaceutically acceptable salt thereof, wherein $R^5$ is selected from the group consisting of —$CH_3$,

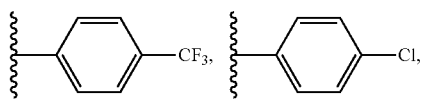

14. The compound of claim 1, or a pharmaceutically acceptable salt thereof, wherein $R^8$ is selected from the group consisting of $CH_3$, Cl, F, cyclopropyl, and $CF_3$.

15. The compound of claim 1, or a pharmaceutically acceptable salt thereof, wherein $R^{11}$ is hydrogen.

16. The compound of claim 1, or a pharmaceutically acceptable salt thereof, selected from the group consisting of 1-[6-(2-{[4-(2-Phenylethyl)benzyl]oxy}phenyl)pyridin-2-yl]-5-(trifluoromethyl)-1H-pyrazole-4-carboxylic acid, 5-(Trifluoromethyl)-1-[6-(2-{[4'-(trifluoromethyl)biphenyl-4-yl]methoxy}phenyl)pyridin-2-yl]-1H-pyrazole-4-carboxylic acid, 5-(Trifluoromethyl)-1-(6-{2-[(4-{2-[4-(trifluoromethyl)phenyl]ethyl}benzyl)-oxy]phenyl}pyridin-2-yl)-1H-pyrazole-4-carboxylic acid, 1-{6-[2-({4-[(1S,2S)-2-Phenylcyclopropyl]benzyl}oxy)phenyl]pyridin-2-yl}-5-(trifluoromethyl)-1H-pyrazole-4-carboxylic acid, 1-{6-[2-({4-[(1R,2R)-2-Phenylcyclopropyl]benzyl}oxy)phenyl]pyridin-2-yl}-5-(trifluoromethyl)-1H-pyrazole-4-carboxylic acid, 1-[6-(2-{[4-(4-Chlorophenoxy)benzyl]oxy}phenyl)pyridin-2-yl]-5-(trifluoromethyl)-1H-pyrazole-4-carboxylic acid, 5-(Trifluoromethyl)-1-{6-[2-({4-[4-(trifluoromethyl)phenoxy]benzyl}oxy)phenyl]pyridin-2-yl}-1H-pyrazole-4-carboxylic acid, 5-(Trifluoromethyl)-1-(6-{2-[(4-{[4-(trifluoromethyl)phenoxy]methyl}benzyl)-oxy]phenyl}pyridin-2-yl)-1H-pyrazole-4-carboxylic acid, 1-{6-[5-Methyl-2-({4-[trans-4-(trifluoromethyl)cyclohexyl]benzyl}oxy)phenyl]pyridin-2-yl}-5-(trifluoromethyl)-1H-pyrazole-4-carboxylic acid, 1-{6-[5-Methyl-2-({4-[cis-4-(trifluoromethyl)cyclohexyl]benzyl}oxy)phenyl]pyridin-2-yl}-5-(trifluoromethyl)-1H-pyrazole-4-carboxylic acid, 1-{6-[5-Chloro-2-({4-[trans-4-(trifluoromethyl)cyclohexyl]benzyl}oxy)phenyl]pyridin-2-yl}-5-(trifluoromethyl)-1H-pyrazole-4-carboxylic acid, 1-{6-[5-Chloro-2-({4-[cis-4-(trifluoromethyl)cyclohexyl]benzyl}oxy)phenyl]pyridin-2-yl}-5-(trifluoromethyl)-1H-pyrazole-4-carboxylic acid, 1-[6-(2-{[4-(4-Oxocyclohexyl)benzyl]oxy}phenyl)pyridin-2-yl]-5-(trifluoromethyl)-1H-pyrazole-4-carboxylic acid, 1-[6-(2-{[4-(4,4-Difluorocyclohexyl)benzyl]oxy}phenyl)pyridin-2-yl]-5-(trifluoromethyl)-1H-pyrazole-4-carboxylic acid, 1-[6-(2-{[4-(trans-4-Methoxycyclohexyl)benzyl]oxy}phenyl)pyridin-2-yl]-5-(trifluoromethyl)-1H-pyrazole-4-carboxylic acid, 1-[6-(2-{[4-(cis-4-Methoxycyclohexyl)benzyl]oxy}phenyl)pyridin-2-yl]-5-(trifluoromethyl)-1H-pyrazole-4-carboxylic acid, 1-[6-(2-{[4-(trans)-4-Methoxycyclohexyl)-2-methylbenzyl]oxy}phenyl)pyridin-2-yl]-5-(trifluoromethyl)-1H-pyrazole-4-carboxylic acid, 5-(Trifluoromethyl)-1-{6-[2-({4-[6-(trifluoromethyl)pyridin-3-yl]benzyl}-oxy)phenyl]pyridin-2-yl}-1H-pyrazole-4-carboxylic acid, 1-(6-{2-[(2,4-Dimethylbenzyl)oxy]-3-methylphenyl}pyridin-2-yl)-5-(trifluoromethyl)-1H-pyrazole-4-carboxylic acid, 1-{4-Methyl-6-[5-methyl-2-({4-[trans-4-(trifluoromethyl)cyclohexyl]benzyl}-oxy)phenyl]pyridin-2-yl}-5-(trifluoromethyl)-1H-pyrazole-4-carboxylic acid, 5-(Trifluoromethyl)-1-[6-(2-{2-[4'-(trifluoromethyl)biphenyl-4-yl]ethyl}phenyl)pyridin-2-yl]-1H-pyrazole-4-carboxylic acid, 5-(Trifluoromethyl)-1-(2'-{[4'-(trifluoromethyl)biphenyl-4-yl]methoxy}-2,3'-bipyridin-6-yl)-1H-pyrazole-4-carboxylic acid, 1-(5'-Methyl-2'-{[3-methyl-4'-(trifluoromethyl)biphenyl-4-yl]methoxy}-2,3'-bipyridin-6-yl)-5-(trifluoromethyl)-1H-pyrazole-4-carboxylic acid, 1-(5'-Chloro-2'-{[3-methyl-4'-(trifluoromethyl)biphenyl-4-yl]methoxy}-2,3'-bipyridin-6-yl)-5-(trifluoromethyl)-1H-pyrazole-4-carboxylic acid, 1-[2'-{[3-Methyl-4'-(trifluoromethyl)biphenyl-4-yl]methoxy}-5'-(trifluoromethyl)-2,3'-bipyridin-6-yl]-5-(trifluoromethyl)-1H-pyrazole-4-carboxylic acid, 5-(Trifluoromethyl)-1-{6-[2-({[4'-(trifluoromethyl)biphenyl-4-yl]oxy}methyl)phenyl]pyridin-2-yl}-1H-pyrazole-4-carboxylic acid, 5-(Trifluoromethyl)-1-(6-{2-[({5-[4-(trifluoromethyl)phenyl]pyridin-2-yl}oxy)methyl]phenyl}pyridin-2-yl)-1H-pyrazole-4-carboxylic acid, 1-{6-[5-Methyl-2-({[4'-(trifluoromethyl)biphenyl-4-yl]methyl}thio)phenyl]pyridin-2-yl}-5-(trifluoromethyl)-1H-pyrazole-4-carboxylic acid, 1-[6-(2-{Difluoro[4'-(trifluoromethyl)biphenyl-4-yl]methoxy}phenyl)pyridin-2-yl]-5-(trifluoromethyl)-1H-pyrazole-4-carboxylic acid, 1-{6-[2-(Difluoro {4-[trans-4-(trifluoromethyl)cyclohexyl]phenyl}methoxy)phenyl]pyridin-2-yl}-5-(trifluoromethyl)-1H-pyrazole-4-carboxylic acid, 1-{6-[2-(difluoro {4-[cis-4-(trifluoromethyl)cyclohexyl]phenyl}methoxy)phenyl]pyridin-2-yl}-5-(trifluoromethyl)-1H-pyrazole-4-carboxylic acid, 1-(6-{2-[{2-Ethyl-4-[4 (trifluoromethyl)cyclohexyl]phenyl}(difluoro)methoxy]phenyl}pyridin-2-yl)-5-(trifluoromethyl)-1H-pyrazole-4-carboxylic acid, and 1-{6-[2-(Difluoro {[4'-(trifluoromethyl)biphenyl-4-yl]oxy}methyl)phenyl]pyridin-2-yl}-5-(trifluoromethyl)-1H-pyrazole-4-carboxylic acid.

17. The compound of claim 1, or a pharmaceutically acceptable salt thereof, wherein
$R^{11}$ is H, $Z^1$ is CH, $R^7$ is $CF_3$ or $CF_2H$, $D^1$ is CH, $L^1$ is O, $L^2$ is $CH_2$ or $CF_2$, ring A is

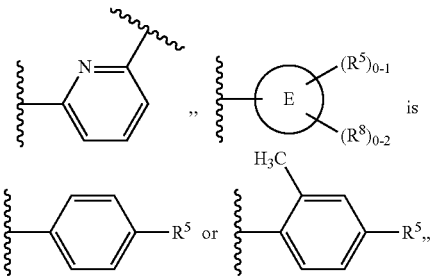

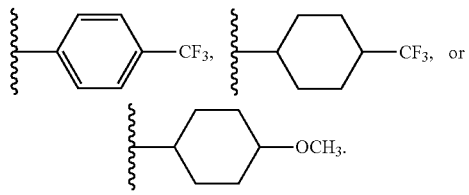

and $R^5$ is

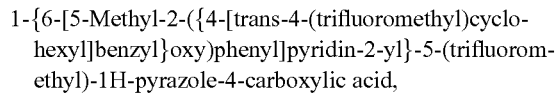
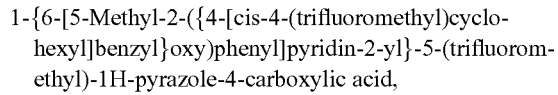
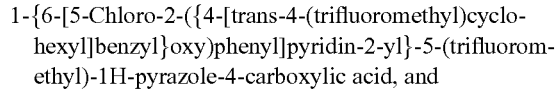
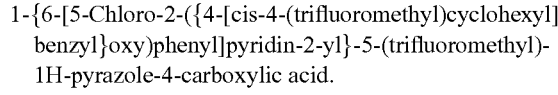

18. The compound of claim 16, or a pharmaceutically acceptable salt thereof, selected from the group consisting of 1-{6-[5-Methyl-2-({4-[trans-4-(trifluoromethyl)cyclohexyl]benzyl}oxy)phenyl]pyridin-2-yl}-5-(trifluoromethyl)-1H-pyrazole-4-carboxylic acid, 1-{6-[5-Methyl-2-({4-[cis-4-(trifluoromethyl)cyclohexyl]benzyl}oxy)phenyl]pyridin-2-yl}-5-(trifluoromethyl)-1H-pyrazole-4-carboxylic acid, 1-{6-[5-Chloro-2-({4-[trans-4-(trifluoromethyl)cyclohexyl]benzyl}oxy)phenyl]pyridin-2-yl}-5-(trifluoromethyl)-1H-pyrazole-4-carboxylic acid, and 1-{6-[5-Chloro-2-({4-[cis-4-(trifluoromethyl)cyclohexyl]benzyl}oxy)phenyl]pyridin-2-yl}-5-(trifluoromethyl)-1H-pyrazole-4-carboxylic acid.

19. A pharmaceutical composition comprising a compound of claim 1, or a pharmaceutically acceptable salt thereof, and one or more pharmaceutically acceptable carriers.

20. The pharmaceutical composition of claim 19 further comprising a compound selected from the group consisting of an angiotensin converting enzyme inhibitor, an angiotensin II receptor antagonist, a neutral endopeptidase inhibitor, an aldosterone antagonist, a renin inhibitor, an endothelin receptors antagonist, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent, and a metabolic altering agent.

21. The compound 1-{6-[5-Chloro-2-({4-[trans-4-(trifluoromethyl)cyclohexyl]benzyl}oxy)phenyl]pyridin-2-yl}-5-(trifluoromethyl)-1H-pyrazole-4-carboxylic acid having the structure

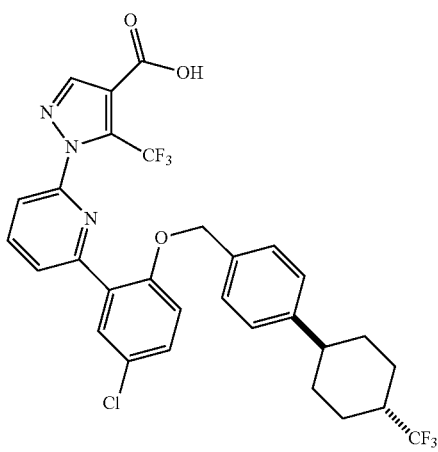

or a pharmaceutically acceptable salt thereof.

22. A pharmaceutical composition comprising a compound of claim 21, or a pharmaceutically acceptable salt thereof, and one or more pharmaceutically acceptable carriers.

23. The pharmaceutical composition of claim 22 further comprising a compound selected from the group consisting of an angiotensin converting enzyme inhibitor, an angiotensin II receptor antagonist, a neutral endopeptidase inhibitor, an aldosterone antagonist, a renin inhibitor, an endothelin receptors antagonist, a vasodilator, a calcium channel blocker, a potassium channel activator, a diuretic, a sympatholitic, a beta-adrenergic blocking drug, an alpha adrenergic blocking drug, a central alpha adrenergic agonist, a peripheral vasodilator, a lipid lowering agent, and a metabolic altering agent.

* * * * *